(12) United States Patent
Kelm et al.

(10) Patent No.: US 11,260,242 B2
(45) Date of Patent: Mar. 1, 2022

(54) SYSTEMS AND METHODS FOR USE IN TREATING SENSORY IMPAIRMENT

(71) Applicant: BIOLYST, LLC, Brooklyn Park, MN (US)

(72) Inventors: Timothy Kelm, St. Michael, MN (US); Philip S. Walter, Eden Prairie, MN (US); Robert B. Weigel, Maple Grove, MN (US); Joshua Reed, Minnetrista, MN (US)

(73) Assignee: Biolyst, LLC., Brooklyn Park, MN (US)

( * ) Notice: Subject to any disclaimer, the term of this patent is extended or adjusted under 35 U.S.C. 154(b) by 150 days.

(21) Appl. No.: 16/551,366

(22) Filed: Aug. 26, 2019

(65) Prior Publication Data

US 2020/0147408 A1  May 14, 2020

Related U.S. Application Data

(63) Continuation of application No. 14/008,265, filed as application No. PCT/US2012/030980 on Mar. 28, 2012, now Pat. No. 10,391,331.
(Continued)

(51) Int. Cl.
| | |
|---|---|
| *A61N 5/06* | (2006.01) |
| *G16H 20/40* | (2018.01) |
| *A61B 5/00* | (2006.01) |
| *A61B 5/01* | (2006.01) |
| *G16H 20/30* | (2018.01) |

(Continued)

(52) U.S. Cl.
CPC .......... *A61N 5/0622* (2013.01); *A61B 5/0057* (2013.01); *A61B 5/01* (2013.01); *A61B 5/4005* (2013.01); *A61B 5/4824* (2013.01); *G16H 20/30* (2018.01); *G16H 20/40* (2018.01); *A61B 5/389* (2021.01); *A61B 5/441* (2013.01); *A61N 5/067* (2021.08); *G16H 10/20* (2018.01)

(58) Field of Classification Search
CPC ............ A61N 5/0622; A61N 2005/067; A61B 5/4005; A61B 5/4824
See application file for complete search history.

(56) References Cited

U.S. PATENT DOCUMENTS

| | | |
|---|---|---|
| 6,607,550 B1 | 8/2003 | Bertwell |
| 7,156,866 B1 | 1/2007 | Rigs et al. |

(Continued)

OTHER PUBLICATIONS

Inselberg, et al. "Parallel Coordinates: A Tool for Visualizing Mult-Dimensional Geometry", *Visualization*, 1990. Visualization '90, Proceedings of the First IEEE Conference on Visualization, San Francisco, California, Oct. 23, 26, 1990, pp. 361-378. Retrieved Jan. 9, 2015 from the Internet: <URL: http://www.ifs.tuwien. ac.at/~mlanzenberger/teaching/ps/ws04/stiff/auth/00146402.pdf? origin=publication_detail.

(Continued)

*Primary Examiner* — Gary Jackson
*Assistant Examiner* — Zahed Kabir
(74) *Attorney, Agent, or Firm* — Mueting Raasch Group

(57) ABSTRACT

Methods and systems for use in treating one or more patient's sensory impairment, e.g., associated with peripheral neuropathy. An exemplary system may be configured to generate treatment information for treating sensory impairment in at least one body portion using photonic energy from a therapeutic laser based on data indicative of damage.

20 Claims, 30 Drawing Sheets

Related U.S. Application Data

(60) Provisional application No. 61/550,556, filed on Oct. 24, 2011, provisional application No. 61/469,084, filed on Mar. 29, 2011.

(51) Int. Cl.

| | |
|---|---|
| *G16H 10/20* | (2018.01) |
| *A61B 5/389* | (2021.01) |
| *A61N 5/067* | (2006.01) |

(56) References Cited

U.S. PATENT DOCUMENTS

| | | | |
|---|---|---|---|
| 8,043,349 B2 | 10/2011 | Springer, Jr. | |
| 10,391,331 B2 | 8/2019 | Kelm et al. | |
| 2002/0120187 A1 | 8/2002 | Eiffert | |
| 2003/0130709 A1* | 7/2003 | D.C. | G01J 3/10 607/88 |
| 2004/0267099 A1 | 12/2004 | McMahon et al. | |
| 2005/0085875 A1 | 4/2005 | Van Zuylen | |
| 2007/0150025 A1* | 6/2007 | Dilorenzo | A61B 5/4094 607/45 |
| 2007/0162093 A1 | 7/2007 | Porter et al. | |
| 2007/0203533 A1 | 8/2007 | Goren | |
| 2008/0015553 A1 | 1/2008 | Zacharias | |
| 2009/0167848 A1 | 7/2009 | Eren | |
| 2009/0326607 A1 | 12/2009 | Castel et al. | |
| 2010/0228075 A1 | 9/2010 | Lu | |
| 2010/0228076 A1 | 9/2010 | Blank et al. | |
| 2011/0098778 A1* | 4/2011 | Thimineur | A61N 1/36071 607/45 |
| 2012/0280135 A1 | 11/2012 | Bal | |

OTHER PUBLICATIONS

"K-Laser Specifications Discussion," K-LaserUSA, Franklin, Tennessee; No Publication Date. 4pgs.

Langley et al., "Functional Balance Assessment of Older Community Dwelling Adults: A Systematic Review of the Literature," *The Internet Journal of Allied Health Sciences and Practice*, Oct. 2007; 5(4):ISSN 1540-580X.

"Hear what clinicians say about LiteCure," LiteCure Lasers for Life, [Jan. 17, 2011], <http://www.litecure.com/?gclid0JbW_aUCFcIKKgodgiARnA >;4pgs.

MacKintosh et al., "A balance screening tool for older people: Reliability and validity," *International Journal of Therapy and Rehabilitation*, Dec. 7, 2006; 13(12):558-561.

Declaration of Timothy Kelm dated Dec. 31, 2015, 2 pgs.

PCT Patent Application No. US2012/030980, filed Mar. 28, 2012; International Preliminary Report on Patentability dated Oct. 10, 2013; 8 pages.

PCT Patent Application No. US2012/030980, filed Mar. 28, 2012; International Search Report / Written Opinion dated Oct. 30, 2012; 12 pages.

Smith et al., "The reliability and validity of a modified total neuropathy score-reduced and neuropathic pain severity items when used to measure chemotherapy-induced peripheral neuropathy in patients receiving taxanes and platinums," *Cancer Nurs.*, May-Jun. 2010; 33(3):173-83.

Tunér & Hode, Chapter 11, "The Mechanisms," *The New Laser Therapy Handbook*, Prima Books, Grängesberg, Sweden, 2010, pp. 528-565.

Wampler et al., "The Modified Total Neuropathy Score: A Clinically Feasible and Valid Measure of Taxane-Induced Peripheral Neuropathy in Women With Breast Cancer," *Supportive Oncology*, Sep. 2006; 4(8): W9-W16 www.supportiveoncology.net/journal/articles/0408w09.pdf.

"Welcome to Avicenna Laser Technology, Inc.," Avicenna Class IV High Power Laser Therapy, [Jan. 17, 2011], <http://avicenalaser.com>;5pgs.

Canadian Examination Report issued by the Canadian Patent Office for Application No. 2831687, Nov. 12, 2020; 5 pgs.

* cited by examiner

Fig. 11B

408

Treatment Algorithm

| Loss of Vibration (VL) | Pin Prick | Pain | # Tmnts | Recommended Plan Duration (min) | updates from tim |
|---|---|---|---|---|---|
| Above 1/3 thigh on both legs and arms above wrist | | | 17 | 45 | 40 |
| Above 1/3 thigh on both legs and hand(s) below wrist | | | 17 | 40 | 35 |
| Above 1/3 thigh on both legs | | | 17 | 30 | 30 |
| Above mid thigh one leg, other leg below knee | | | 17 | 25 | 30 |
| Above mid thigh one leg, other leg foot only | | | 17 | 20 | 20 |
| Above mid thigh one leg | | | 17 | 15 | 15 |
| Below 1/3 up thigh one leg | | | 15 | 15 | 15 |
| Below knee one leg | | | 12 | 15 | 15 |
| Below ankle one leg | | | 10 | 15 | 15 |
| Above wrist both arms | | | 12 | 20 | 20 |
| Below wrist both hands | | | 10 | 15 | 15 |
| Above wrist one arm | | | 12 | 10 | 10 |
| Below wrist one arm | | | 10 | 7.5 | 7.5 |
| Finger tips both hands | | | 8 | 15 | 15 |
| finger tips one hand | | | 8 | 7.5 | 7.5 |

Fig. 19

All are on a 11 point scale 0 - 10

| | pain | | numbness | | burning | | pin prick | | vibratory response | |
|---|---|---|---|---|---|---|---|---|---|---|
| | Initial | End | Initial | End | Initial | End | Initial | End | Initial | End |
| Patient #1 | 9 | 2 | 8 | 2 | 9 | 2 | 5.1 | 1.5 | 10 | 2.8 |
| Patient #2 | 9 | 1 | 6 | 1 | 4 | 1 | 10 | 1.5 | 10 | 1.5 |
| Patient #3 | 9 | 5 | 10 | 4 | 9 | 0 | 7.1 | 1.5 | 10 | 1.5 |

SYSTEMS AND METHODS FOR USE IN TREATING SENSORY IMPAIRMENT

CROSS-REFERENCE TO RELATED APPLICATIONS

This application is a continuation application of U.S. patent application Ser. No. 14/008,265, filed 2 Dec. 2013, issued as U.S. Pat. No. 10,391,331, on 27 Aug. 2019, which is the § 371 U.S. National Stage of International Application No. PCT/US2012/030980, filed 28 Mar. 2012, which claims the benefit of U.S. Provisional Application Ser. No. 61/469,084 filed 29 Mar. 2011, entitled "Systems and Methods for use in Treating Sensory Impairment" and U.S. Provisional Application Ser. No. 61/550,556 filed 24 Oct. 2011, entitled "Systems and Methods for use in Treating Sensory Impairment," each of which are incorporated herein by reference in their entirety.

BACKGROUND

Sensory impairment, whether acute, transient, and/or chronic (e.g., pain, soreness, tingling, burning, numbness, altered proprioception, stiffness, sharp, etc.) in a patient's extremities can be associated with a number of conditions and result from a number of causes including both mechanical, biological, and chemical insult(s). One very common condition is peripheral neuropathy (e.g., diabetic neuropathy, neuropathy associated with chemotherapy, etc.). Peripheral neuropathy may occur when the nerves connecting an individual's spinal cord and brain to other parts of the body (peripheral nerves) become damaged and/or nerve transmission is interrupted. Damage/disruption to the peripheral nerves may cause symptoms such as, for example, tingling and numbness, lack of sensation, pain, balance and coordination impairment, diminished hot and cold sensation, hypersensitivity to hot and cold, phantom hot and cold sensations, muscle weakness, etc. that may most commonly begin in the hands or feet and may spread throughout the extremities, or that may, e.g., begin in the torso and spread throughout the torso and/or abdomen.

The nerve damage of peripheral neuropathy most commonly appears as a complication of another disorder such as diabetes or AIDS, or as a reaction to drugs, alcohol, or various chemicals (including some therapeutics such as chemotherapeutics). A large portion of peripheral neuropathy presentations, e.g., roughly 30%, are considered idiopathic, or of unknown origin, and can exist seemingly without causal pathology. Nerve damage can also result from viral and bacterial infections, rheumatoid arthritis, lupus, autoimmune disorders, exposure to toxins, cancer and/or cancer treatments, vitamin deficiencies, kidney disease, liver disease, or inherited/hereditary conditions. Other causes of peripheral neuropathy include trauma, penetrating or crush injuries, bruises, fractures, and dislocated bones. Nerve damage can also be present in situations lacking clear causal pathology that is diagnosed secondary to one or more other diseases. Nerve damage can also result from extended exposure to cold or heat, radiation and/or chemical therapy for cancer, excessive vomiting (which may occur during early pregnancy), and various other causes.

Exposure to toxic chemicals can cause neuropathy. Toxic chemicals that can cause neuropathy may include industrial agents such as, e.g., solvents, heavy metals such as lead, arsenic, mercury, pesticides, nitrous oxide, etc. Sniffing glue or other toxic compounds can also cause peripheral neuropathy. Likewise, nutritional deficiencies may cause peripheral neuropathy. Alcoholism may also be a cause of neuropathy. Further, roughly 33% of the total cases of peripheral neuropathy in the United States are related to diabetes while approximately 30% are idiopathic.

When a peripheral nerve is damaged, communication between the central nervous system and the area of the body served by the peripheral nerve is disrupted. The type of damage to the nerves influences the types of symptoms that may occur. For example, if the sensory nerve fibers are damaged, the patient will likely experience changes in sensation such as numbness or pain, either at the site of nerve damage, distant thereto, or both. In addition, pain perception may vary from one patient to another. For example, one may experience broad regions of numbness, others an aching sensation, and still others areas of both sharp and/or penetrating discomfort with surrounding areas of sensory disruption. These and other symptoms may occur alone and/or in various combinations that vary with time of day, season, activity, and variable external factors including, e.g., heat, cold, humidity, and/or barometric pressure. However, if the motor fibers are damaged, muscles may be affected, e.g., causing changes in the ability to move and/or balance properly. Reductions in the ability to move can diminish the range of motion in the affected areas. For example, the reductions in the ability to move, or alterations in motor function, can change gait and stance, and may contribute to, or be contributing factors for, lower back pain. Further, for example, intrinsic foot muscles can become weakened thereby predisposing one to mechanical foot pain or plantar fasciitis as the foot pronates upon weight bearing, which can also lead to mechanical and/or structural issues. These reductions in range of motion can also lead to what is called soft tissue contracture. This "shrinking" of the connective tissues, such as tendons and joint capsules, can further limit mobility. These soft tissue contractures by themselves can become painful and lead to a burning sensation called facial pain. Motor function problems can also lead to problems with balance and coordination. Thus, peripheral neuropathy can become a safety issue, for example, when a person can no longer feel how hard they are pushing on the gas or brake pedal, or even on which pedal their foot rests.

Patient afflicted with peripheral neuropathy may experience burning and/or freezing sensations, shooting pain (e.g., which may be worse at night), gradual muscular weakening, skin that is extremely sensitive to touch, and loss of balance or coordination. In extreme cases, such patients may lose the ability to stand, walk, or hold objects. Peripheral neuropathy can also affect the nerves that control automatic functions such as heartbeat, bladder control, or bowel function. Patients may experience diarrhea or constipation, incontinence, sexual impotence, and high or low blood pressure. Further, the patients' skin may become dry and pale, and patients may sweat excessively and may also develop blurred vision, dizziness or fainting spells, or stomach and intestinal problems.

Not uncommonly, the nerve damage and numbness of peripheral neuropathy can lead to injuries and infections. Because sensation is limited with neuropathy, patients may be unaware of an injury such as a burn or a cut or even mild or severe external physical insult. The untreated wound or bruise may then become infected or may result in secondary issues such as clots and their sequelae. This may be common in diabetic patients who often develop neuropathy in their feet, and then develop painless cuts that can become infected. Balance and coordination may also be also affected, and thus, falling is a concern.

Various treatment options have been identified for peripheral neuropathy with a goal of managing the underlying causal condition, such as, in the case of diabetic neuropathy, controlling blood sugars. More often, however, the goal of treatment is the management of symptoms, such as the medications intended to mitigate pain. These approaches address the symptoms of peripheral neuropathy, not the nerve damage itself. Even when the underlying cause is identified and treated, the damage to the nerves, and the resulting pain, numbness, tingling, and other symptoms, must still be treated independent of the causal condition. There is little in the literature regarding treatments that improve touch sensation. Further, while many conventional treatment options attempt to address the symptoms related to nerve damage, the actual nerve damage related to peripheral neuropathy may still progress independent of the initial cause or triggering condition. For example, treatments for acute nerve pain may progress to transient and/or chronic pain. Further, chemotherapy and other therapeutic modalities may damage either or both nerves and muscles, and that damage may result in peripheral neuropathy, which may progress independent of the continuation or termination of chemotherapy. In addition, nerve pain and/or dysfunction may cause muscle damage and/or spasms that, in turn, may further exacerbate underlying peripheral neuropathy.

Pharmacologic pain management (e.g., a common approach) may be in the form of, e.g., anticonvulsants, analgesics, opioids, anti-seizure medications, topical preparations and anti-depressants. Some agents that have been used in symptomatic management include Pregabalin (LYRICA), Gabapentic (NEURONTIN), Oxacarbazine (TRILEPTAL), Topiramate (TOPOMAX), Lamotrigine (LAMICTAL), Duloxetine (CYMBALTA), Amitriptyline (ELAVIL), Nortriptyline (PAMELOR), Venlafaxine (EFFEXOR), Oxycodone CR (OXYCONTIN), Fentanyl (DURAGESIS TRANSDERMAL SYSTEMS), Methadone (DOLOPHINE), Lidocaine patches, and/or Capsaicin (ZOSTRIX). Unfortunately, these have significant, and undesirable, side effects. Additionally, as the body adjusts to these drugs over time, their effectiveness may diminish. Dosages are typically increased to provide some continuing relief. Ultimately, however, these therapeutic protocols often become ineffective. Given the lack of success of the conventional care approaches, patients with peripheral neuropathy may ultimately either live with the pain, numbness and tingling of early stage peripheral neuropathy, the motor control issues of later stage peripheral neuropathy, or live with the considerable side effects of drug treatments whose effectiveness may dissipate over time.

In addition, hyperalgesia (e.g., an increased sensitivity to pain) may be caused by long term (e.g., greater than three months) use of some pain management drugs. Further, hyperalgesia may be caused by damage to nociceptors and/or peripheral nerves, although the mechanism has not been definitively identified. Further, use of masking agents such as opioids may actually extend or exacerbate peripheral neuropathy due to failure to engage in physical activity resulting in degenerative disorders including muscle atrophy, depression, and withdrawal from day-to-day activities. Other alternative treatments have also been identified, including acupuncture, topical application of capsaicin cream, ingestion of alpha-lipoic acid and vitamin supplements, biofeedback, physical therapy, including exercise, massage, and the application of heat. These alternative treatments have seen limited success. Other alternative treatments may include ultra-sound, "cold laser" (low-power Class III), and LED-arrays. Results with these other alternatives treatments thus far, however, have been unimpressive and brought unremarkable patient relief.

SUMMARY

A reduction of sensory impairment (e.g., pain, soreness, tingling, burning, numbness, stiffness) in a patient's body portion (e.g., an extremity such as a leg, an arm, a foot, a hand, buttocks, etc.) associated with, e.g., peripheral neuropathy, may be treated with the use of therapeutic lasers, particularly Class IV therapeutic lasers. It has been discovered that therapeutic lasers, particularly Class IV therapeutic lasers, can be used effectively and consistently in the methods and systems described herein for reduction of sensory and/or vascular impairment.

One exemplary embodiment of a method of reducing sensory impairment in a subject's extremity includes exposing selected tissue in proximity to a selected nerve root to photonic energy from a therapeutic laser apparatus at a power of at least 6.5 Watts and exposing selected tissue of an affected extremity in proximity to a nerve extending from the selected nerve root to photonic energy from a therapeutic laser apparatus at a power of at least 5.5 Watts.

In one or more embodiments of the exemplary method, the method may include one or more of the following: exposing selected tissue in proximity to a selected nerve root to photonic energy occurs for at least 1 minute; exposing selected tissue in proximity to a selected nerve root to photonic energy occurs for no greater than 105 minutes; exposing selected tissue of an affected extremity in proximity to a nerve extending from the selected nerve root to photonic energy occurs for at least 5 minutes; exposing selected tissue of an affected extremity in proximity to a nerve extending from the selected nerve root to photonic energy occurs for no greater than 20 minutes; exposing the selected tissue for a period of time sufficient to deliver a total dosage of at least 7000 Joules to the selected tissue; and exposing the selected tissue for a period of time sufficient to deliver a total dosage of at least 9000 Joules to the selected tissue.

Further, in one or more embodiments of the exemplary method, the exposing steps may occur in a first treatment in a series of treatments occurring over a period of days or weeks. For example, the subsequent treatments may include exposing the selected tissue in proximity to the selected nerve root to photonic energy from a therapeutic laser apparatus at a power of at least 6.5 Watts, the subsequent treatments may include exposing the selected tissue of an affected extremity in proximity to a nerve extending from the selected nerve root to photonic energy from a therapeutic laser apparatus at a power of at least 5.5 Watts; the subsequent treatments may include exposing the selected tissue in proximity to the selected nerve root to photonic energy from a therapeutic laser apparatus at a power of less than 6.5 Watts; and/or the subsequent treatments may include exposing the selected tissue of an affected extremity in proximity to a nerve extending from the selected nerve root to photonic energy from a therapeutic laser apparatus at a power of less than 5.5 Watts.

Further, in one or more embodiments of the method, exposing selected tissue in proximity to a selected nerve root to photonic energy from a Class IV therapeutic laser apparatus at a power of at least 6.5 Watts may occur before exposing selected tissue of an affected extremity in proximity to a nerve extending from the selected nerve root to photonic energy from a therapeutic laser apparatus at a power of at least 5.5 Watts.

Further, in one or more embodiments of the exemplary method, exposing selected tissue may occur bilaterally; the sensory impairment may be associated with peripheral neuropathy; and/or the therapeutic laser may be a Class IV therapeutic laser apparatus.

Another exemplary method of reducing sensory impairment in a subject's extremity may include evaluating the sensory impairment; identifying one or more nerves and nerve roots that are associated with, or suspected of being associated with, the sensory impairment; exposing selected tissue in proximity to the one or more nerve roots to photonic energy from a therapeutic laser apparatus at a power of at least 6.5 Watts for at least 1 minute; and exposing selected tissue of an affected extremity in proximity to the one or more nerves extending from the selected nerve roots to photonic energy from a therapeutic laser apparatus at a power of at least 5.5 Watts for at least 1 minute (e.g., wherein the exposing steps provide at least 7000 Joules of total energy to the subject).

Still another exemplary method of reducing sensory impairment in a subject's extremity may include evaluating the sensory impairment; identifying one or more nerves and nerve roots that are associated with, or suspected of being associated with, the sensory impairment; exposing selected tissue in proximity to the one or more nerve roots to photonic energy from a therapeutic laser apparatus at a power of at least 6.5 Watts for at least 1 minute; and exposing selected tissue of an affected extremity in proximity to the one or more nerves extending from the selected nerve roots to photonic energy from a therapeutic laser apparatus at a power of at least 5.5 Watts for at least 1 minute (e.g., wherein the exposing steps in a first treatment provide at least 7000 Joules of total energy to the subject). The method may further include repeating the exposing steps in one or more subsequent treatments until at least one symptom of the sensory impairment is reduced.

One embodiment of a computer-implemented method for use in treating sensory impairment in one or more body portions of a patient may include providing data indicative of damage at different damage regions of at least one body portion of the one or more body portions and generating, using a computer processor, treatment information for treating sensory impairment in the at least one body portion using photonic energy based on the data indicative of damage.

One embodiment of a computer program for use in conjunction with a computer processor to generate treatment information for one or more body portions of a patient may be operable when used with the computer processor to receive data indicative of damage at different damage regions of at least one body portion of the one or more body portions and generate, using a computer processor, treatment information for treating at least one of sensory impairment and vascular impairment in the at least one body portion using photonic energy from a therapeutic laser based on the data indicative of damage.

In one or more embodiments of the exemplary computer-implemented method or computer program, the treatment information may include at least one treatment definition. The at least one treatment definition may include one or more treatment regions of the patient to be exposed to photonic energy to treat the at least one body portion and/or a time period of exposure to photonic energy for each of the one or more treatment regions.

Further, in one or more embodiments of the exemplary computer-implemented method or computer program, providing data indicative of damage may include collecting subjective data from the patient indicative of damage at different damage regions of the at least one body portion and/or providing data indicative of damage may include performing objective testing on the at least one body portion resulting in objective measurement data indicative of damage at different damage regions of the at least one body portion. In at least one embodiment, the method or computer program may further include collecting subjective data indicative of restoration symptoms at the different damage regions of the at least one body portion of the one or more body portions.

Still further, in one or more embodiments of the exemplary computer-implemented method or computer program, the one or more body portions may include one or more extremities of the patient, and providing data indicative of damage may include collecting data indicative of damage at different damage regions of at least one extremity of the one or more extremities (e.g., the different damage regions of the at least one extremity may be consecutively located along the at least one extremity from the patient's torso to a distal end of the at least one extremity). Further, generating treatment information in such an exemplary method may include generating, using a computer processor, treatment information for treating sensory impairment in the at least one extremity using photonic energy based on the data indicative of damage. In at least one embodiment, the method or computer program may include generating, using a computer processor, treatment information for treating the restoration symptoms based on the subjective data indicative of restoration symptoms.

Yet further, in one or more embodiments of the exemplary computer-implemented method or computer program, the method or computer program may further include: controlling, using a computer processor, delivery of photonic energy to the patient to treat the at least one body portion based on the treatment information, generating treatment information may include generating a treatment plan (e.g., a treatment plan that is generated by determining a number of photonic energy treatments based on the data indicative of damage and determining a time period per photonic energy treatment based on the data indicative of damage); and/or providing data indicative of damage may include providing data acquired during one or more previous treatments of the at least one body portion. Still further, in one or more embodiments of the exemplary computer-implemented method or computer program, the method or computer program may further include displaying treatment information to a therapist delivering photonic energy using a therapeutic laser.

Another exemplary computer-implemented method for use in treating sensory impairment in one or more body portions of a patient may include providing data indicative of damage at different damage regions of at least one body portion of the one or more body portions (e.g., collecting subjective data from the patient indicative of damage at different damage regions of the at least one body portion, performing objective testing on the at least one body portion resulting in objective measurement data indicative of damage at different damage regions of the at least one body portion, providing data acquired during one or more previous treatments of the at least one body portion, etc.). The exemplary method may further include generating, using a computer processor, treatment information for treating sensory impairment in the at least one body portion using photonic energy from a therapeutic laser based on the data indicative of damage and controlling, using a computer processor, delivery of photonic energy to the patient to treat the at least one body portion based on the treatment information. In at least one embodiment, the exemplary methods and systems described herein may further include obtaining approval of the treatment information from a practitioner prior to delivering photonic energy.

In one or more embodiments of the exemplary methods and systems described herein, the treatment information may include at least one treatment definition and the at least one treatment definition may include one or more treatment regions of the patient to be exposed to photonic energy to treat the at least one body portion. Further, the at least one treatment definition may further include a time period of exposure to photonic energy for each of the one or more treatment regions. Still further, the treatment information may include at least one treatment definition and the at least one treatment definition may include a treatment power of the photonic energy for the at least one body portion.

In one or more embodiments of the exemplary methods and systems described herein, the one or more body portions may include one or more extremities of the patient and providing data indicative of damage may include collecting data indicative of damage at different damage regions of at least one extremity of the one or more extremities. Further, the different damage regions of the at least one extremity may be consecutively located along the at least one extremity from the patient's torso to a distal end of the at least one extremity. Still further, generating treatment information may include generating, using a computer processor, treatment information for treating sensory impairment in the at least one extremity using photonic energy based on the data indicative of damage. In one or more embodiments of the exemplary methods herein, the exemplary methods may further include displaying treatment information to a therapist delivering photonic energy using a therapeutic laser.

An exemplary treatment system for use in treating sensory impairment in one or more body portions of a patient may include a local system and a therapy system. The local system may include a computer processor and may be configured to receive data indicative of damage at different damage regions of at least one body portion of the one or more body portions. The local system may be further configured to generate treatment information for treating sensory impairment in the at least one body portion using photonic energy based on the data indicative of damage. The therapy system may be operatively coupled to the local system and may include a therapeutic laser apparatus configured to deliver photonic energy to the patient to treat the at least one body portion. The therapy system may be configured to receive the treatment information from the local system for use in performing sensory impairment treatment (e.g., to control delivery of photonic energy from the therapeutic laser apparatus to the patient based on the treatment information, to display the treatment information to a therapist delivering photonic energy using the therapeutic laser treatment apparatus, etc.).

In one or more embodiments of exemplary systems described herein, the local system may be further configured to generate treatment information for treating sensory impairment in at least one extremity using photonic energy from the therapeutic laser treatment apparatus based on the data indicative of damage at different damage regions of the at least one extremity.

Further, in one or more embodiments of exemplary systems described herein, the local system may be further configured to obtain approval of the treatment information from a practitioner before allowing delivery of photonic energy from the therapeutic laser treatment apparatus to the patient based on the treatment information. Still further, in one or more embodiments of exemplary systems described herein, the treatment system may further include a practitioner system operatively coupled to the local system and configured to receive the treatment information from the local system. The practitioner system may include a display apparatus configured to display the treatment information and to prompt a practitioner to approve the treatment information, and an input interface configured to receive input (e.g., approval of the treatment information) from the practitioner. The practitioner system may be further configured to transmit the approval of the treatment information to the local system and/or to allow the practitioner to modify the treatment information using the input interface. Further, the input interface of the practitioner system may be further configured to allow the practitioner to input data indicative of damage at different damage regions of the at least one body portion based on objective testing on the at least one body portion of the one or body portions.

And still further, in one or more embodiments of exemplary systems described herein, the therapy system may include an input interface configured to receive input from a therapist and the input may include data indicative of damage at different damage regions of the at least one body portion of the one or more body portions. Further, the therapy system may include a display apparatus configured to display the treatment information, and the treatment information may include at least one treatment definition (e.g., the at least one treatment definition may include one or more treatment regions of the patient to be exposed to photonic energy to treat the at least one body portion and/or a time period of exposure to photonic energy for each of the one or more treatment regions). Still further, the therapy system may be configured to control delivery of photonic energy by controlling a treatment power of the photonic energy to be delivered for each of one or more treatment regions based on the at least one treatment definition.

Yet still further, the treatment system may further include a patient input system. The patient input system may include an input interface configured to receive input from the patient and the input may include data indicative of damage at different damage regions of the at least one body portion of the one or more body portions.

Another exemplary computer-implemented method of providing an interface for use in treating sensory impairment in one or more body portions of a patient may include providing a graphical user interface depicting one or more body portions of a patient (e.g., one or more extremities) and identifying different damage regions on each of the one or more body portions (e.g., the different damage regions may be consecutively located along the one or more extremities from the patient's torso to a distal end of the one or more extremities). The exemplary method may further include providing an input interface configured to allow a user (e.g., patient, therapist, practitioner, etc.) to input data indicative of damage of the different damage regions of each of the one or more body portions of the patient. The exemplary method may further include generating, using a computer processor, treatment information for treating sensory impairment in the one or more body portions using photonic energy based on the data indicative of damage.

In one or more exemplary methods described herein, providing an input interface configured to allow a user to input data indicative of damage may include allowing the user to input at least one sensation of a plurality of sensations (e.g., at least one of pain, tingling, numbness, burning, tightness, soreness, etc.) and at least one value for the at least one sensation for each different damage region of the one or more body portions.

Another exemplary computer system for use in treating sensory impairment in one or more body portions of a patient may include a display apparatus configured to display a graphical user interface. The graphical user interface may be configured to depict one or more body portions of a patient (e.g., one or more extremities) and identify different damage regions on each of the one or more body portions (e.g., the different damage regions may be consecutively located along the one or more extremities from the patient's torso to a distal end of the one or more extremities). The exemplary system may further include an input interface configured to allow a user to input data indicative of damage of the different damage regions of each of the one or more body portions of the patient. The exemplary system may further include a computer processor operatively coupled to the display apparatus and the input interface. The computer processor may be configured to generate treatment information for treating sensory impairment in the one or more body portions using photonic energy based on the data indicative of damage.

In one or more exemplary systems described herein, the input interface may be further configured to allow the user to input at least one sensation of a plurality of sensations (e.g., at least one of pain, tingling, numbness, heat, burning, tightness, soreness, etc.) and at least one value for the at least one sensation for each different damage region of the one or more body portions. In one or more exemplary methods and systems described herein, the time period of exposure for more distal regions of the one or more treatment regions may be greater than less distal regions of the one or more treatment regions if the data indicative of damage indicates that sensory impairment has been reduced proximally.

An exemplary method of reducing vascular impairment in a subject's extremity may include exposing selected tissue in proximity to a selected nerve root to photonic energy from a therapeutic laser apparatus (e.g., at a power of at least 6.5 Watts) and exposing selected tissue of an affected extremity in proximity to a nerve extending from the selected nerve root to photonic energy from a therapeutic laser apparatus (e.g., at a power of at least 5.5 Watts).

An exemplary computer-implemented method for use in treating vascular impairment in one or more body portions of a patient may include providing data indicative of damage at different damage regions of at least one body portion of the one or more body portions and generating, using a computer processor, treatment information for treating vascular impairment in the at least one body portion using photonic energy based on the data indicative of damage.

A "patient" herein includes humans or other mammals that are subject to sensory impairment (e.g., pain, soreness, tingling, burning, numbness, stiffness, etc.) in its one or more body portions (e.g., an extremity such as a leg, an arm, a foot, a hand, buttocks, etc.) associated, for example, with peripheral neuropathy. Other mammals may include, for example, nonhuman primates, horses, cattle, pigs, sheep, dogs, cats, etc. Preferably, the patient is a human.

The "peripheral nervous system" (PNS) includes of all parts of the nervous system, except the brain and spinal cord, which are the components of the central nervous system (CNS). The peripheral nervous system connects the central nervous system to the remainder of the body, and is the conduit through which neural signals are transmitted to and from the central nervous system.

Within the peripheral nervous system, sensory neurons transmit impulses to the CNS from sensory receptors. A system of motor neurons transmits neural signals from the CNS to effectors (glands, organs, and/or muscles). The peripheral nervous system is composed of nerve fibers that provide the cellular pathways for the various signals on which the proper operation of the nervous system relies. There are two types of neurons operating in the PNS. The first is the sensory neurons that run from the myriad of sensory receptors throughout the body. Sensory receptors provide the connection between the stimulus such as touch, heat, cold, and pain and the CNS. As well, the PNS also includes motor neurons. These neurons connect the CNS to various muscles and glands throughout the body. These muscles and glands are also known as effectors, meaning they are the places where the responses to the stimuli are translated into action.

The peripheral nervous system is subdivided into two subsystems: the sensory-somatic nervous system and the autonomic nervous system. The sensory-somatic nervous system is the sensory gateway between the environment outside of the body and the central nervous system. Responses tend to be conscious. The sensory nervous system includes twelve pairs of cranial nerves and thirty-one pairs of spinal nerves. Some of these cranial nerve pairs are exclusively sensory neurons such as the pairs involved in smell, vision, hearing, and balance. Other pairs are strictly made up of motor neurons, such as those involved in the movement of the eyeballs, swallowing, and movement of the head and shoulders. Still other pairs include a sensory and a motor neuron working in tandem such as those involved in taste and other aspects of swallowing. All thirty-one of the spinal neuron pairs are mixed: they contain both sensory and motor neurons. This allows the spinal neurons to properly function as the conduit of transmission of the signals of the stimuli and the subsequent response.

The autonomic nervous system (ANS) includes three subsystems: the sympathetic nervous system, the parasympathetic nervous system, and the enteric nervous system. The ANS regulates the activities of cardiac muscle, smooth muscle, endocrine glands, and exocrine glands. The ANS functions involuntarily (e.g., reflexively) in an automatic manner without conscious control. The ANS achieves this control via two divisions of the ANS, the sympathetic nervous system and the parasympathetic nervous system. These systems can act to stimulate organs and tissues in opposite ways (antagonistically). For example, parasympathetic stimulation acts to decrease heart rate. In contrast, sympathetic stimulation results in an increased heart rate. The autonomic nervous system also differs from the somatic nervous system in the types of tissue innervated and controlled. The somatic nervous system regulates skeletal muscle tissue, while the ANS services smooth muscle, cardiac muscle, and glandular tissue.

The nerve fibers of the sympathetic system innervate smooth muscle, cardiac muscle, and glandular tissue. In general, stimulation via sympathetic fibers increases activity and metabolic rate. Accordingly, sympathetic system stimulation is a critical component of the fight or flight response. Parasympathetic fibers of the parasympathetic nervous system innervate smooth muscle, cardiac muscle, and glandular tissue. In general, stimulation via parasympathetic fibers slows activity and results in a lowering of metabolic rate and a concordant conservation of energy. Accordingly, the parasympathetic nervous sub-system operates to return the body to its normal levels of function following the sudden alteration by the sympathetic nervous subsystem—the so-called "rest and digest" state. Examples may include the restoration of resting heartbeat, blood pressure, pupil diameter, and flow of blood to the skin. For a graphical representation of the sympathetic and parasympathetic nervous systems, please see http://images.encyclopedia.com/utility/image.aspx?id=2799137&imagetype=Manual.

The enteric nervous system is made up of nerve fibers that supply the viscera of the body: the gastrointestinal tract, pancreas, and gallbladder.

More information about the peripheral nervous system can be found in Hoyle, Brian; Arthur, Paul. "Peripheral Nervous System." Gale Encyclopedia of Neurological Disorders, 2005 (http://www.encyclopedia.com); and http://www.vivo.colostate.edu/hbooks/pathphys/digestion/basics/gi_nervous.html.

Herein, it is possible to find a non-dermatomal pattern of sensory impairment, e.g., from the toes to the ankles, as well as a dermatomal pattern, e.g., the lateral side of the leg, overlying the pathway along which a nerve runs between the central axis (e.g., the spinal cord) and a distal innervation site (e.g., the hand and/or foot). This suggests axonopathy in addition to a problem along the path of the nerve. In anatomy, a dermatome is an area of the skin for which its sensory input to the brain is mainly supplied by one of the thirty-one major spinal nerves. The locations of these areas are well known. Thus, the sensory stimuli to the brain from the area of the skin supplied by one of these nerves is considered dermatomal. Sensory disturbances that do not correspond to a dermatomal pattern are known as non-dermatomal. If the symptoms or sensory losses are in a dermatomal pattern it indicates damage to a nerve root(s) such as a herniated disc. Non-dermatomal patterns indicate damage distal to a nerve root like a burn. An explanation and picture of nerve dermatomes can be found at http://en.wikipedia.org/wiki/Dermatome_%28anatomy%29.

In one or more embodiments, the treatment information may include non-dermatomal patterns and/or dermatomal patterns.

A "nerve root" is the base and initial segment of a nerve leaving the central nervous system as it branches off the spinal cord between the vertebrae allowing motor, sensory, and other signals to be sent to and from the extremities (e.g., to interact with the peripheral nervous system). Among others, there are cervical spine (neck) nerve roots, thoracic spine (middle back) nerve roots, lumbar spine (lower back) nerve roots, sacral (pelvic) nerve roots, and cranial (cerebrum or brainstem) nerve roots.

The phrase "selected tissue in proximity" in the context of "selected tissue in proximity to a nerve root" and "selected tissue in proximity to a nerve" refers to the skin and tissue in the area overlying and/or surrounding the cells of the nerve root or nerve. Further, the term "proximity" may be empirically determined by the practitioner bearing in mind the inverse relationship between a laser's effective power and distance from the target treatment area. For example, "proximity" can be within 1 inch or less, or 0.5 inch or less, from the nerve or nerve root.

The phrase "sensory impairment" refers to one or more unpleasant (subjectively and/or objectively determined) symptoms or sensations associated with a physical condition, such as peripheral neuropathy, including, e.g., pain (aching or shooting), soreness, tingling, burning, numbness, stiffness, lack of sensation, altered proprioception, loss of balance, coordination impairment, gait impairment, feelings of compression, diminished hot and cold sensation, phantom hot and cold sensation, muscle weakness, etc. Sensory impairment can be a loss of, or over-sensitization to, a feeling (e.g., touch)—hyposensitivity or hypersensitivity.

The phrase "vascular impairment" refers to one or more unpleasant symptoms, sensations, and/or characteristics, associated with blood circulation conditions, such as damage to the capillaries due to diabetes, including, e.g., pale skin, reddish skin, purpled skin, and/or loss of color, symptoms of claudication (e.g., fatigue, heaviness, tiredness, or cramping during activity), pain that disturbs sleep, sores or wounds that heal slowly or poorly, lower skin temperatures, poor or decreased hair and/or nail growth, chronic widespread pain, fatigue, heightened pain in response to tactile pressure (allodynia), tingling, prolonged muscle spasms, weakness, nerve pain, muscle twitching, fasciculations, functional bowel disturbances, chronic sleep disturbances, etc. Although the exemplary systems and methods disclosed herein focus on treatment of sensory impairment, the disclosure herein is not limited to the treatment of sensory impairment and further contemplates the same or similar exemplary systems and methods for use in treatment of vascular impairment (e.g., reduction of vascular impairment, angiogenesis, stimulation of tissue growth, etc.).

The phrase "reduction of sensory impairment," or "reduction of vascular impairment," refers to a lessened degree (subjectively and/or objectively determined) of one or more of the unpleasant symptoms or sensations described above (e.g., which may be due to nerve and/or tissue repair and/or growth). This can include the patient's perception of reduction of, including absence of, these unpleasant symptoms or sensations.

The term "extremity" refers to a site, which includes peripheral nerves, at any distance from the nerve root in a patient, including buttocks, legs, arms, feet, and hands. The terms "comprises" and variations thereof do not have a limiting meaning where these terms appear in the description and claims.

The terms "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "a," "an," "the," "at least one," and "one or more" are used interchangeably herein. Thus, for example, a computer system that comprises "a" display apparatus can be interpreted to mean that the computer system includes "one or more" display apparatuses.

The term "or" is generally employed herein in its usual sense including "and/or" unless the content clearly dictates otherwise. The term "and/or" means one or all of the listed elements or a combination of any two or more of the listed elements. The phrase "at least one of A and B" means A and/or B.

All numbers herein are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Also herein, the recitations of numerical ranges by endpoints include all numbers subsumed within that range and include its endpoints (e.g., 1 to 5 includes 1, 1.5, 2, 2.75, 3, 3.80, 4, 5, etc.).

The above summary of the present disclosure is not intended to describe each disclosed embodiment or every implementation of the present disclosure. The description that follows more particularly exemplifies illustrative embodiments and not limiting applications. In several places throughout the application, guidance is provided through lists of examples, which examples can be used separately or in various combinations. In each instance, the recited list serves only as a representative group and should not be interpreted as an exclusive list.

BRIEF DESCRIPTION OF THE DRAWINGS

FIG. 11B is an exemplary table for use in generating a treatment plan for a patient's sensory impairment.

FIG. 19 is a table including results for the patients that have underwent therapy using the exemplary method and system described herein.

DETAILED DESCRIPTION OF EXEMPLARY EMBODIMENTS

Figure 1:
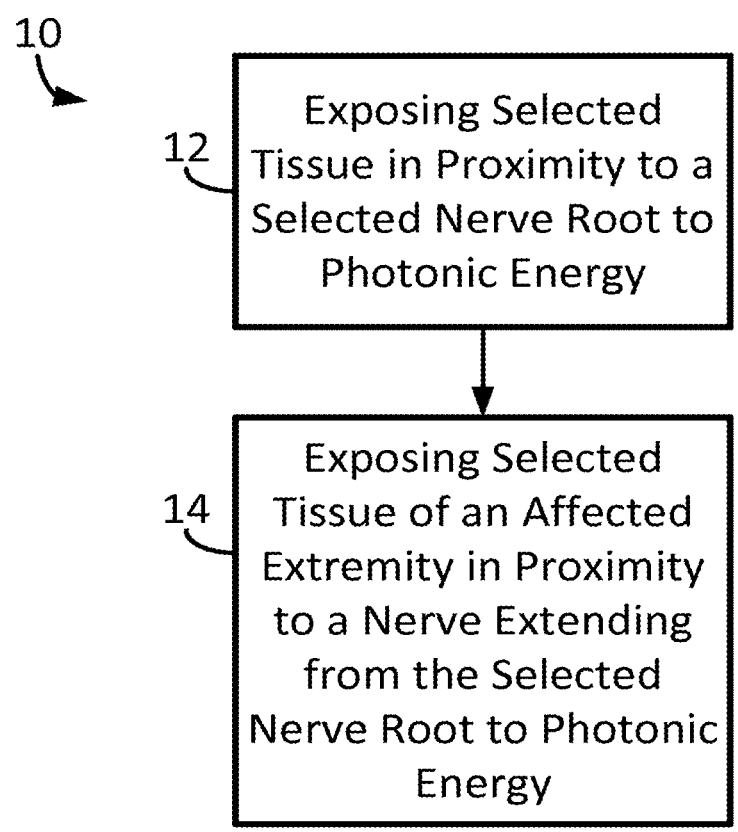
FIG. 1 is a block diagram of an exemplary method of reducing sensory impairment in a patient's extremity.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, apparatus, and systems shall be described with reference to FIGS. 1-22. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The present disclosure provides systems and methods that use, for example, therapeutic laser apparatus (e.g., Class IV therapeutic lasers) for reducing sensory impairment (e.g., pain, soreness, tingling, burning, numbness, stiffness, sense of balance/coordination/gait, whether acute, transient, or chronic) associated with, e.g., peripheral neuropathy, in a patient's body portion, e.g., extremity (e.g., leg, arm, foot, hand, buttock). Such systems and methods may involve delivering photonic energy to selected tissue (e.g., skin and underlying tissue) for a sufficient time (e.g., time per treatment, number of treatments), intensity (e.g., power in Watts applied to any particular location (e.g., point, region, area, etc.) or energy in Joules applied per treatment), and frequency (e.g., treatments per day, week, or month, and intervals between treatments) to reduce sensory and/or vascular impairment.

A Class IV laser is one that has greater power than a Class 3B laser. Specifically, a Class 3B laser is hazardous if the eye is directly exposed, but diffuse reflections from matte surfaces are not harmful. Class 3B continuous lasers emit in wavelength ranges from 315 nanometers (nm) to far infrared and are limited to power levels of 0.5 (one-half) watt. Class 3B pulsed lasers emit wavelengths between 400 and 700 nm and are limited to 30 Milliwatts (mW). Thus, lasers with higher power, broader emission spectra, and greater penetration than a Class 3B laser are considered "Class IV" lasers.

The photonic energy may be applied by a therapeutic laser (e.g., a Class IV laser). The photonic energy can be modulated, for example, by varying the wavelength, waveform, frequency, amplitude, etc. of the laser light. The energy can also be modulated by using a static or pulsing pattern (e.g., further the pulsing pattern energy can be varied). Exemplary therapeutic laser apparatus is described further herein, e.g., with respect to FIG. 7.

Methods of the present disclosure use energy, such as photonic energy (e.g., laser energy), at elevated dosages that achieve therapeutic benefit while limiting the damage to the tissue exposed to this energy, although minor irritation may occur, which can be reduced by reducing the exposure times and/or by the use of a skin cooling apparatus (e.g., the skin cooling systems produced by ZIMMER MEDIZINSYSTEMS).

In certain embodiments, systems and methods of the disclosure use non-contact treatment methods (e.g., methods that do not require pressure to be applied to the surface of the skin), using, for example, a treatment hand-piece that delivers the photonic energy (e.g., from ¼ to 3 inches away from the skin). In certain embodiments, systems and methods of the disclosure involve contact, such as massaging action, with a treatment hand-piece that delivers the photonic energy. In at least one embodiment, the contact to the skin may move some blood outside of the region of skin that is being exposed to photonic energy, e.g., so as to increase the penetration depth of the photonic energy.

One or more exemplary effective therapeutic lasers have the power capacity to deliver photonic energy with the necessary power to penetrate through the skin and underlying tissue surrounding the affected nerve cells, whether at the nerve root, in surrounding and/or adjacent tissue or skin, or at a distal location to the affected nerve root or cells, e.g., in an extremity (e.g., the leg, foot, buttock, arm, hand). In this context, "penetrate through" means, for example, to absorb, and does not include an invasive surgical procedure like cutting or injecting through the skin or tissue.

In certain embodiments, a method of the present disclosure includes reducing sensory impairment in a patient's extremity by: exposing selected tissue in proximity to a selected nerve root (of a nerve implicated in, or suspected of being, the cause of the sensory impairment) to photonic energy from a therapeutic laser (e.g., delivering photonic energy to the selected tissue) at a power of at least 6.5 Watts; and exposing selected tissue of an affected extremity in proximity to a nerve (implicated in, or suspected of being, the cause of the sensory impairment) extending from the selected nerve root to photonic energy from a therapeutic laser at a power of at least 5.5 Watts.

Typically, exposing selected tissue of an affected extremity involves translocating the photonic energy along the length of the extremity following the path of the underlying peripheral nerve axis (e.g., a path extending along the center of a peripheral nerve from a proximal end to a distal end) as close to the nerve as possible or permitted by physiological or pathological circumstances. This can be varied depending on the location of the sensory impairment. That is, treatments may include application of photonic energy to portions of the length of a nerve axis. In certain embodiments, the first or first few treatments may include applying photonic energy along the entire length of the extremity (e.g., the entire leg), and later treatments may include applying photonic energy to only a portion thereof (e.g., the lower leg from the knee to the ankle).

In certain embodiments, exposure may occur bilaterally for treatment of pain in two extremities, e.g., both legs, both arms, or both buttocks. The extremity with the worst damage is usually used to dictate the level of power and energy to apply to both extremities (e.g., both arms or both legs), although treatment definitions or protocols can be varied to allow for differential power and energy application to each extremity.

In certain embodiments, exposure may occur in an initial treatment and in a series of treatments in a therapeutic protocol. Thus, various embodiments of the present method may involve a sequential treatment, wherein a patient is typically treated at a frequency of from 1 or more times daily and/or 1 or more times each week, each for a period of from 5 minutes to 60 minutes per treatment. Transitory response may be observed after 1 treatment or 2 treatments and longer lasting response may require additional treatments, which, in chronic neuropathy, for example, may be required for a period coextensive with the remainder of the patient's life. A frequency may be, for example, from 1 treatment to 5 treatments weekly, or 1 to 3 treatments weekly, with a duration, for example, from 10 minutes to 50 minutes per treatment. The total number of treatments can range, for example, from 1 treatment to 150 treatments per year. The patient may be treated for a duration, for example, from 1 week to 12 weeks, from 2 weeks to 10 weeks, etc. The time between treatments is preferably 1 day to 2 days, although treatments can occur every other week, for example, toward the end of the treatment plan. The frequency and duration of treatment, as well as the total number of treatments, depends, in part, on the severity and duration of the sensory impairment. Periodic treatments may occur over the lifespan of a patient to address potential recurring sensory impairment and/or vascular impairment.

Systems and methods of the present disclosure can be used to reduce sensory impairment associated with peripheral neuropathy. Peripheral neuropathy is neuropathy or damage to the nerves of the peripheral nervous system. It includes neuritis, which is inflammation of a nerve, and neuralgia, which is pain due to a nerve.

It has been discovered that the effectiveness of the present disclosure as described herein can be enhanced by applying photonic energy to the nerve root of a nerve implicated in, or suspected of being, the cause of a patient's sensory impairment, in addition to applying photonic energy to the nerve implicated in, or suspected of being, the cause of a patient's sensory impairment as shown in the exemplary method 10 depicted in FIG. 1. Typically, applying photonic energy to the nerve root or nerve is carried out by exposing selected tissue in proximity to the selected nerve root or nerve to the photonic energy (block 12). In certain embodiments, for example, as shown in FIG. 1, exposing selected tissue in proximity to a selected nerve root to photonic energy occurs before exposing selected tissue of an affected extremity in proximity to a nerve extending from the selected nerve root (block 14). In certain embodiments, exposing selected tissue in proximity to a selected nerve root to photonic energy (block 12) occurs after exposing selected tissue of an affected extremity in proximity to a nerve extending from the selected nerve root (block 14).

In certain embodiments, application of photonic energy to a selected nerve root can be carried out by exposing selected tissue in proximity to the selected nerve root to photonic energy (block 12) for at least 1 minute, at least 2 minutes, at least 3 minutes, at least 4 minutes, at least 5 minutes, or even more depending on the discretion of the healthcare practitioner and the ability of the patient to tolerate potential discomfort during the treatment. In certain embodiments, application of photonic energy to a selected nerve root can be carried out by exposing selected tissue in proximity to the selected nerve root to photonic energy (block 12) for no longer than 20 minutes, no longer than 15 minutes, no longer than 10 minutes, no longer than 9 minutes, no longer than 8 minutes, no longer than 7 minutes, no longer than 6 minutes, no longer than 5 minutes, no longer than 4 minutes, no longer than 3 minutes, or even less time depending on the discretion of the healthcare practitioner and the ability of the patient to tolerate potential discomfort during the treatment.

In this context, "exposure" means application of photonic energy to the skin through a non-contact or contact manner. For example, in a non-contact methodology a treatment hand-piece can be used that delivers the photonic energy whereby the treatment hand-piece does not physically touch the skin. In a non-contact methodology, the treatment hand-piece can, for example, be held above the skin at a distance of no greater than 2 inches. In a contact methodology, for example, a treatment hand-piece that delivers the photonic energy can be used whereby the treatment hand-piece physically touches the skin, which can occur with a range of pressures, including using a massaging action.

In certain embodiments, application of photonic energy to a selected nerve can be carried out by exposing selected tissue in proximity to the selected nerve extending from the selected nerve root to photonic energy (block 14) for at least 5 minutes, at least 6 minutes, at least 7 minutes, at least 8 minutes, at least 9 minutes, at least 10 minutes, or even more depending on the discretion of the healthcare practitioner and the ability of the patient to tolerate potential discomfort during the treatment. In certain embodiments, application of photonic energy to a selected nerve can be carried out by exposing selected tissue in proximity to the selected nerve (e.g., extending from the selected nerve root) to photonic energy (block 14) for no longer than 20 minutes, no longer than 15 minutes, no longer than 10 minutes, no longer than 9 minutes, no longer than 8 minutes, no longer than 7 minutes, no longer than 6 minutes, no longer than 5 minutes, no longer than 4 minutes, no longer than 3 minutes, or even less time depending on the discretion of the healthcare practitioner and the ability of the patient to tolerate potential discomfort during the treatment.

The rate at which photonic energy (e.g., a treatment hand-piece that delivers the photonic energy) is moved over the treatment site of the selected tissue may vary, but may be at a rate that allows the photonic energy to provide an observable change in one or more of the treatment site's visual characteristics (e.g., coloration, pattern, speckling, sparkle, etc.), which may, e.g., indicate actual penetration of photonic energy through and into the tissue. For example, "speckling" of the photonic energy beam may be observed (e.g., by the healthcare practitioner) after the beam has been located over the selected tissue for a period of time. In one or more embodiments, the rate at which the photonic energy is moved along the treatment site as indicated by an observable change in one or more of its visual characteristics may be 1 inch per second or slower to the thermal tolerance of the patient.

In certain embodiments, exposure of the selected tissue occurs for a period of time sufficient to deliver a total dosage of at least 5000 Joules, at least 5500 Joules, at least 6000 Joules, at least 6500 Joules, at least 7000 Joules, at least 7500 Joules, at least 8000 Joules, at least 8500 Joules, or at least 9000 Joules, or even more energy, per treatment (including the total energy applied to both the nerve, nerve root, skin, and the surrounding tissue). Typically, no more than 25,000 Joules of energy is applied per treatment, although more could be applied (e.g., 50,000 Joules). Thus, an upper limit of applied energy is not necessarily a limitation of a treatment plan according to the present disclosure.

A treatment plan can include a series of treatments occurring over a period of days, weeks, or months. For example, an initial treatment includes: exposing selected tissue in proximity to a selected nerve root to photonic energy (block 12) from a therapeutic laser (preferably, a Class IV therapeutic laser) at a power of at least 6.5 Watts; and exposing selected tissue of an affected extremity in proximity to a nerve extending from the selected nerve root to photonic energy (block 14) from a therapeutic laser (preferably, a Class IV therapeutic laser) at a power of at least 5.5 Watts. In certain embodiments, in subsequent treatments in a treatment plan, the same amount, a higher amount, or a lower amount, of power (in Watts) or energy (in Joules) can be applied to the patient. This depends, for example, on whether the initial treatment, or subsequent treatment, results in a desired level of improvement in sensory impairment, the desired rate of improvement, and the ability of the patient to tolerate discomfort during treatment.

For example, subsequent treatments can include exposing the selected tissue in proximity to the selected nerve root to photonic energy (block 12) from a therapeutic laser (preferably, a Class IV therapeutic laser) at a power of at least 6.5 Watts, at least 6.75 Watts, at least 7 Watts, at least 7.25 Watts, or at least 7.5 Watts. Alternatively, subsequent treatments can include exposing the selected tissue in proximity to the selected nerve root to photonic energy (block 12) from a therapeutic laser (preferably, a Class IV therapeutic laser) at a power of at less than 6.5 Watts, less than 6.25 Watts, less than 6 Watts, less than 5.75 Watts, or less than 5.5 Watts.

For example, subsequent treatments can include exposing the selected tissue of an affected extremity in proximity to a nerve extending from the selected nerve root to photonic energy (block 14) from a therapeutic laser (preferably, a Class IV therapeutic laser) at a power of at least 5.5 Watts, at least 5.75 Watts, at least 6 Watts, at least 6.25 Watts, at least 6.5 Watts, at least 6.75 Watts, at least 7 Watts, at least 7.25 Watts, or at least 7.5 Watts. Alternatively, subsequent treatments can include exposing the selected tissue of an affected extremity in proximity to a nerve extending from the selected nerve root to photonic energy (block 14) from a therapeutic laser (preferably, a Class IV therapeutic laser) at a power of less than 5.5 Watts, less than 5.25 Watts, less than 5 Watts, less than 4.75 Watts, less than 4.5 Watts, less than 4.25 Watts, or less than 4 Watts.

Whether it is being applied to a nerve root in an initial treatment or in subsequent treatments, certain embodiments of the method of the present disclosure typically include exposing the selected tissue in proximity to the selected nerve root to photonic energy from a therapeutic laser (preferably, a Class IV therapeutic laser) at a power of typically no less than 1 Watt. Whether it is being applied to a nerve root in an initial treatment or in subsequent treatments, certain embodiments of the method of the present disclosure typically include exposing the selected tissue in proximity to the selected nerve root to photonic energy from a therapeutic laser (preferably, a Class IV therapeutic laser) at a power of typically no more than 20 Watts.

Whether it is being applied to a nerve extending from the selected nerve root in an initial treatment or in subsequent treatments, certain embodiments of the method of the present disclosure typically include exposing the selected tissue of an affected extremity (in proximity to a nerve extending from the selected nerve root) of typically no less than 1 Watt. Whether it is being applied to a nerve extending from the selected nerve root in an initial treatment or in subsequent treatments, certain embodiments of the method of the present disclosure typically include exposing the selected tissue of an affected extremity (in proximity to a nerve extending from the selected nerve root) of typically no more than 20 Watts.

In certain embodiments described herein, the initial treatment in a treatment plan includes applying photonic energy to the nerve root of a nerve implicated in, or suspected of being, the cause of a patient's sensory impairment (by exposing the selected tissue in proximity to the selected nerve root to photonic energy), in addition to applying photonic energy to the nerve implicated in, or suspected of being, the cause of a patient's sensory impairment (by exposing the selected tissue in proximity to the nerve extending from the selected nerve root to photonic energy). Subsequent treatments, however, can include applying photonic energy to just the nerve root of a nerve implicated in, or suspected of being, the cause of a patient's sensory impairment (by exposing the selected tissue in proximity to the selected nerve root to photonic energy), or to just the nerve implicated in, or suspected of being, the cause of a patient's sensory impairment (by exposing the selected tissue in proximity to the nerve extending from the selected nerve root to photonic energy), or to both.

The surface area of exposure to photonic energy at the nerve root (the "selected tissue in proximity to a nerve root") may, for example, be at least 1 square centimeter and no more than 1000 square centimeters. The surface area of exposure to photonic energy at the nerve in an extremity may, for example, be at least 5 square centimeters and no more than 15000 square centimeters.

Treatment plans can occur in phases depending on the progression of symptoms. For example, a first treatment phase for both legs and feet may include 6 minutes at the nerve roots, 8 minutes for each leg equally divided between the upper and lower legs, and 4 minutes for each foot. As the sensory impairment in each leg is reduced with the impression of it (e.g., pain) being "driven out" of the leg through the foot, the second treatment phase may include 6 minutes at the nerve roots, 7 minutes for each leg with more time spent on the lower legs than the upper legs, and 5 minutes for each foot. As the sensory impairment in each leg is further reduced with the patient's impression of it (e.g., pain) being "driven out" (e.g., to move distally as if one were taking off a sock) of the leg through the foot, a subsequent treatment phase may include 6 minutes at the nerve roots, 4 minutes for each leg from the mid shin to the ankle, and 8 minutes for each foot. Further, if the sensory impairment becomes different, or similar, between two extremities such as, e.g., a right leg and a left leg, subsequent treatment phases may be shift more treatment time to the extremity having greater sensory impairment (e.g., more significant damage). For example, in a patient whose remaining symptoms are very mild on the dorsum of the left foot but twice as noticeable on the right foot, ⅔ of the treatment time may be shifted to the right foot while ⅓ of the treatment time may remain on the left foot.

Although not intending to be limiting, it is believed that the methods described herein may be effective because they accomplish one or more of the following: (1) creation of Adenosine triphosphate (ATP) associated with nerve conduction or the enzymatic or metabolic pathways involved in said ATP creation; (2) increase the kinetic activity of the ATP to increase its interaction with the cell membrane; (3) deliver the appropriate nutrients to the site needed for proper functioning of the nerve cell and for repair of any cellular damage; and (4) affect underlying biomechanical or metabolic dysfunction that may be contributing to the symptomatic profile.

Creation of ATP may be responsible, when it connects the receptors on the membrane of the damaged nerve cell, for "opening" that membrane and facilitating the absorption of nutrients needed for proper function and healing of that damaged cell. The ATP under consideration may be that which is created as a result of a process that begins with the excitement of photoreceptive molecules, including but not limited to, NADH or Cytochrome-C molecules, and this may be accomplished with the delivery of very specific frequencies of photonic energy to those molecules. Increasing the kinetic activity of ATP may sufficiently cause the kinetic energy of the ATP to overcome the activation energy barrier and may connect to the nerve cell membrane in an enzyme-substrate complex that enables the transfer of nutrients into the nerve cell. This stimulation may be accomplished by heating the water in surrounding tissue and, with the resulting heat transfer to ATP, increasing the kinetic energy of the ATP. Alternatively, GTP-coupled receptor systems and/or G-Protein coupled receptor systems may be implicated in the mechanism of action by which photonic energy participated in tissue repair, more specifically, repair of neurological repair.

For a laser, typically a Class IV therapeutic laser, to be effectively used in one or more embodiments of the methods and systems described herein, it is desirable and preferable for the laser to emit frequencies that are optimized to effect the excited-state reactions of photoreceptive molecules, including but not limited to, NADH or Cytochrome-C molecules needed for the production of ATP, and frequencies optimized to the absorption range of the water molecules in the surrounding tissue. Further, it is desirable and preferable for the laser to deliver these frequencies with sufficient power to penetrate tissue without significant dissipation, so that adequate energy is delivered at the needed site of damage. Specifically, at least in one embodiment, it is desirable and preferable that the photonic energy be delivered at a frequency, and with enough power, that will stimulate the production of ATP and cause the heat absorption of water and the concurrent stimulation of ATP, such that it will increase the number of interactions between ATP and the nerve cell membrane.

Generally, a therapeutic laser apparatus to be used in the exemplary methods and systems described herein may be any apparatus capable of delivering or emitting photonic energy at a wavelength from 500 nanometers to 1000 nanometers at a power from 0.5 Watts to 30 Watts. Further, the therapeutic laser apparatus may be capable of delivering photonic energy at one or more fixed and/or selectable wavelengths either simultaneously or separately (e.g., 800 nanometers, 970 nanometers, etc.). Still further, the therapeutic laser apparatus may also be capable of delivering pulsed photonic energy in a frequency range, e.g., from 0.5 Hertz to 40,000 Hertz. In at least one embodiment, each of the following parameters of the therapeutic laser may be adjustable, e.g., by a therapist or a control system (e.g., a local system 130 as described herein with reference to FIGS. 6-7): power, wavelength, time, duty cycle, frequency, energy, average power, focal length, etc. Further, the therapeutic laser apparatus may also be capable of delivering collimated and/or divergent photonic energy. Also, the therapeutic laser apparatus may also be capable delivering photonic energy having an output spot size of 0.25 square centimeters to 10 square centimeters.

Methods of the present disclosure involve a "reduction of sensory impairment," which refers to a lessened degree of one or more unpleasant symptoms in one or more of a patient's extremities, including, for example, pain (aching or shooting), soreness, tingling, burning, numbness, stiffness, lack of sensation, altered proprioception, loss of balance, coordination impairment, feelings of compression, diminished hot and cold sensation, phantom hot and cold sensation, muscle weakness, etc. Such unpleasant symptoms are often associated with a physical condition such as peripheral neuropathy (including neuropathy associated with, or resulting from, diabetes, chemotherapy, injuries, surgery), or other conditions. Methods of the present disclosure involve evaluation of a patient's sensory impairment before treatment to assist in a healthcare practitioner's determination of treatment information (e.g., treatment plans, treatment definitions, therapeutic protocols, etc.). At various times throughout a treatment plan, the level of sensory impairment may be evaluated to evaluate the effectiveness of the treatments and to modify the treatments if necessary.

Further, the exemplary methods and systems described herein may additionally, or alternatively, be used to treat vascular impairment. For example, the exemplary methods and systems used to reduce sensory impairment may be used to reduce vascular impairment (including, e.g., the one or more unpleasant systems associated with the vascular impairment). The vascular impairment may be associated with blood circulation conditions, such as damage to the capillaries due to diabetes, etc., and may include one or more of following symptoms: pale skin, reddish skin, purple skin, or loss of color, symptoms of claudication (e.g., fatigue, heaviness, tiredness, or cramping during activity), pain that disturbs sleep, sores or wounds that heal slowly or poorly, lower skin temperatures, poor or decreased hair and/or nail growth, chronic widespread pain, fatigue, heightened pain in response to tactile pressure (allodynia), tingling, prolonged muscle spasms, weakness, nerve pain, muscle twitching, fasciculations, functional bowel disturbances, chronic sleep disturbances, etc.

Nerve damage and/or peripheral neuropathy (PN) may be acute, transient, or chronic. While the timing and duration of peripheral neuropathy may be characterized using different terms, an "acute" condition is usually associated with rapid onset and relatively short duration (minutes, hours, and/or days). In contrast, "transient" may be used to characterize conditions that are variable in both intensity and duration and/or have not reached a steady-state. "Chronic" peripheral neuropathy and/or other conditions are those that are persistent and/or long-lasting in nature, usually lasting longer than three months. The methods described herein are particularly effective for reducing sensory impairment associated with chronic conditions, such as chronic peripheral neuropathy.

Toxic agents used in therapeutic settings, such as chemotherapeutic agents, that selectively, or more strongly, affect cancerous cells than normal cells and tissues may also result in peripheral neuropathy. The methods described herein are particularly effective for reducing sensory impairment associated with peripheral neuropathy resulting from chemotherapy.

The localization of sensory impairment assists the healthcare practitioner in identifying the nerves and nerve roots to be treated. The level of general sensory impairment assists the healthcare practitioner in determining the level of power (in Watts) and energy (in Joules) to be used at any particular location, the number of treatments, and the frequency of treatments to reduce sensory impairment.

A treatment plan and/or a treatment definition can also include conventional chiropractic-like manipulations, e.g., traction manipulation, use of an activator adjustment instrument, etc. A treatment plan and/or a treatment definition can also include a focus on addressing motor function problems by increasing the range of motion of an affected area. For example, a stretching regime, typically carried out between laser treatments, can be used for added advantage if desired. Stretching can help with the soft tissue shrinkage of the connective tissues commonly associated with neuropathy and reducing fascial pain. Such stretches can be for the feet, legs, arms, hands, etc., depending on the affected extremity. A treatment plan and/or a treatment definition that includes such a focus on addressing motor function problems can also improve problems with balance and coordination.

Exemplary methods of treating (e.g., reducing) sensory impairment described herein may utilize one or more computer systems, e.g., in the generation of treatment information, in the collection of data regarding a patient's sensory impairment, in control of therapeutic equipment such as therapeutic lasers, etc. An exemplary computer system 15 depicted in FIG. 2 may be used for any of the exemplary methods and/or processes within such methods described herein.

The exemplary computer system 15 includes processing apparatus 16. The processing apparatus 16 may be configured to receive input 20 (e.g., subjective patient data, objective measurement data, cumulative patient data, etc.) and to transmit output 21 (e.g., treatment information such as treatment definitions, treatment plans, etc.) for use in treating a patient's sensory impairment and/or vascular impairment. Further, the processing apparatus 16 includes data storage 17. Data storage 17 allows for access to processing programs or routines 18 and one or more other types of data 19 that may be employed to carry out exemplary methods and/or processes for use in treating a patient's sensory impairment (e.g., some of which are shown generally in the block diagrams of FIGS. 4-5). For example, the computer system 15 may be configured to generate treatment information based on patient data and measurement data.

The computer system 15 may be operatively coupled to a therapy system 13. The therapy system 13 may be, e.g., any system operable to deliver photonic energy therapy to a patient. The computer system 15 may provide output (e.g., treatment information) to the therapy system 13. For example, the computer system 15 may output a power level, and may transmit the power level to the therapy system 13 such that the therapy system 13 delivers photonic energy at that specific power level. Further, for example, the computer system 15 may output and transmit control commands to the therapy system 13 such that the therapy system 13 is controlled by the computer system 15.

The processing programs or routines 18 may include programs or routines for performing computational mathematics, matrix mathematics, standardization algorithms, comparison algorithms, vector mathematics, or any other processing required to implement one or more exemplary methods and/or processes described herein. Data 19 may include, for example, subjective patient data, objective measurement data, cumulative patient data, treatment information such as treatment definitions and treatment plans, graphical user interfaces, results from one or more processing programs or routines employed according to the disclosure herein, or any other data that may be necessary for carrying out the one and/or more processes or methods described herein.

In one or more embodiments, the system 15 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information (e.g., treatment information). The output information may be applied as input to one or more other devices and/or methods (e.g., therapy system 13) as described herein or as would be applied in a known fashion.

The program used to implement the methods and/or processes described herein may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the system 15 may be implemented using a computer readable storage medium, configured with a computer program, where the storage medium so configured causes the computer to operate in a specific and predefined manner to perform functions described herein.

Likewise, the system 15 may be configured at a remote site (e.g., an application server) that allows access by one or more users via a remote computer apparatus (e.g., via a web browser), and allows a user to employ the functionality according to the present disclosure (e.g., user accesses a graphical user interface associated with one or more programs to process data).

The processing apparatus 16 may be, for example, any fixed or mobile computer system (e.g., a personal computer, mini computer, tablet computer, etc.). The exact configuration of the processing apparatus 16 is not limiting, and essentially any device capable of providing suitable computing capabilities and control capabilities (e.g., control of therapy apparatus, etc.) may be used. Further, various peripheral devices, such as, e.g., a computer display, mouse, touchscreen, keyboard, memory, printer, scanner, etc., are contemplated to be used in combination with the processing apparatus 16.

Further, in one or more embodiments, the output (e.g., treatment information such as treatment definitions and treatment plans, digital files, files in user-readable format, etc.) may be analyzed by a user, used by another machine that provides output based thereon, etc. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by processing apparatus 16 described herein. Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user. Generally, the methods and systems as described herein may utilize algorithms implementing mathematics to generate treatment information described herein (e.g., from subjective patient data, objective measurement data, cumulative patient data, etc.).

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

One will recognize that a graphical user interface may be used in conjunction with the embodiments described herein. The user interface may provide various features allowing for user input thereto, change of input, importation or exportation of files, or any other features that may be generally suitable for use with the processes described herein. For example, the user interface may allow default values to be used or may require entry of certain values, limits, threshold values, or other pertinent information.

The methods described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components. When implemented in software, the functionality ascribed to the systems, devices and methods described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

Figure 3:
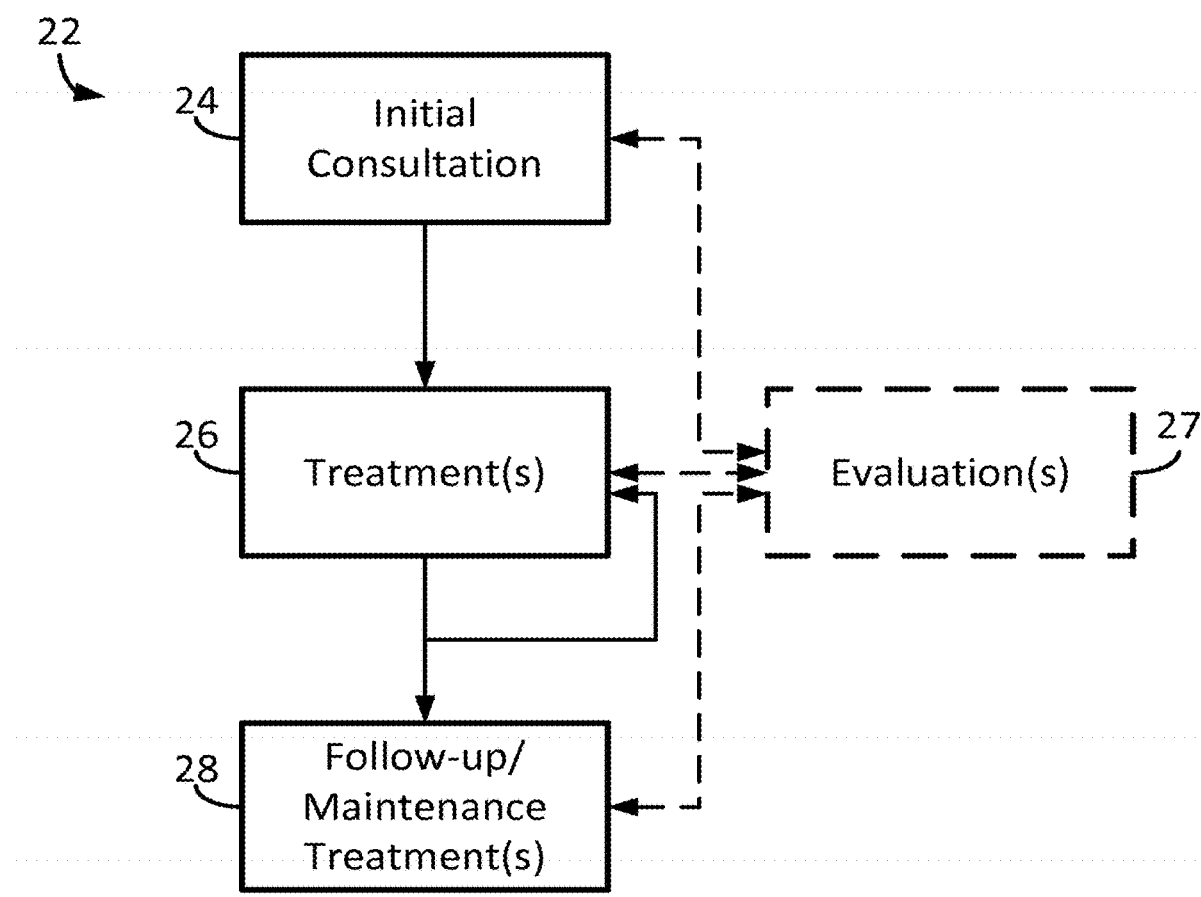
FIG. 3 is a block diagram of an exemplary method for use in treating a patient's sensory impairment.

As described herein, a patient's sensory impairment may be treated by exposure of one or more body portions of the patient to photonic energy from a therapeutic laser over a therapy period. Such therapy period may be broken into multiple processes including, e.g., an initial consultation, one or more treatments, and one or more follow-up/maintenance treatments. For example, a general method 22 for use in treating a patient's sensory impairment is shown in FIG. 3. Method 22 includes an initial consultation 24, one or more treatments 26, one or more follow-up/maintenance treatments 28, and one or more evaluations 27.

For example, an assessment of the patient's sensory impairment may be established and a treatment plan may be developed in an initial consultation 24. The treatment plan generated in the initial consultation may be based on the assessment of the patient's sensory impairment.

Figure 4:
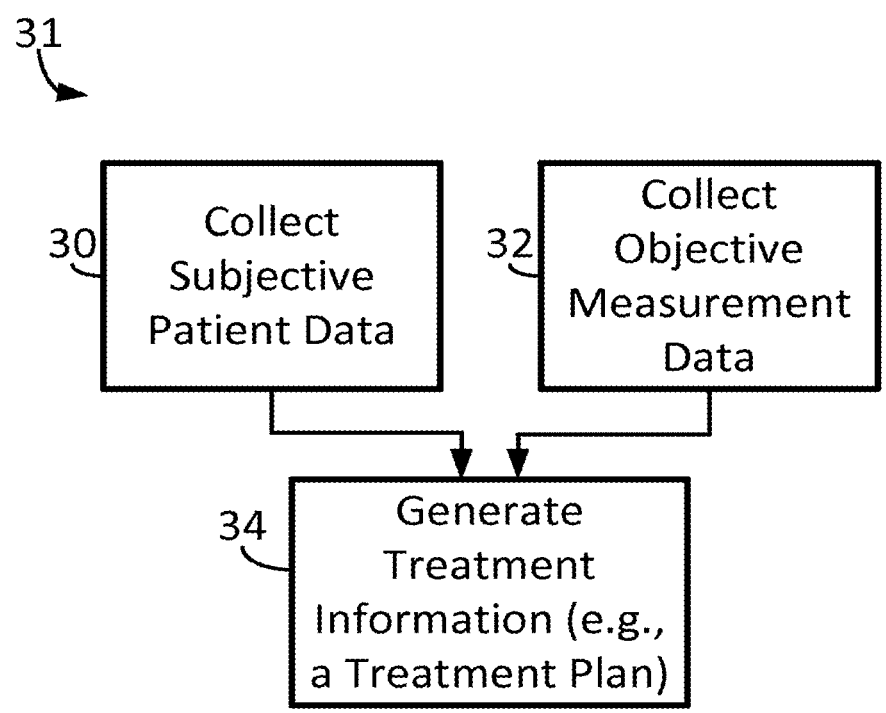
FIG. 4 is a more-detailed block diagram of the initial consultation of the exemplary method of FIG. 3.

For example, generation of a treatment plan 31, as shown in more detail in FIG. 4, may include collecting subjective patient data 30 and collecting objective measurement data 32 using one or more processes. Each of the subjective patient data and the objective measurement data is data that may be indicative of damage (e.g., sensory impairment) at different damage regions of a body portion.

As used herein, "subjective patient data" may be defined as data obtained through questioning a patient using, e.g., a form, a therapist, a graphical user interface, etc. Further, as used herein, "objective measurement data" may be defined as data obtained through one or more physical examination processes or methods designed to gather data that corresponds to a patient's sensory impairment. For example, subjective patient data may be retrieved from a patient's description of the sensory impairment or symptoms related to the sensory impairment while objective measurement data may be retrieved using physical examination of the patient by a practitioner (e.g., doctor). Further, in some cases, certain data may be considered to contribute to one or both subjective patent data and objective measurement data.

The subjective patient data may be collected 30 from patient in various ways. For example, a patient may be presented with a form that the patient may use to record or note various information with respect to their sensory impairment. Exemplary patient input forms may include graphical depictions of extremities, e.g., of a leg and an arm, respectively, and a plurality of questions to be answered for a plurality of areas (e.g., each area being labeled on the forms) of the body portion. The patient may answer each of the questions for each area by writing on the form itself, e.g., on the area itself, the side of the area, etc. In one or more embodiments, the patient may not write on the form but may use the form while fielding questions from a therapist who may enter the subjective patient data into a computer system (e.g., which may be similar to the computer system 15 described herein with reference to FIG. 2) using a graphical user interface. In at least one embodiment the patient may be presented with a graphical user interface (e.g., similar to the graphical user interfaces depicted in FIGS. 15-16) that the patient may use to record or note various information with respect to their sensory impairment.

Each of the plurality of questions that may be answered by a patient may pertain to a particular sensation that the patient may feel with respect to each labeled area of the body portion and a value (e.g., on a scale) for each particular sensation with respect to each labeled area of the body portion. For example, a patient may mark, or indicate, each labeled area with one or more of the following sensations: pain intensity, shooting pain, tingling, numbness, burning or cold sensations, soreness, tightness, heaviness in the legs, sharp pins and needles, any additional other sensations (e.g., written or marked in an "other" category), etc. Further, for each of these sensations, the patient may record a value or a ranking on a scale, such as a scale of 0 to 10, although other scales may be used. An exemplary scale of 0 to 10 for each of the sensations may be analogous to a numerical pain scale, wherein a rating of 0=none (e.g., no pain), 3=uncomfortable (e.g., mild pain that is nagging, annoying, but interferes little with activities of daily living), 5=painful (e.g., uncomfortable to dreadful pain that interferes significantly with activities of daily living), 7=agonizing pain, and 10=unbearable pain (e.g., severe pain, disabling, and unable to perform activities of daily living). In at least one embodiment, an exemplary scale of 0 to 10 is also color-coded fading from green to red wherein green is at 0 and red is at 10. In at least one embodiment, an exemplary scale may include facial expressions to help obtain an accurate measurement of pain.

In addition, for each sensation, the patient may further indicate particular sensations with an initial such as, e.g., tingling with a "T," burning heat or cold with a "B," numbness with a "N," and/or tightness with a "t." Further, the patient may also indicate whether the particular sensation has increased or decreased since the last appointment or treatment using a "+" or a "−" sign next to the sensation initial.

In other words, a patient may use a 0 to 10 scale and mark one or more regions (e.g., 6 regions) of a leg, or one or more regions (e.g., 5 regions) of the arm, for the level of sensations of pain, tingling, numbness, burning, heat, etc. Also, the type of pain (e.g., shooting), type of numbness (e.g., dull or padded), the frequency of the pain, and the relative change in the degree of sensation (e.g., T+ for more tingling than the last visit, T− for less tingling; B+ for more burning than the last visit, B− for less burning than the last visit) may also be characterized and marked on the one or more regions.

In at least one embodiment, the subjective patient data may be collected using a graphical user interface of a computer system. In essence, forms may be presented in the form of a graphical user interface of a computer system (e.g., which may be similar to the computer system 15 described herein with reference to FIG. 2 such as a tablet computer) such that the patient or a therapist interacting with the patient may use the computer system to enter the subjective patient data. Exemplary graphical user interfaces that may be used to collect subjective patient data are depicted, e.g., in FIGS. 16A-16C.

Figure 16A:
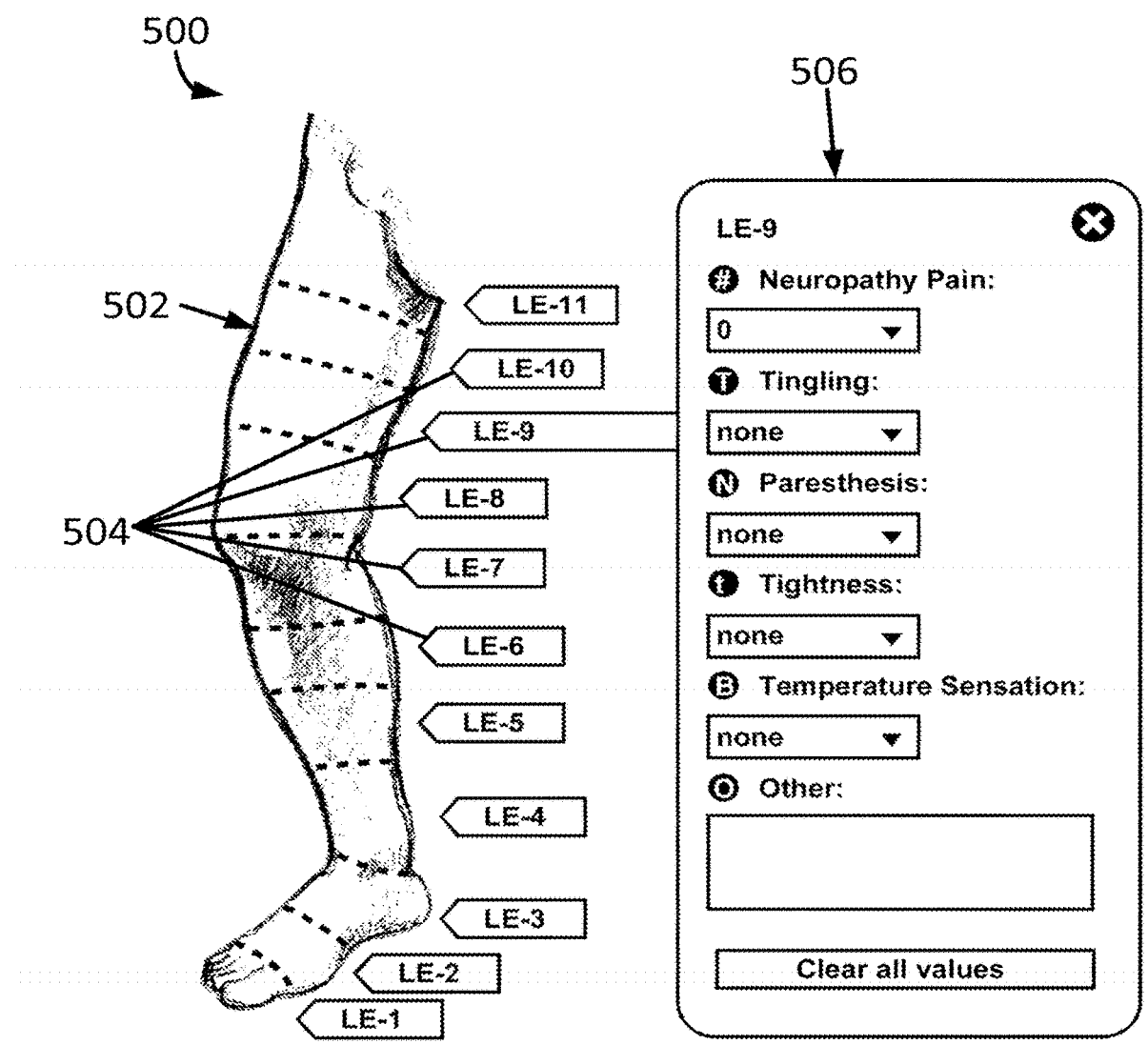
FIGS. 16A-16C are exemplary graphical user interfaces for use in inputting subjective patient data, e.g., in a treatment such as the treatment of FIG. 5.
Figure 16B:
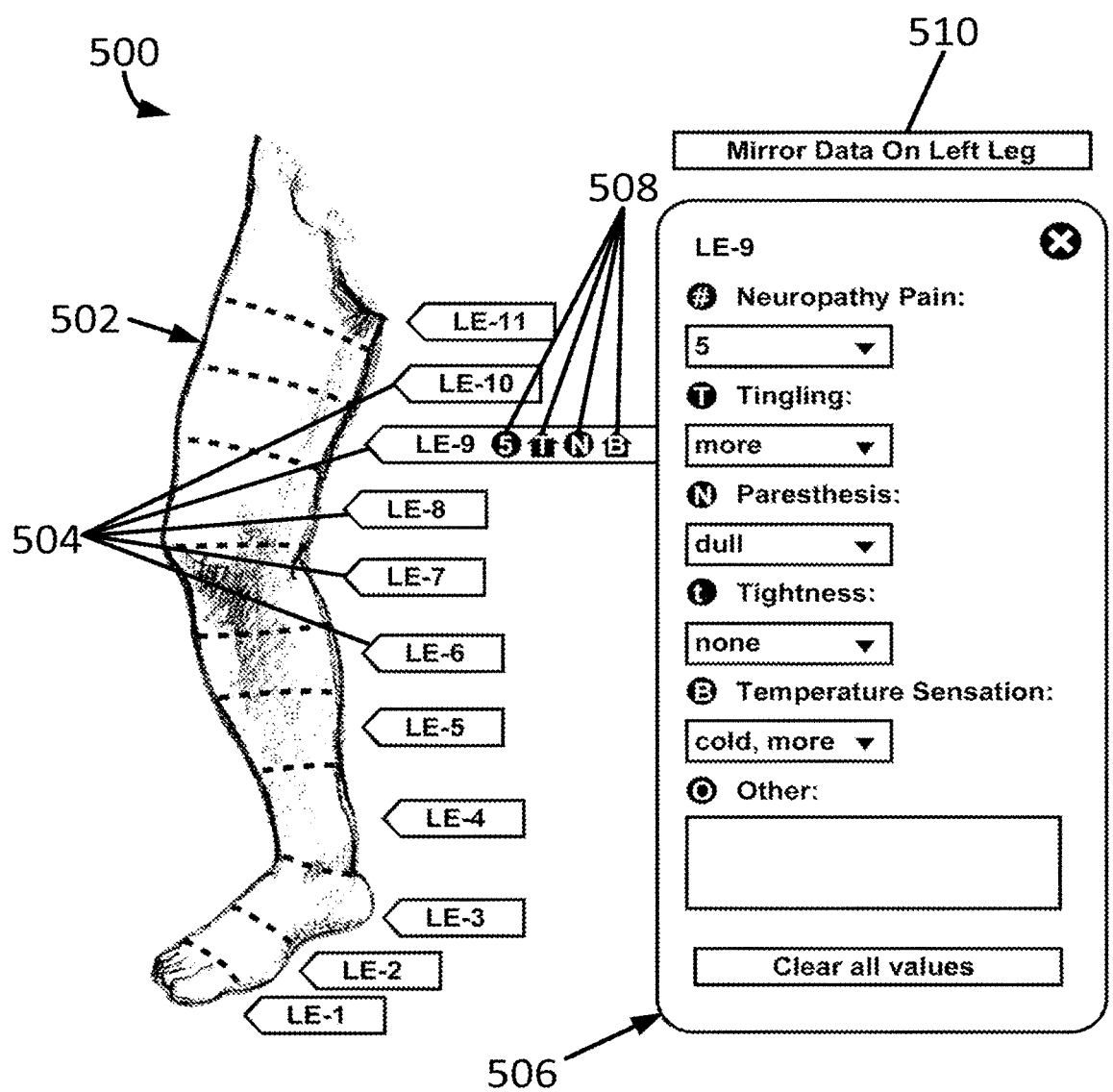
Figure 16C:
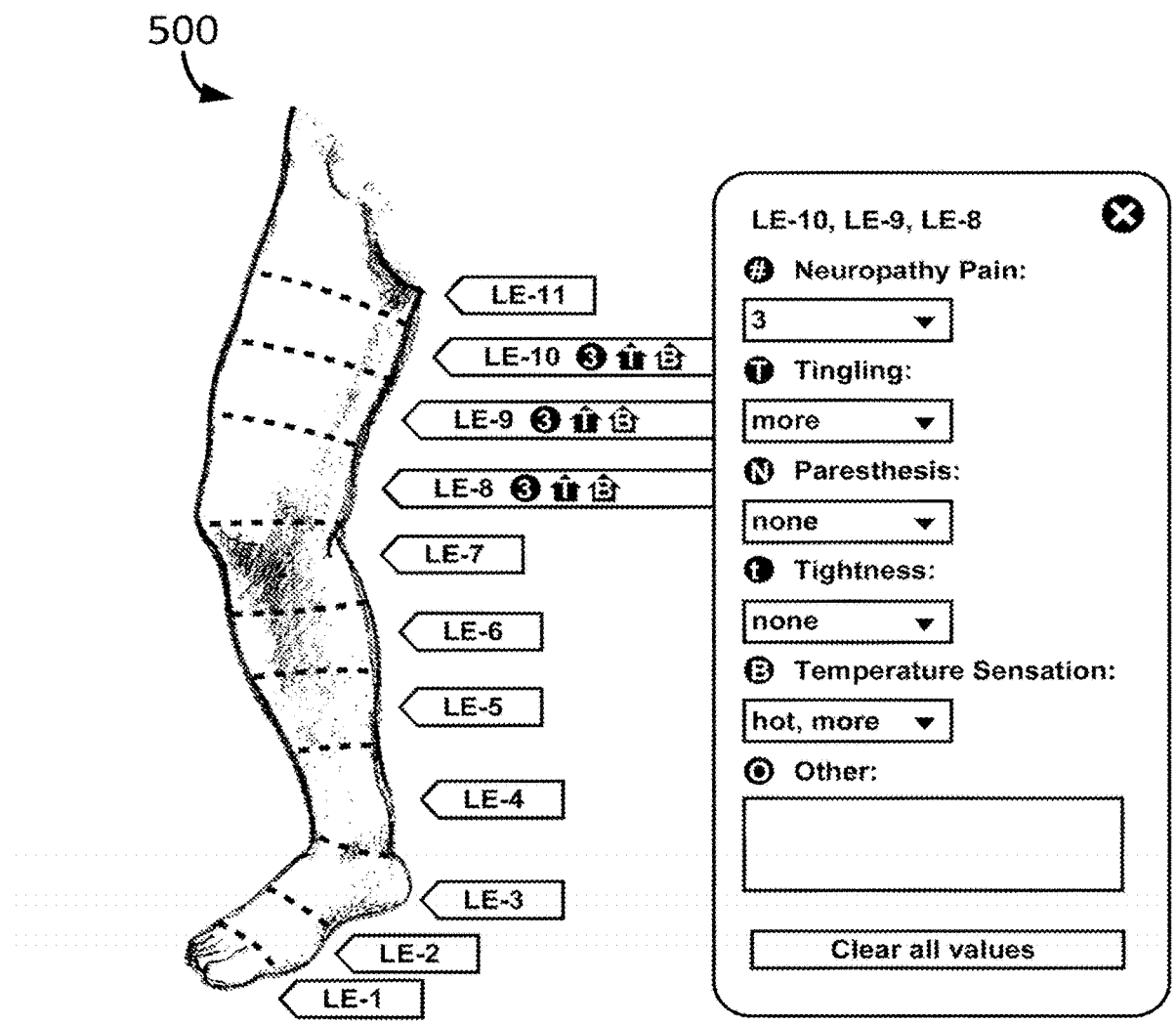

As shown in FIGS. 16A-16C, a body portion 502 of a patient may be depicted on graphical user interface 500, and multiple different damage regions 504 may be identified on the body portion 502. A user may use an input interface (e.g., touch screen, mouse, keyboard, etc.) to input data indicative of damage for each different damage region 504 of the body portion 502.

As shown, the body portion 502 is an extremity of the patient-more specifically, a leg is depicted in FIGS. 16A-16C. In other embodiments, a foot or an arm may be depicted in an exemplary input interface. Further, the damage regions 504 (e.g., LE-11 to LE-1 for the leg) for each body portion 502 are consecutively located along the extremity, e.g., from the patient's torso to a distal end of the extremity.

As shown in FIG. 16A, a user may select (e.g., click or touch) a damage region 504, which initiates the appearance of a menu 506. The user may then select a sensation of a plurality of sensations, such as, e.g., neuropathy pain, tingling, paresthesis, tightness, temperature sensation, etc. and a value for each sensation for each different damage region 504 using the menu 506. In other embodiments, the plurality of selected sensations may further include numbness, heat/burning sensation, cold/freezing sensation, etc. As shown, the menu 506 includes a "pull-down" selection function for each sensation within which a user may select the value. The value for each sensation may be, e.g., a numerical value from 0 to 10, affirmative, negative, more, less, same, yes, no, dull, padded, completely numb, none, etc. The user may select a value for each sensation for each of the damage regions 504 for the body portion 502 using the "pull-down" selection function for each sensation. After a value has been selected for a sensation, an icon 508 indicating the sensation and value may appear proximate the body portion 502 as shown in FIG. 16B.

A patient's sensations may be similar from the most proximal (e.g., nearest the torso) affected damage region 504 to the most distal end of the extremity. As such, the interface 500 may allow a user to select more than one damage region 504 to input the sensation and the value associated with the sensation at the same time. In other words, the interface 500 may allow a user to simultaneously enter one or more sensations and values associated with each sensation for more than one damage region 504, e.g., from a damage region to a more distal damage region. For example, as shown in FIG. 16C, a user has selected damage regions 504 LE-10, LE-9, and LE-8 such that the inputted sensations and values for each sensation may be inputted for each such damage region 504 LE-10, LE-9, and LE-8. In at least one embodiment (although not depicted in FIG. 16B), the interface 500 may allow a user to copy inputted sensations and associated values to each damage region 504 from the inputted damage region 504 to the most distal damage region (e.g., LE-1) (e.g., all the damage regions 504 between the damage region 504 where data was inputted and the most distal damage region 504). This function, where all values are copied down the extremity from a more proximal damage region may be referred to as "cascading" (e.g., using a "cascading" function).

Further, a patient's sensations may be similar from one body portion 502 to another corresponding body portion 502. For example, the sensations in a patient's left leg may be similar to the sensations in the patient's right leg. As such, the interface may allow a user to copy, or "mirror," the inputted sensations and the inputted values for the sensations for the damage regions from one body portion to another (e.g., from the left leg to the right leg). This function may be referred to as a "mirror" function 510 as shown in FIG. 16B.

The objective measurement data may also be collected 32 in various ways. Generally, the patient may be evaluated locally by a variety of clinical diagnostic tests, e.g., nerve conduction studies. Common tests used for localized evaluation of a patient's subjective sensory impairment include a vibratory test and a pinwheel test, as well as the Tinel's Test and the Babinski Test. The vibratory test is used to test sensory impairment to a vibrating tuning fork. The pinwheel test is used to test sensory impairment to a pinwheel (e.g., Wartenberg pinwheel). The Tinel's Test (i.e., Tinel's Sign Test) is performed by lightly tapping (percussing) over the nerve to elicit a sensation of tingling or "pins and needles" in the distribution of the nerve. It is commonly used in testing for carpal tunnel syndrome. The Babinski Test (i.e., Babinski Reflex or Babinski Sign Test) is a neurologic test based upon what the big toe does when the sole of the foot is stimulated. The Babinski reflex is obtained by stimulating the external portion (the outside) of the sole. The practitioner may begin the stimulation (e.g., using their thumb and applying firm pressure) moving from back to front starting at the heel and moving forward to the base of the toes along the outside edge of the foot. Further, skin temperature and/or coloration measurements as well as any other measurements or indicators associated with vascular impairment may also be collected and, e.g., used to generate treatment information for treating vascular impairment.

Other tests that can be used include qualitative or quantitative tests. Such tests include, for example, Semmes Weinstein test in which pressure is applied against the skin of affected areas using monofilaments of varying thicknesses, hot-versus-cold test in which sensory impairment to temperature change is evaluated, the nerve conduction velocity test (NCV) and the needle electromyogram test (EMG), both of which measure sensory impairment by evaluating the conductivity of nerves. Any one of these tests or other clinical diagnostic tests, alone or in combination, could indicate sensory impairment resulting from peripheral neuropathy.

Further, to collect objective measurement data and/or subjective patent data, a practitioner may perform measurements of the following and/or may use the following tests: tibial pulse, dorsalis pedis, compression of nerves at the Tarsal Tunnel and Fibular Heads each leg (e.g., the Tinel's Test), reflexes at the knee and Achilles tendon, presence or absence of clonus, Babinski Sign Test, arm pulses, radial pulse, Ulna pulse, Carpal and Tarsal Tunnel (e.g., the Tinel's Test), modified total neuropathy score (mTNS), balance screening test, quality of life (QOL) tests (e.g., Neuro-QOL), etc.

Figure 2:
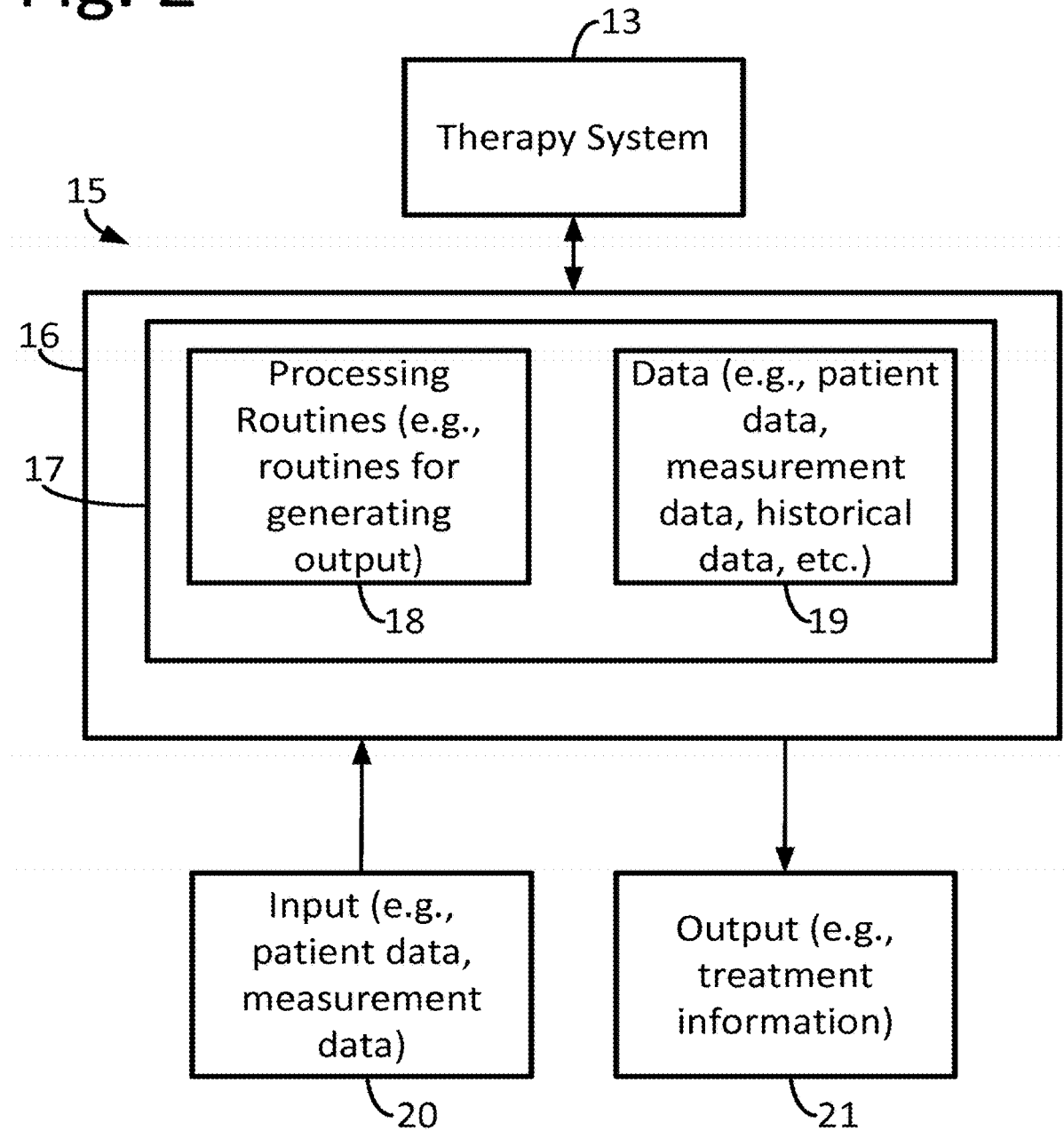
FIG. 2 is block diagram of an exemplary computer system for use in treating one or more patient's sensory impairment.
Figure 8:
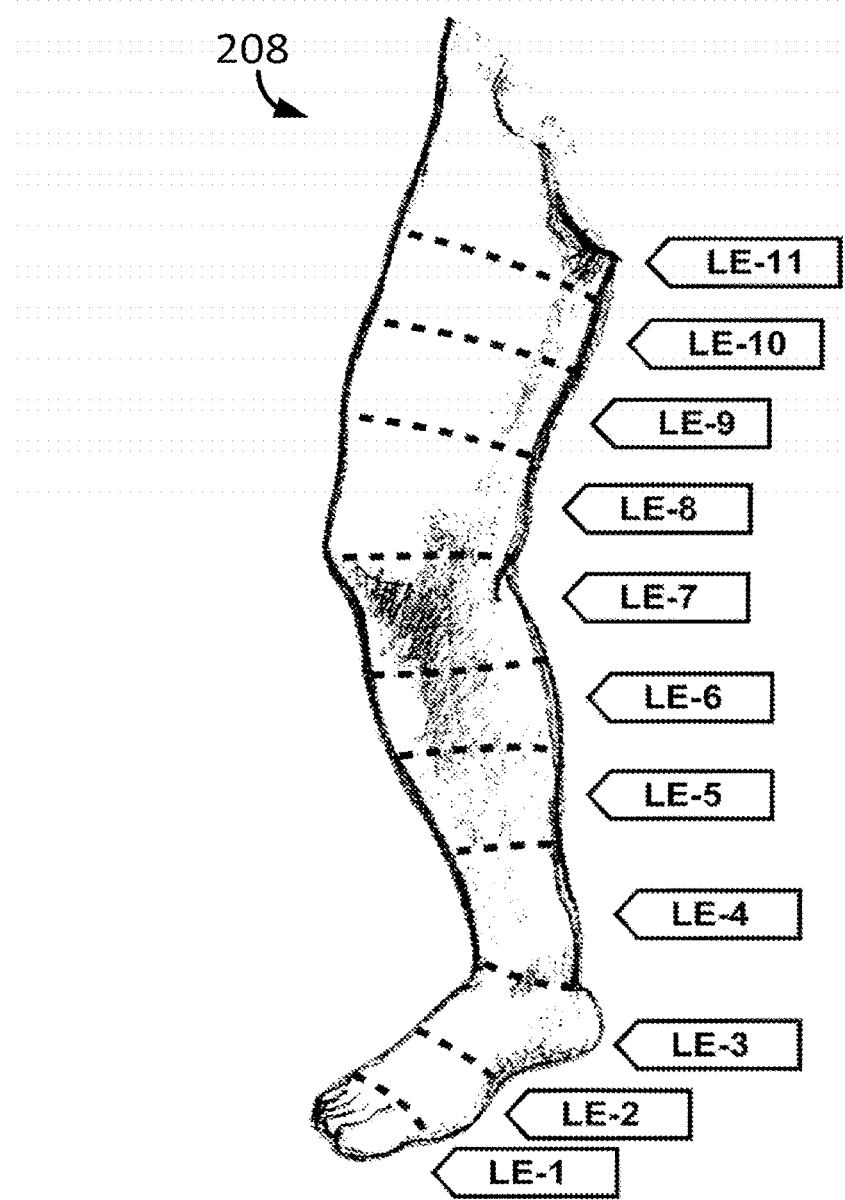
FIG. 8 is an exemplary input interface for a leg.
Figure 9:
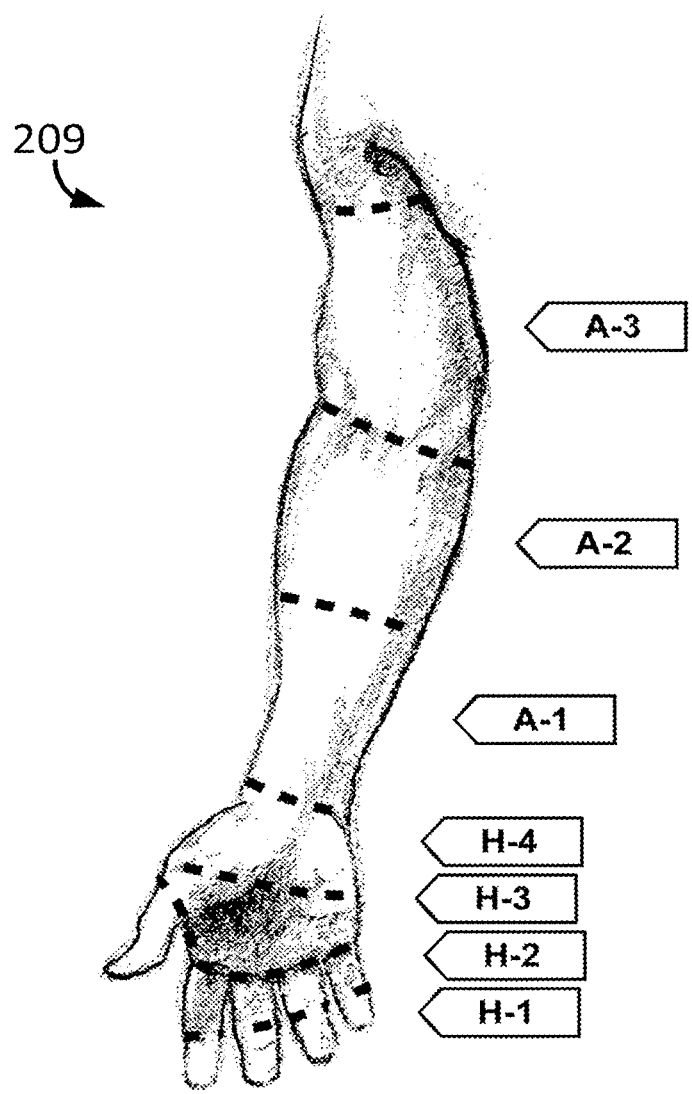
FIG. 9 is an exemplary input interface for an arm.
Figure 10:
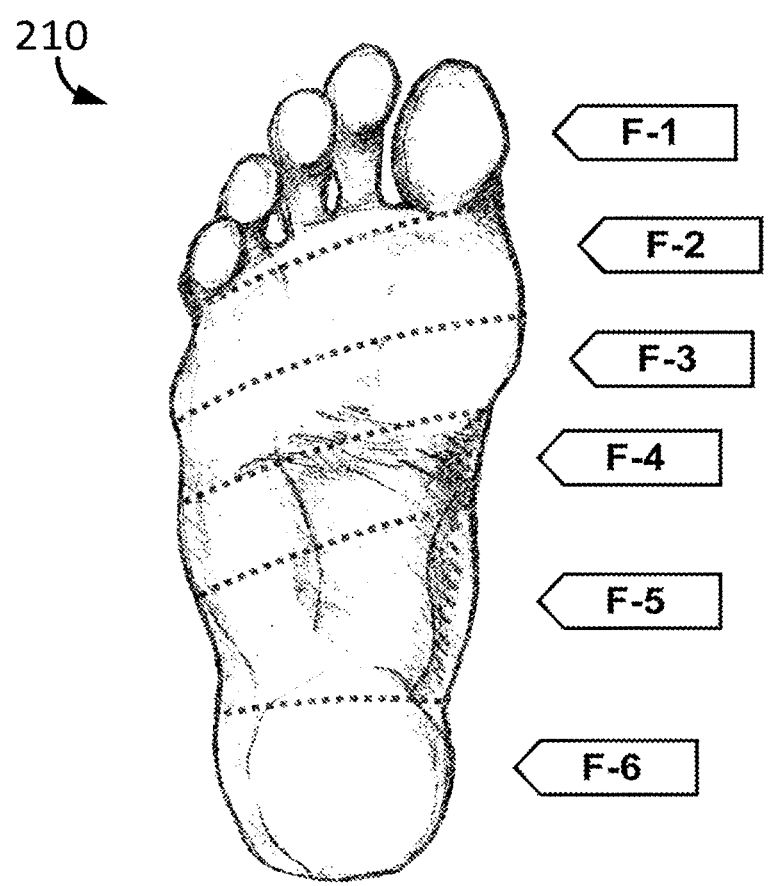
FIG. 10 is an exemplary input interface for a foot.

The objective measurement data may also be entered into a computer system, e.g., which may be similar to the computer system 15 described herein with reference to FIG. 2. For example, a practitioner may be presented with a graphical user interface of a computer system presenting various graphical depictions of body portions and may further use the computer system record or enter various objective measurement data with respect to the patient's sensory impairment. An exemplary leg input graphical user interface 208 is depicted in FIG. 8, an exemplary arm input graphical user interface 209 is depicted in FIG. 9, and an exemplary foot input graphical user interface 210 is depicted in FIG. 10. Each interface 208, 209, 210 includes graphical depictions of a leg, an arm, and a foot, respectively. Each of the leg, arm, and foot include a plurality of damage regions. The damage regions are consecutively labeled using, for example, an alphanumerical scale: Le1 to Le11 for the leg, H1 to A3 for the arm, and F1 to F6 for the foot. More specifically, the damage regions are consecutively located (and labeled) along each extremity from a patient's torso to a distal end of the extremity. Additional exemplary graphical user interfaces that may be used to collect objective measurement data are depicted, e.g., in FIGS. 15A-15D.

Figure 15A:
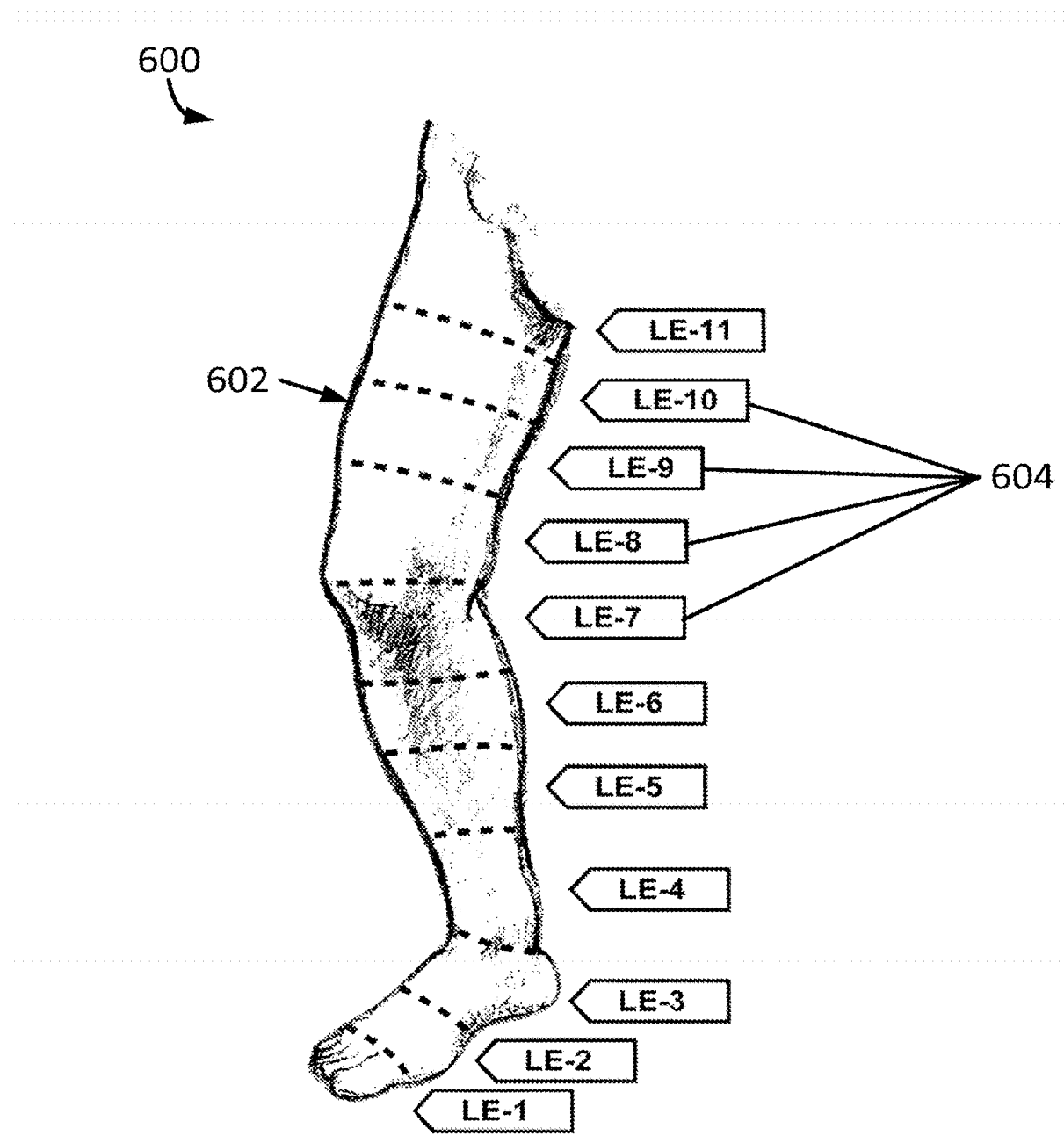
FIGS. 15A-15D are exemplary graphical user interfaces for use in inputting objective measurement data, e.g., in an initial consultation such as the initial consultation of FIG. 4, periodic reexaminations during the course of care, etc.
Figure 15B:
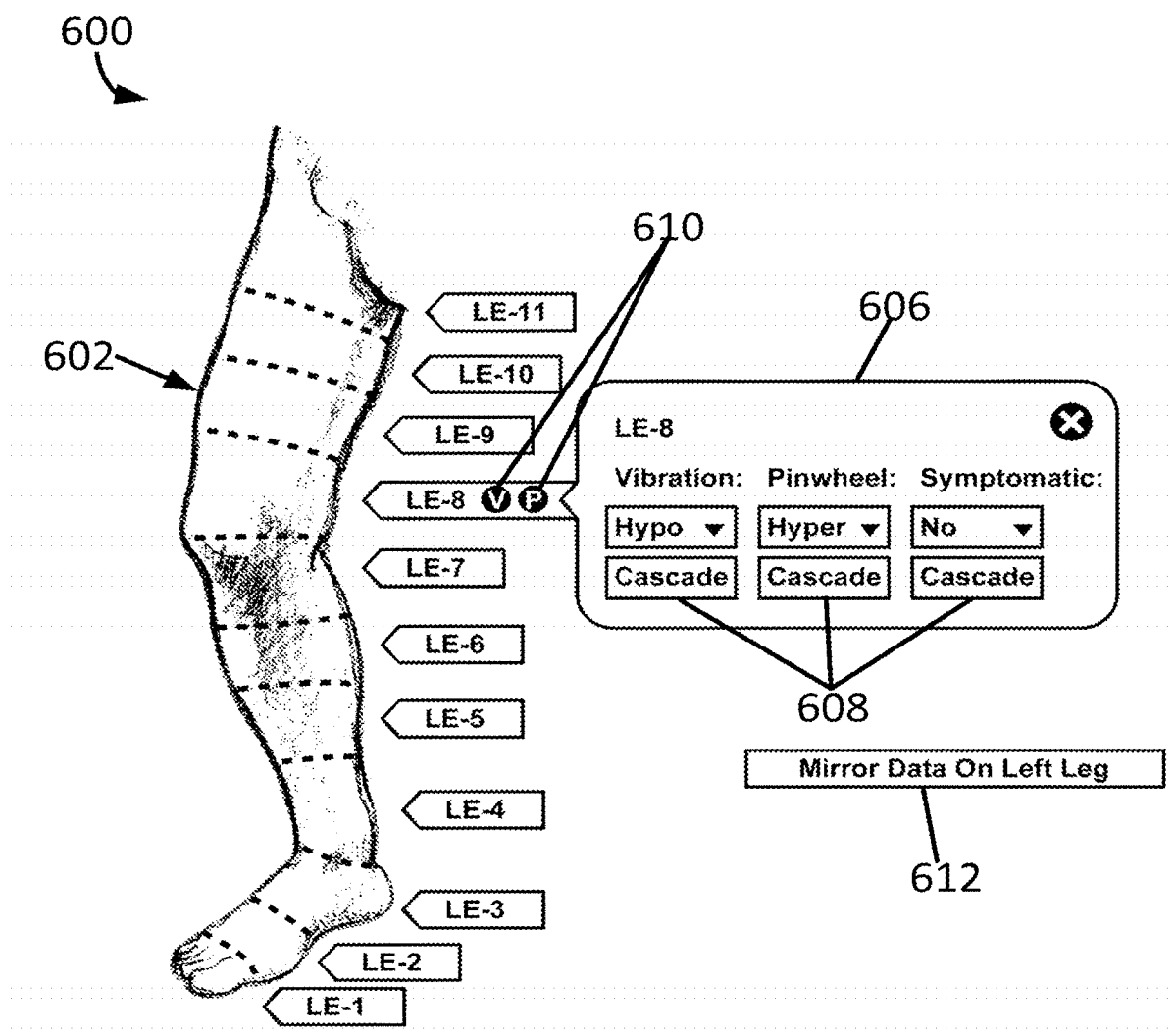

An exemplary user interface that may be used to collect/input objective measurement data may be similar to the user interface 500 that may be used to collect/input subjective patient data. For example, as shown in FIGS. 15A-15D, a body portion 602 of a patient may be depicted on graphical user interface 600, and multiple different damage regions 604 may be identified on the body portion 602. After selecting, e.g., clicking, touching, etc., a damage region 604 as shown in FIG. 15B, a menu 606 may be displayed, or appear, that allows a user to select a sensation, e.g., vibration, pinwheel, etc., and select a value to be associated with that sensation, e.g., normal, hypo, hyper, absent, etc. After a sensation and value have been selected for a damage region 604, one or more icons 610 may appear proximate the damage region 604 indicating the sensation and value. As described herein with reference to interface 500 of FIGS. 16A-16C, the sensation and the values associated with that sensation may be inputted into multiple damage regions simultaneously or copied from one damage region to multiple damage regions (e.g., "cascaded") or to another body portion (e.g., "mirrored").

Further shown in FIG. 15B is an area for indicating whether the damage region is symptomatic of peripheral neuropathy. For example, a practitioner may select a "yes" or a "no" for each damage region (e.g., indicating whether such damage region is symptomatic of peripheral neuropathy). For example, if a patient tells a practitioner that he/she has symptoms in a damage region (e.g., one or more damage regions) that are indicative of peripheral neuropathy, then the practitioner may select a "yes" value for that damage region. Such subjective symptomatic data may be used to modify, or append, certain treatment information such as, e.g., described in reference to FIG. 11A.

Figure 15C:
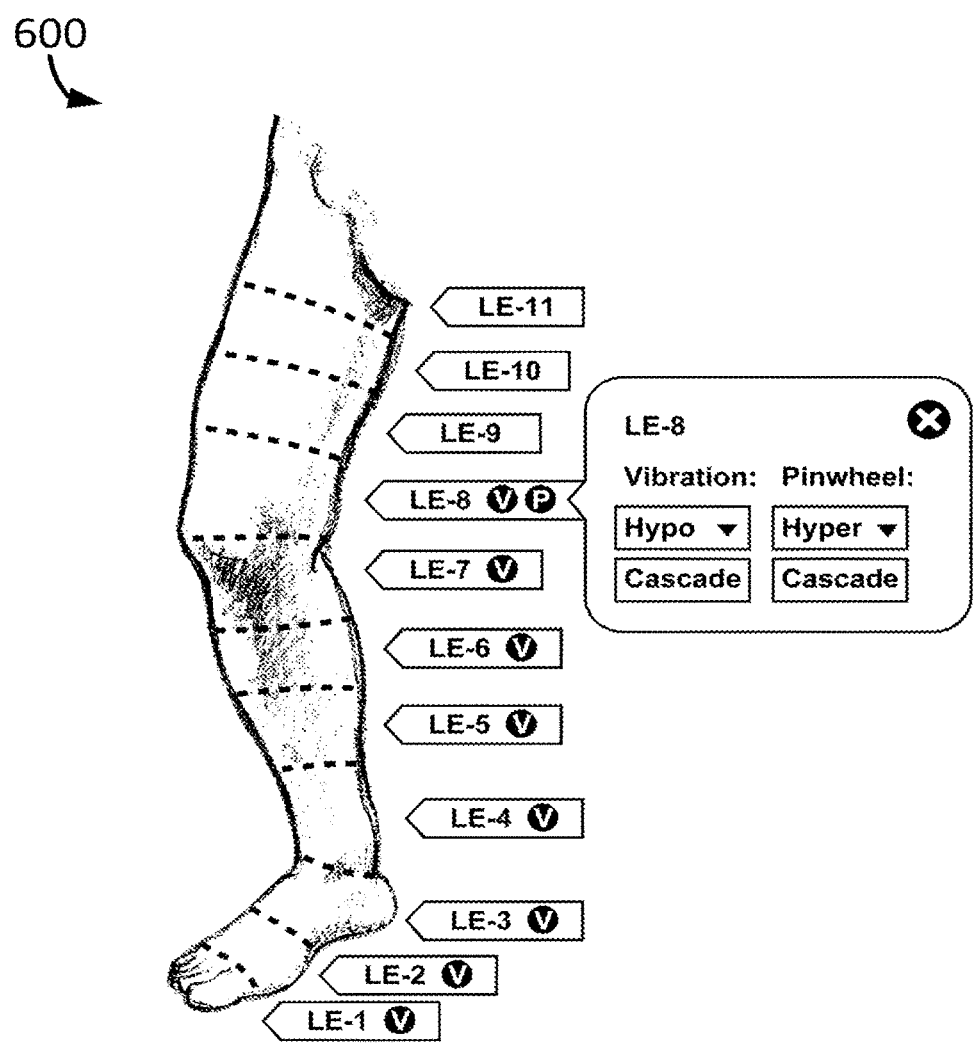
Figure 15D:
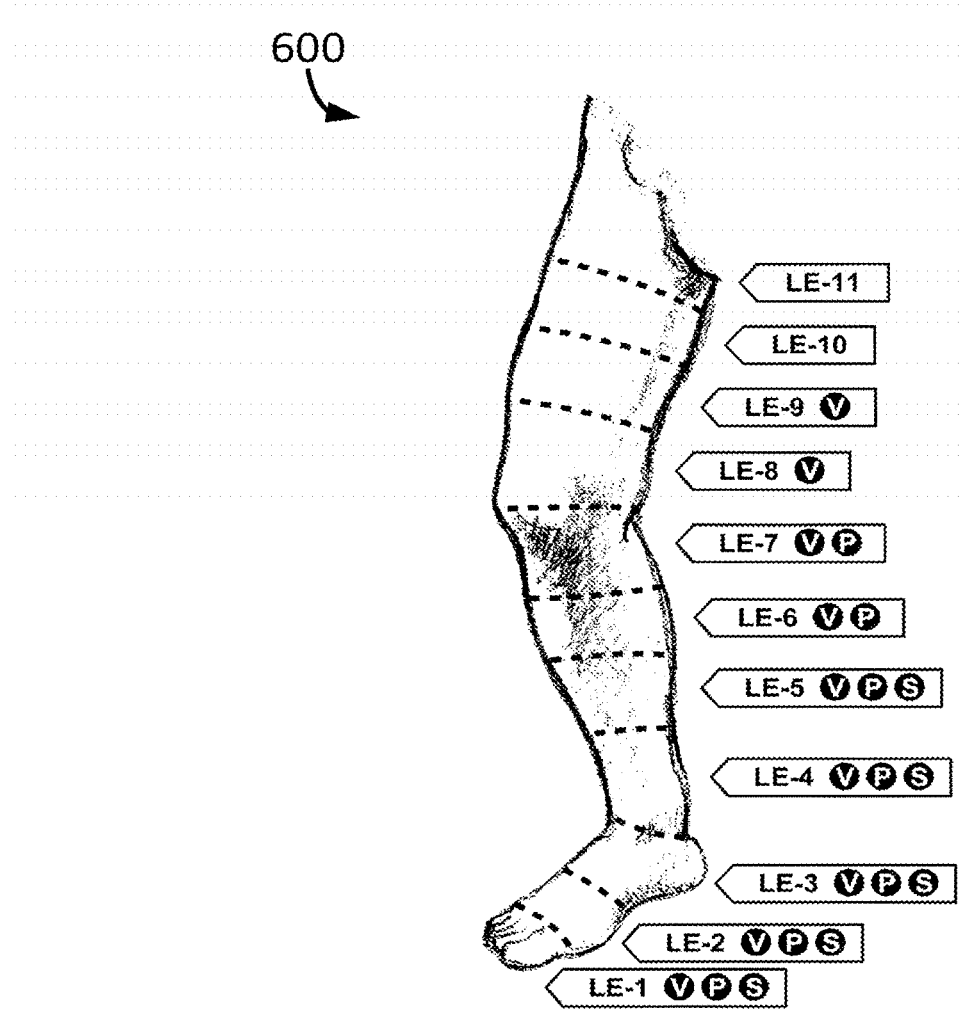

As shown in FIG. 15B, hypo was selected in the vibration sensation test and hyper was selected for the pinwheel sensation test for damage level LE-8. If a user selected the "cascade" function 608 in FIG. 15B, the remaining damage regions from damage level LE-8 to the distal end of the extremity would receive the same sensations and values as inputted at damage level LE-8. As shown in FIG. 15C, a user has selected hypo vibration and cascaded the values downwardly from LE-8. Further, if a user selects the "mirror" function 612 in FIG. 15C, the other extremity, i.e., the left leg, will receive the same sensations and values as inputted for the right leg. Additional values have been indicated in FIG. 15D.

Further, one or more temperature targets may be labeled on the graphical depictions of the leg, arm, and foot in the interfaces 208, 209, 210, which may be used to indicate one or more areas where skin surface may be measured using a temperature detector. Such temperatures may also be entered into a computer system using, e.g., the graphical user interfaces of FIGS. 8-10 and 15A-15D.

Although subjective patient data and objective measurement data are described herein separately, various tests, questions, and/or measurements may be both subjective and objective. For example, objective measurement tests may be modified by patient input, and therefore, could be considered to include subjective data. Further, although subjective patient data is referred to as being "subjective," subjective patient data may include objective data. Likewise, although objective measurement data is referred to as "objective," objective measurement data may include subjective data. In essence, although the terms subjective patient data and objective measurement are described separately herein, the use of the words subjective and objective within such terms is not meant to limit the data in any way. Further, various tests may include subjective and objective components. For example, a modified Total Neuropathy Score may include subjective questions (e.g., with respect to paresthesias (tingling)) and objective measurements (e.g., vibration).

After the subjective patient data has been collected 30 and/or the objective measurement data has been collected 32, treatment information may be generated 34. The treatment information may be generated 34 using an algorithm in a computer system, e.g., the computer system 15 described herein with reference to FIG. 2. The algorithm may use the subjective patient data and/or the objective measurement data, i.e., inputs, to generate the treatment information, i.e., the output. The treatment information generated in method 31 may include one or more of treatment plans, treatment definitions (e.g., phase treatments), and/or any other information for defining a treatment or delivery of such treatment. An exemplary treatment plan may include an estimated number of treatments (e.g., including photonic energy treatments, stretching exercises, and/or other various treatments) and an amount of time, or time period, per treatment to treat a patient's sensory impairment.

Figure 11A:
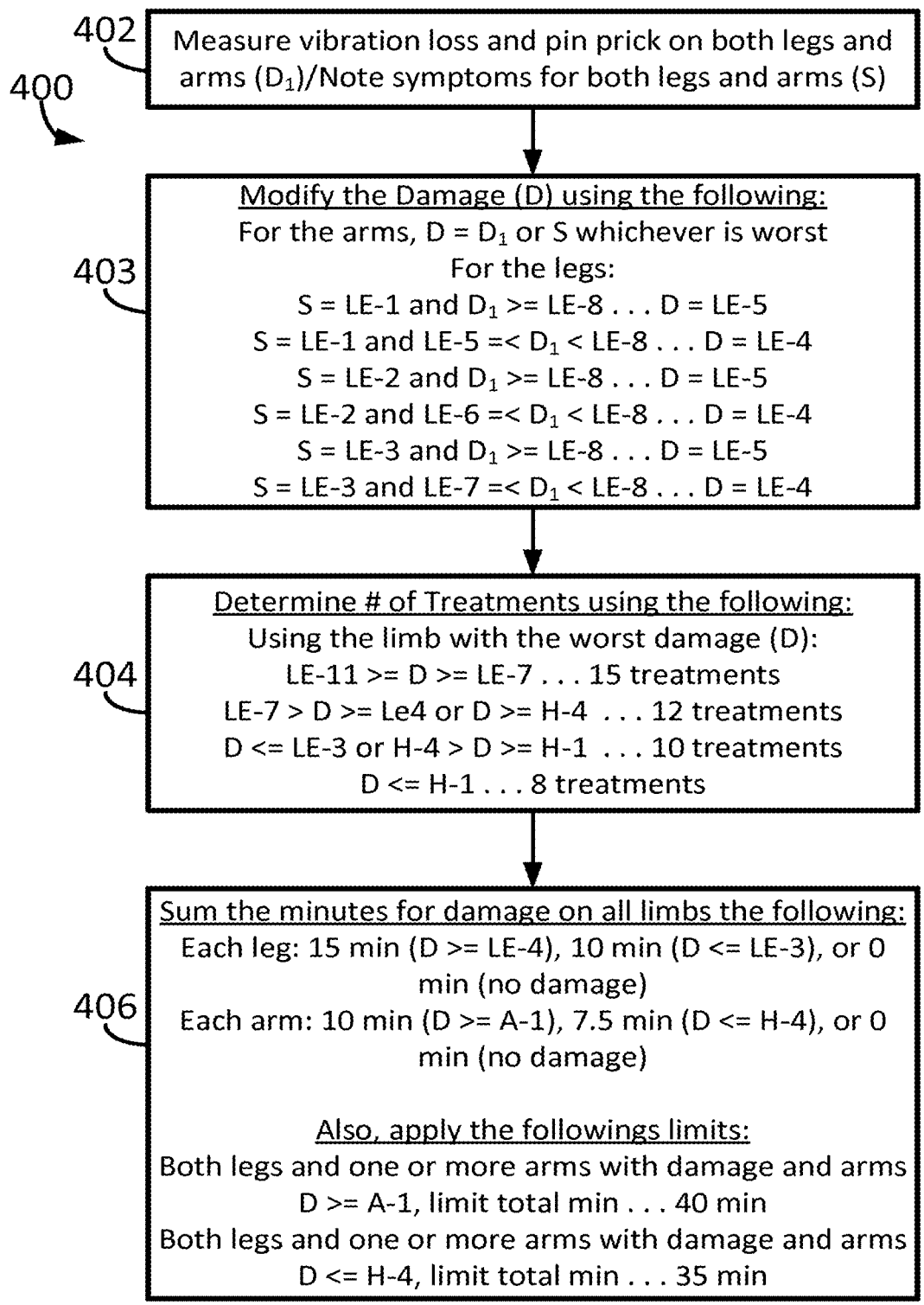
FIG. 11A is a block diagram of an exemplary method of generating a treatment plan for a patient's sensory impairment.

One exemplary method of generating a treatment plan for a patient's sensory impairment is depicted in FIG. 11A. Generally, the method 400 includes collecting subjective data and objective measurement data 402, modifying the damage level 403, determining the number of treatments for the treatment plan 404, and determining the amount of time per treatment for the treatment plan 406. As shown, collecting subjective and/or objective measurement data 402 includes collecting subjective symptomatic data (e.g., indicative of peripheral neuropathy, noting where symptomatic areas are located for the arms and legs, etc.) and measuring vibration loss and pin prick loss in the arms and legs of the patient. Although not shown, such subjective and/or objective measurement data may be inputted into a computer system, e.g., computer system 15 as described herein with reference to FIG. 2.

In certain situations, a patient may have symptoms indicative of peripheral neuropathy that do not completely correspond to the objective measurement data. In these situations, it may be beneficial to modify 403, or append, the damage determination, or worst damage (D) (e.g., determined by the objective measurement data) by the symptoms. In other words, the worst damage (D) may be modified 403 by symptomatic measurements (S). Generally, for the legs, if the symptomatic area is dramatically lower than the areas of vibration and pinprick loss, then D may be reduced. Further, for the arms, in many cases the vibration and pin prick measurements may be normal (e.g., not indicative of neuropathy), but yet the patients are still symptomatic (e.g., indicative of neuropathy)—in this case, D be increased for the arms accordingly.

For example, as shown in FIG. 11A, for the arms, D may be set to the worst (e.g., most proximal such as closest to the torso of the patient) damage ($D_1$) (e.g., measured using objective measurement techniques, etc.) or symptoms (S) indicative of neuropathy. Further, for the legs, if the symptoms (S) indicate neuropathy at LE-1 and damage ($D_1$) is measured at greater than or equal to LE-8, then D may be reduced to LE-5. If the symptoms (S) indicate neuropathy at LE-1 and damage ($D_1$) is measured at greater than or equal to LE-5 and less than LE-8, then D may be reduced to LE-4. If the symptoms (S) indicate neuropathy at LE-2 and damage ($D_1$) is measured at greater than or equal to LE-8, then D may be reduced to LE-5. If the symptoms (S) indicate neuropathy at LE-2 and damage ($D_1$) is measured at greater than or equal to LE-6 and less than LE-8, then D may be reduced to LE-4. If the symptoms (S) indicate neuropathy at LE-3 and damage ($D_1$) is measured at greater than or equal to LE-8, then D may be reduced to LE-5. If the symptoms (S) indicate neuropathy at LE-3 and damage ($D_1$) is measured at greater than or equal to LE-7 and less than LE-8, then D may be reduced to LE-4.

Determining the number of treatments for the treatment plan 404 may utilize the damage region having the most proximal (e.g., closest to the torso of the patient) damage when compared to the other body portions, which may be referred to as the "worst damage (D)". Generally, the more proximal the damage, the greater the number of treatments, which will be provided in the output or treatment plan.

For example, as shown in FIG. 11A, if any leg has damage located more proximal than LE-10 (see FIG. 8), then the treatment plan may include 17 treatments. If any leg has damage located less proximal than LE-10 but more proximal than or equal to LE-7, then the treatment plan may include 15 treatments. If any leg has damage located less proximal than LE-7 but more proximal than or equal to LE-4 or any arm has damage located less proximal than or equal to H-4, the treatment plan may include 12 treatments. If any leg has damage located less proximal than or equal LE-3 or any arm has damage located less proximal than H-4 but more proximal than or equal to H-1, then the treatment plan may include 10 treatments. If any arm has damage located less proximal than or equal to H-1, then the treatment plan may include 8 treatments.

Determining the amount of time per treatment for the treatment plan 404 may utilize the damage region having the most proximal (e.g., closest to the torso of the patient) damage for each body portion. Generally, the more proximal the damage, the greater the amount of time, which will be provided in the output or treatment plan.

For example, as shown in FIG. 11A, each leg having damage more proximal than or equal to LE-4 may be assigned 15 minutes and each leg having damage less proximal than or equal to LE-3 may be assigned 10 minutes. Further, each arm having damage more proximal than or equal to A-1 may be assigned 10 minutes and each arm having damage less proximal than or equal to H-4 is assigned 7.5 minutes. After each of the body portions has been assigned a time value, the values may be summed to produce a total amount of time for each treatment of the treatment plan.

The total amount of time for each treatment may be limited for various reasons, e.g., patient comfort, etc. For example, as shown in FIG. 11A, if both legs are damaged and at least one arm has a damage region greater than or equal to A-1 (see FIG. 9), then the total amount of time may be limited to 40 minutes. Further, if both legs are damaged and at least one arm has a damage region less than or equal to H-4, then the total amount of time may be limited to 30 minutes.

Another exemplary method of generating a treatment plan for a patient's sensory impairment may utilize a look-up table (or any other processor addressable information database) to generate a treatment plan. For example, an exemplary table 408 for use in generating a treatment plan for a patient's sensory impairment is depicted in FIG. 11B.

As described, an exemplary treatment plan may include the number of treatments and a time value, or amount of time, for each treatment. The number of treatments and the time value for each treatment are, however, merely estimates because the exemplary methods of treating sensory impairment described herein may be modified over time depending, e.g., on the effectiveness of the treatments, subjective patient data, objective measurement data, new treatment techniques, new treatment apparatus, etc.

Further, an exemplary treatment plan can include exemplary stretching exercises as well as any other therapy described herein.

Figure 5:
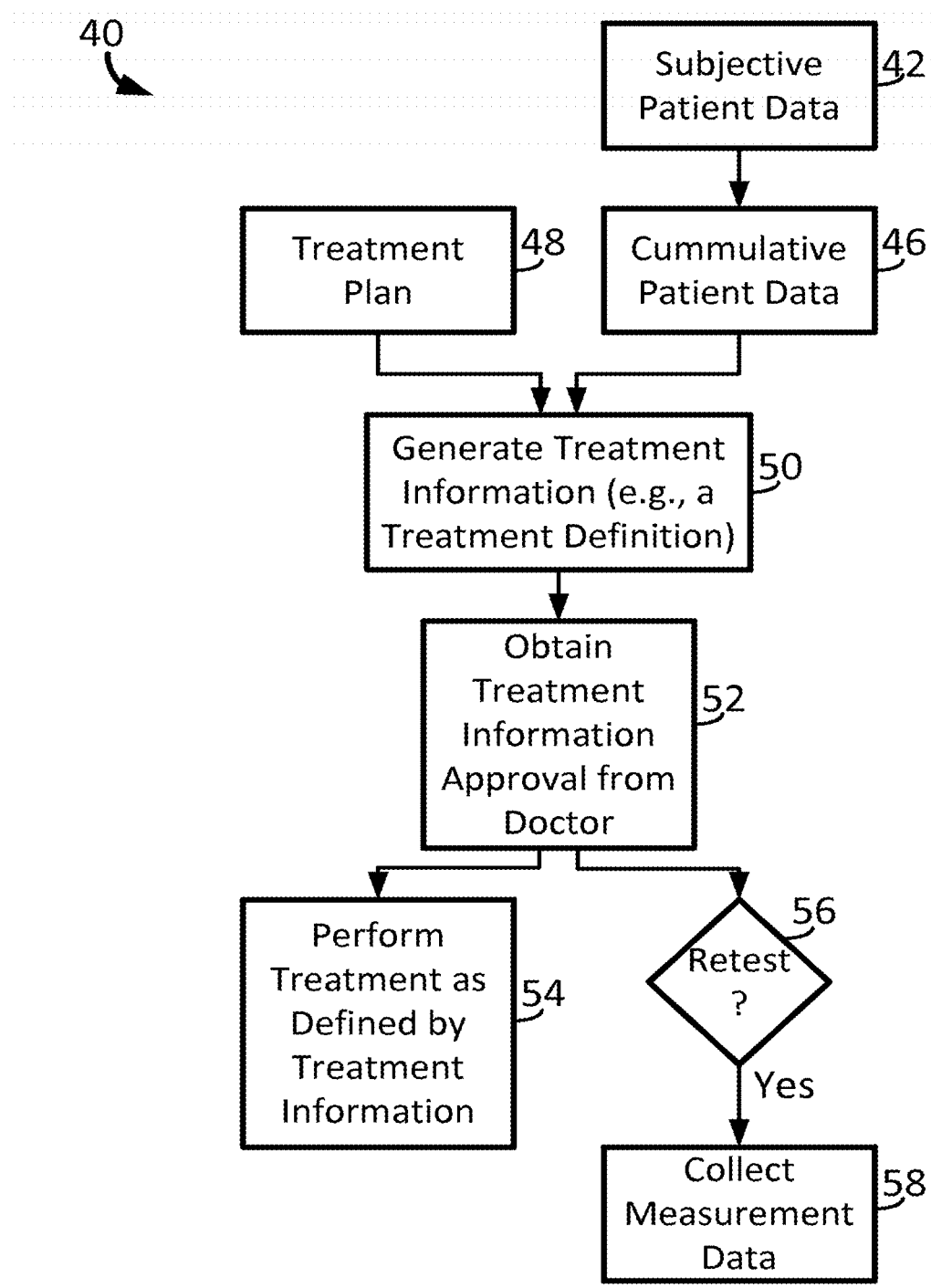
FIG. 5 is a more-detailed block diagram of the treatment(s) of the exemplary method of FIG. 3.

After the initial consultation 24 (e.g., in which treatment information such as a treatment plan has been generated 31), one or more treatments 26 may be performed on the patient as shown in FIG. 3. An exemplary method of treatment 40 is depicted in FIG. 5.

Similar to the method of generating a treatment plan 31 shown in FIG. 4, the method of treatment 40 may include collecting subjective patient data 42. In at least one embodiment of collecting subjective patient data, a therapist may ask the patient a plurality of questions regarding their sensory impairment. For example, a therapist may ask the following questions: When did the pain start? Has the pain calmed down? Is the pain radiating? Muscle pain?Exactly where is the pain? When did you notice the numbness or dull feeling? Exactly where is the numbness or dull feeling? Padded, is it feeling thinned out or thicker or is it tight? Do you notice any padded sensations? (e.g., a slight numbness like they still have their socks on, or that they are walking on a pad of some sort) Does it feel thinned out or thicker or is it tight? Exactly where is the padding, in the toes, ball of foot or heel? Any tingling? When did the tingling increase or decrease, exactly where? When did the burning start? Was this a hot burning sensation or a stinging or pins and needles sensation? When did you notice a change in the burning, if any change? Did you need to cool the burning with water or was it tolerable? Did the burning increase or decrease later on, e.g., did it first go up and then come down? Exactly where is the burning?

Such subjective patient data 42 may also include restoration symptoms. For example, if nerve activity has increased (e.g., regenerated, restored, etc.), various subjective restoration symptoms may result therefrom that are not due to peripheral neuropathy and/or vascular impairment. More specifically, as nerve activity increases, the use of various tissues such as muscles, joints, ligaments, tendons, etc. may also increase (e.g., due to the increase in nerve activity). Consequently, such muscles, joints, ligaments, tendons, etc. may react to the increase in use resulting in such restoration symptoms. Such restoration symptoms may include tightness, soreness, contraction, cramps, pins and needles, buzzing, humming or stinging sensations, tenderness during weight bearing, sharp shooting or zipping sensations, fatigue, and or heavy or wobbly sensations, itching, burning, or feelings of general fatigue, etc. In at least one embodiment, restoration symptoms may be used to indicate that the patient's nerve activity is improving (e.g., peripheral neuropathy is decreasing) even if other data such as objective measurement data and other subjective patient data is not indicating that the patient's nerve activity is improving.

Using the answers from such questions, the therapist can enter the subjective patient data into a computer system (e.g., the computer system 15 described herein with reference to FIG. 2) using a graphical user interface similar to the input interfaces 500, 600 of FIGS. 15A-15D and 16A-16C described herein.

After the subjective patient data has been entered, the method 40 may add the subjective patient data 42 into the cumulative patient data 46. The method 40 may then generate treatment information 50 (for an initial or subsequent treatment) using a computer system (e.g., the computer system 15 described herein with reference to FIG. 2) based on at least the treatment plan 48 and the cumulative patient data 46. More specifically, the treatment information may be generated using an algorithm based on at least presently-collected subjective patient data 42, a treatment plan 48 (e.g., generated in an initial consultation 24), and/or cumulative patient data 46 (e.g., if the patient has already undergone a treatment). Cumulative patient data 46 may include subjective patient data, objective measurement data, evaluation data 27 of FIG. 3, and treatment information determined and/or utilized in previous treatments or otherwise collected.

The treatment information generated 50 may include at least one treatment definition for the treatment to be performed on the patient. The treatment definitions may be preset or predefined, e.g., by the algorithm, or a database or look-up table, and may include one or more treatment regions of the patient to be exposed to photonic energy to treat one or more body portions of the patient afflicted with sensory impairment. Further, the treatment definition may include a time period of exposure to photonic energy for each of the one or more treatment regions. A treatment definition, e.g., may be a guide for a therapist to deliver treatment to the patient.

Generally, treatment definitions generated 50 may direct the amount of exposure time per treatment region and the starting treatment region (e.g., of an extremity) based on the location of the most proximal damage region. For example, a generated treatment definition may direct more exposure time to one or more distal regions of the body portion if the cumulative patient data indicates that the damage is more distal. In other words, the more distal the damage, the more distal the proportion of total exposure time to photonic energy. Further, a generated treatment definition may also direct the starting treatment region (i.e., the region after delivering photonic energy to the root) to a more distal location if the cumulative patient data indicates that the damage is more distal.

For example, if the cumulative patient data indicates that the damage is more distal, then the generated treatment region may direct more exposure time to a patient's calf than thigh (e.g., at least a greater proportion of exposure to the patient's calf than thigh than the last and/or any other previous treatment).

Figure 12:
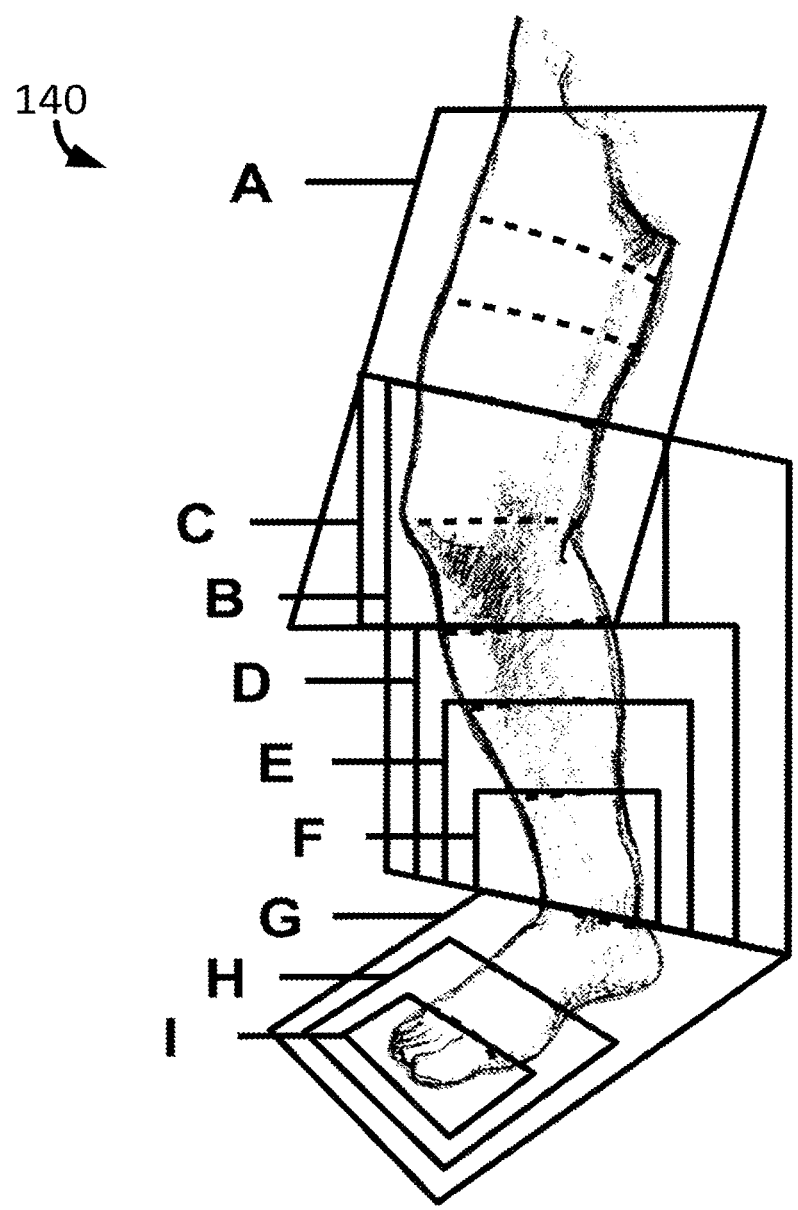
FIG. 12 is an exemplary treatment display for a patient's leg.
Figure 13:
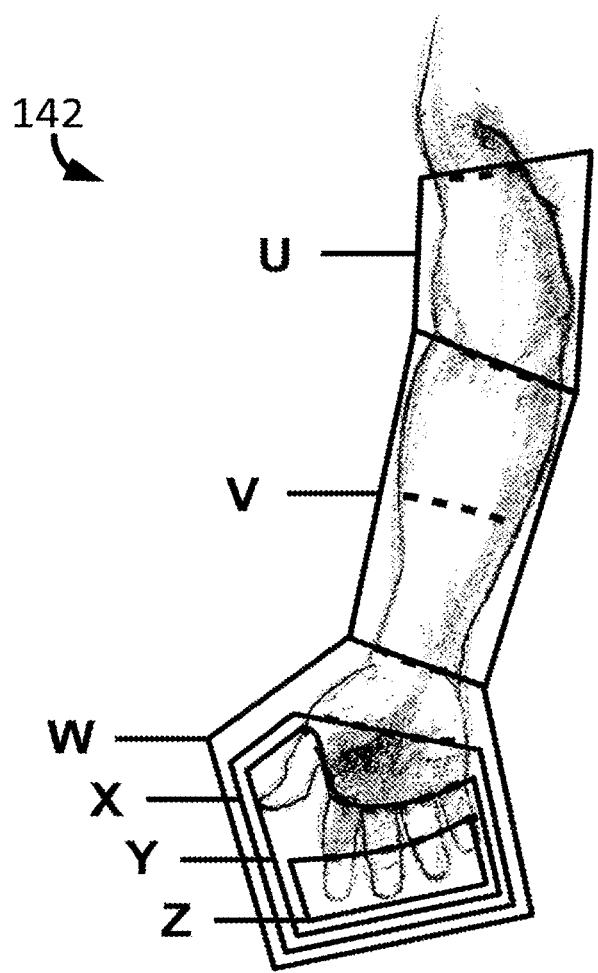
FIG. 13 is an exemplary treatment display for a patient's arm.
Figure 14:
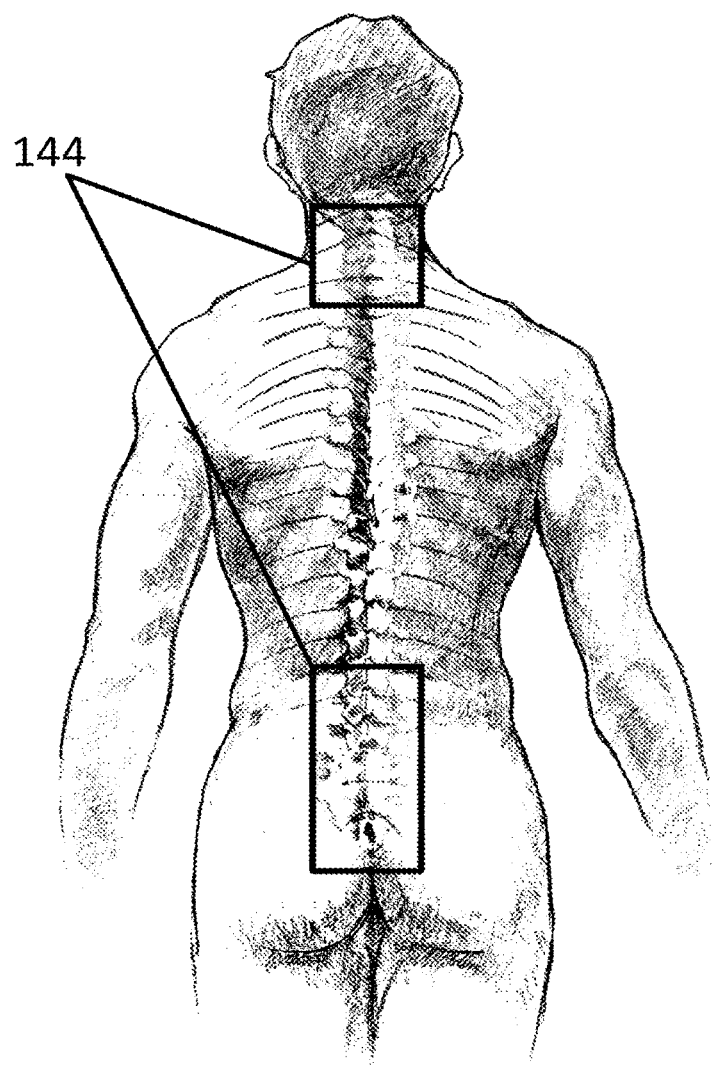
FIG. 14 is an exemplary treatment display for a patient's back.

Exemplary treatment regions are depicted for a leg, an arm, and a back in exemplary treatment displays shown in FIGS. 12-14, respectively. The treatment regions 140 of the leg are labeled A-I. The treatment regions 142 of the arm are labeled U-Z. The treatment regions of the back include the anatomical locations C6-C8, T1-T2, L1-L5, and S1-S2, located in the labeled regions 144.

In at least one embodiment, treatment definitions (e.g., generated for a treatment of a patient during an appointment) may be defined in terms of treatment phases for each different body portion (e.g., leg, arm, etc.). A treatment phase may include one or more treatment regions of the patient to be exposed to photonic energy and a proportion of the total time period of exposure to photonic energy for each of the one or more treatment regions in the particular body portion (e.g., leg). For example, the proportion of the total time period of exposure to photonic energy may be a ratio of how much of the total time spent on each particular treatment region (e.g., if the total time is ten minutes and the treatment phase instructs 1/10 of the total time is to be spent on treatment region A, 1 minute would be spent on treatment region A). Generally, a treatment phase for each body portion may be determined based on the most proximal (e.g., closest to the torso of the patient) damage (see damage regions for a patient's leg, arm, and foot in FIGS. 8-10, respectively) of each particular body portion (e.g., extremity).

For example, a leg may have nine leg treatment phases and the present treatment phase may be determined by the most proximal damage. In at least one embodiment, the leg treatment phase may be determined by the following: if a leg has damage that is greater than or equal to LE-11, then the first leg treatment phase may be determined; if a leg has damage that is equal to LE-10, then the second leg treatment phase may be determined; if a leg has damage that is less than or equal to LE-9 and greater than or equal to LE-8, then the third leg treatment phase may be determined; if a leg has damage that is less than or equal to LE-7 and greater than or equal to LE-6, then the fourth leg treatment phase may be determined; if a leg has damage equal to LE-5 a fifth leg treatment phase may be determined; if a leg has damage equal to LE-4 a sixth leg treatment phase may be determined; if a leg has damage equal to LE-3 a seventh leg treatment phase may be determined; if a leg has damage equal to LE-2 a eighth leg treatment phase may be determined; if a leg has damage equal to LE-1 a ninth leg treatment phase may be determined.

The following is an exemplary list of leg treatment phases. Further, in the following list of leg phase treatments, it is assumed that the total treatment time for both legs, e.g., as defined by a treatment plan, is 30 minutes. Also, as described above, the time of energy exposure for a pair of extremities may also be different. In other words, the time of energy exposure may shift to favor the extremity with the most damage (e.g., if the left leg indicates more sensory impairment, the left leg may get ⅔ of the exposure time while the right leg gets ⅓ of the exposure time). Also, a post-treatment cooling therapy may be used after any treatment or treatment phases described herein as needed (e.g., on an individual case basis. The post-treatment cooling therapy may utilize skin cooling apparatus such as the skin cooling systems produced by ZIMMER MEDIZIN SYSTEMS. For example, cooling therapy may be used to allow therapists and/or practitioners to increase the power density of the photonic energy delivered during treatment while diminishing the probability of hot burning sensations (or any other sensation or reflex) that may be experienced by a patient following treatment (e.g., the night of the treatment).

Leg Treatment Phase I: 6 min of photonic energy exposure to the spine (treatment regions L1-L5, S1, & S2); 4 min/leg (treatment region A) of photonic energy exposure to the leg paying special attention to the head of the fibula; 4 min/leg (treatment region B) of photonic energy exposure to the thigh, paying special attention to the popliteal fossa; and 4 min/leg (treatment region G) of photonic energy exposure to the foot, making sure to get in between the toes and around the inferior portion of the malleoli.

Leg Treatment Phase II: 6 min of photonic energy exposure to the spine (treatment regions L2-L5, S1, & S2); 2 min/leg (treatment region A) of photonic energy exposure at each popliteal fossa and heads of fibula; 5 min/leg (treatment region B) of photonic energy exposure for each leg to the ankle; and 5 min/leg (treatment region G) of photonic energy exposure to each foot, making sure to get in between the toes and around the inferior portion of the malleoli.

Leg Treatment Phase III: 6 min of photonic energy exposure to the spine (treatment regions L3-L5, S1, & S2); 3 min/leg (treatment region C) of photonic energy exposure to the popliteal fossa, the head of fibula, and the knee; 4 min/leg (treatment region B) of photonic energy exposure from the bottom of the knee to the ankle; 5 min/leg of photonic energy exposure (treatment region G); and a remainder of photonic energy exposure time on each foot, making sure to get in between the toes and around the inferior portion of the malleoli (paying special attention to areas that may still be symptomatic).

Leg Treatment Phase IV: 6 min of photonic energy exposure to the spine (treatment regions L3-L5, S1, & S2); 4 min/leg (treatment region D) of photonic energy exposure to ⅔rds of the shin to ankle; 8 min/leg (treatment region G) of photonic energy exposure; and a remainder of photonic energy exposure time on each foot, making sure to get in between the toes and around the inferior portion of the malleoli (paying special attention to areas that may still be symptomatic).

Leg Treatment Phase V: 6 min of photonic energy exposure to the spine (treatment regions L3-L5, S1, & S2); 4 min/leg (treatment region E) of photonic energy exposure to from the mid shin to the ankle; 8 min/leg (treatment region G) of photonic energy exposure; and a remainder of photonic energy exposure time on each foot, making sure to get in between the toes and around the inferior portion of the malleoli (paying special attention to areas that may still be symptomatic).

Leg Treatment Phase VI: 6 min of photonic energy exposure to the spine (treatment regions L3-L5, S1, & S2); 4 min/leg (treatment region F) of photonic energy exposure on the bottom ⅓ of the shin; 8 min/leg (treatment region G) of photonic energy exposure; and a remainder of photonic energy exposure time on each foot, making sure to get in between the toes and around the inferior portion of the malleoli (paying special attention to areas that may still be symptomatic).

Leg Treatment Phase VII: 6 min of photonic energy exposure to the spine (treatment regions L3-L5, S1, & S2); 5 min/leg (treatment region G) of photonic energy exposure to symptomatic areas; 8 min/leg (treatment region H) of photonic energy exposure; and remainder of photonic energy exposure time on each foot, making sure to get in between the toes and around the inferior portion of the malleoli (paying special attention to areas that may still be symptomatic).

Leg Treatment Phase VIII: 6 min of photonic energy exposure to the spine (treatment regions L3-L5, S1, & S2); 4 min/leg (treatment region H); 8 min/leg (treatment region I) of photonic energy exposure; and a remainder of photonic energy exposure time on each foot, making sure to get in between the toes and around the inferior portion of the malleoli (paying special attention to areas that may still be symptomatic).

Leg Treatment Phase IX: 6 min of photonic energy exposure to the spine (treatment regions L3-L5, S1, & S2); 12 min/leg (treatment region I) of photonic energy exposure; and a remainder of photonic energy exposure time on each foot, making sure to get in between the toes and around the inferior portion of the malleoli (paying special attention to areas that may still be symptomatic).

Further, for example, an arm may have 5 arm treatment phases and the present treatment may be determined by the most proximal damage. In at least one embodiment, the arm treatment phase may be determined by the following: if an arm has damage greater than or equal to A3, then the first phase is determined; if an arm has damage less than or equal to A2 and greater than or equal to A1, then the second phase is determined; if an arm has damage equal to H4, then the third phase is determined; if an arm has damage equal to H3, then the fourth phase is determined; and if an arm has damage equal to or less than H2, then the fifth phase is determined.

The following is an exemplary list of arm treatment phases. Further, in the following list of arm phase treatments, it is assumed that the total treatment time for both arms, e.g., as defined by a treatment plan, is 10 minutes. Similar to the leg treatments, post-treatment cooling therapy may be applied when needed.

Arm Treatment Phase I: 2 min of photonic energy exposure to the spine (treatment regions T1 & C6-C8); 1 min/arm (treatment region U) of photonic energy exposure to the shoulder to the elbow; 1 min/arm (treatment region V) of photonic energy exposure to the elbow to the wrist; and 2 min/arm (treatment region W) of photonic energy exposure to the wrist to the fingertips.

Arm Treatment Phase II: 2 min of photonic energy exposure to the spine (treatment regions T1 & C6-C8); 2 min/arm (treatment region V) of photonic energy exposure to the elbow to the wrist; and 2 min/arm (treatment region W) of photonic energy exposure to the wrist to the finger tips.

Arm Treatment Phase IV: 2 min of photonic energy exposure to the spine (treatment regions C6-C8); 1.5 min/arm (treatment region X) of photonic energy exposure to the wrist to the finger tips; and 2.5 min/arm (treatment region Y) of photonic energy exposure to the fingers/finger tips.

Arm Treatment Phase V: 2 min of photonic energy exposure to the spine (treatment regions C6-C8); 1.5 min/arm (treatment region Y) of photonic energy exposure to the wrist to the finger tips; and 2.5 min/arm (treatment region Z) of photonic energy exposure to the fingers/finger tips.

The treatment information generated 50 may also include at least one treatment definition including a power level of the photonic energy to be delivered to the one or more treatment regions. The power levels to be delivered to each of the treatment regions may be generated based on any of the subjective patient data, objective measurement data, cumulative patient data, and/or data plan. Further, a unique or different treatment definition may be determined for each body portion (e.g., extremity) of the patient, e.g., based on the unique or different data indicative of damage for each body portion. For example, a treatment definition for a patient's left leg may have a different power level than a treatment definition for the same patient's right leg.

In the following example, the power level may be generated based on subjective patient data—more specifically, a hot burning sensation in an extremity felt the night or day after receiving treatment (although the patient is not actually burned by the treatment). For example, in the treatment of a patient's leg, the starting (e.g., for the first treatment) power level of the photonic energy for the treatment regions of a patient's back corresponding to the damage regions of the leg may be 6.75 Watts, unless hot burning in the leg was noted in the subjective patient data. If hot burning in the leg was noted in the subjective patient data, the starting power level of the photonic energy for the treatment regions of the patient's back may be 6.25 Watts. In a similar fashion, the starting power level for the treatment regions of the patient's leg may be 5.75 Watts, unless hot burning in the leg was noted in the subjective patient data, and in such hot burning case, the starting power may be 5.25 Watts. Some patients may get a hot burning sensation as they improve. Decreasing the wattage may slow the efficacy of their care, but this can be left to the practitioner's discretion.

Further, in the treatment of the patient's arm, the starting (e.g., for the first treatment) power level of the photonic energy for the treatment regions of a patient's back corresponding to the damage regions of the arm may be 6.75 Watts, unless hot burning in the arm was noted in the subjective patient data. If hot burning in the arm was noted in the subjective patient data, the starting power level of the photonic energy for the treatment regions of the patient's back may be 6.25 Watts. In a similar fashion, the starting power level for the treatment regions of the patient's arm may be 5.75 Watts, unless hot burning in the arm was noted in the subjective patient data, and in such hot burning case, the starting power may be 5.25 Watts. Again, some patients may get a hot burning sensation as they improve. Decreasing the wattage may slow the efficacy of their care, but this can be left to the practitioner's discretion.

In subsequent treatments, if hot burning is noted in the subjective patient data, the power level may be decreased by ½ Watt for the back, the arms, and the legs (i.e., decreased from the power levels used in the last treatment). Further, if hot burning is noted in the subjective patient data for two consecutive treatments, the power level may be decreased by 1 Watt for the back, the arms, and the legs (i.e., decreased from the power levels used in the last treatment). Still further, if hot burning is not noted in the subjective patient data, the power level may be increased by ½ or 1 Watt for the back and ¼ Watt for the arms and the legs (i.e., increased from the power levels used in the last treatment).

After the treatment definition has been generated 50 and before providing therapy to the patient, the method 40 may require a practitioner (e.g., doctor) to approve the treatment definition before a therapist performs the therapy according to the treatment definition. As such, the method 40 includes obtaining treatment information approval from a practitioner 52 before allowing the treatment to be performed 54. Obtaining approval 52 may include presenting the practitioner with the treatment definition as well as any other the treatment information, subjective patient data, objective measurement data, and/or cumulative patient data such that the practitioner can evaluate the present treatment definition.

If the practitioner approves of the treatment definition, the method 40 may proceed to performing treatment on the patient as defined by the treatment definition 54. Further, if the practitioner wishes to modify the treatment definition, the practitioner may do so prior to approving treatment definition 52. In at least one embodiment, this approval process 52 may utilize one or more computer systems operatively coupled to one another such that a practitioner may approve of a treatment definition using a computer system that is remotely located with respect to a therapy system. Such computer systems will be further described herein with reference to FIGS. 6-7.

Further, in at least one embodiment, the practitioner may be presented with a graphical user interface for approval and/or modification of the treatment definition.

If the practitioner approves of the treatment definition, the treatment may be performed on the patient 54. In at least one embodiment, the therapy system to be used by the therapist to deliver photonic energy may not be activated (e.g., such that it may not be used to expose treatment regions of a patient to photonic energy) until the therapy system receives approval from the practitioner. Further, in at least another embodiment, the therapist may not be signaled or notified to begin the treatment until the practitioner approves the treatment definition.

Figure 6:
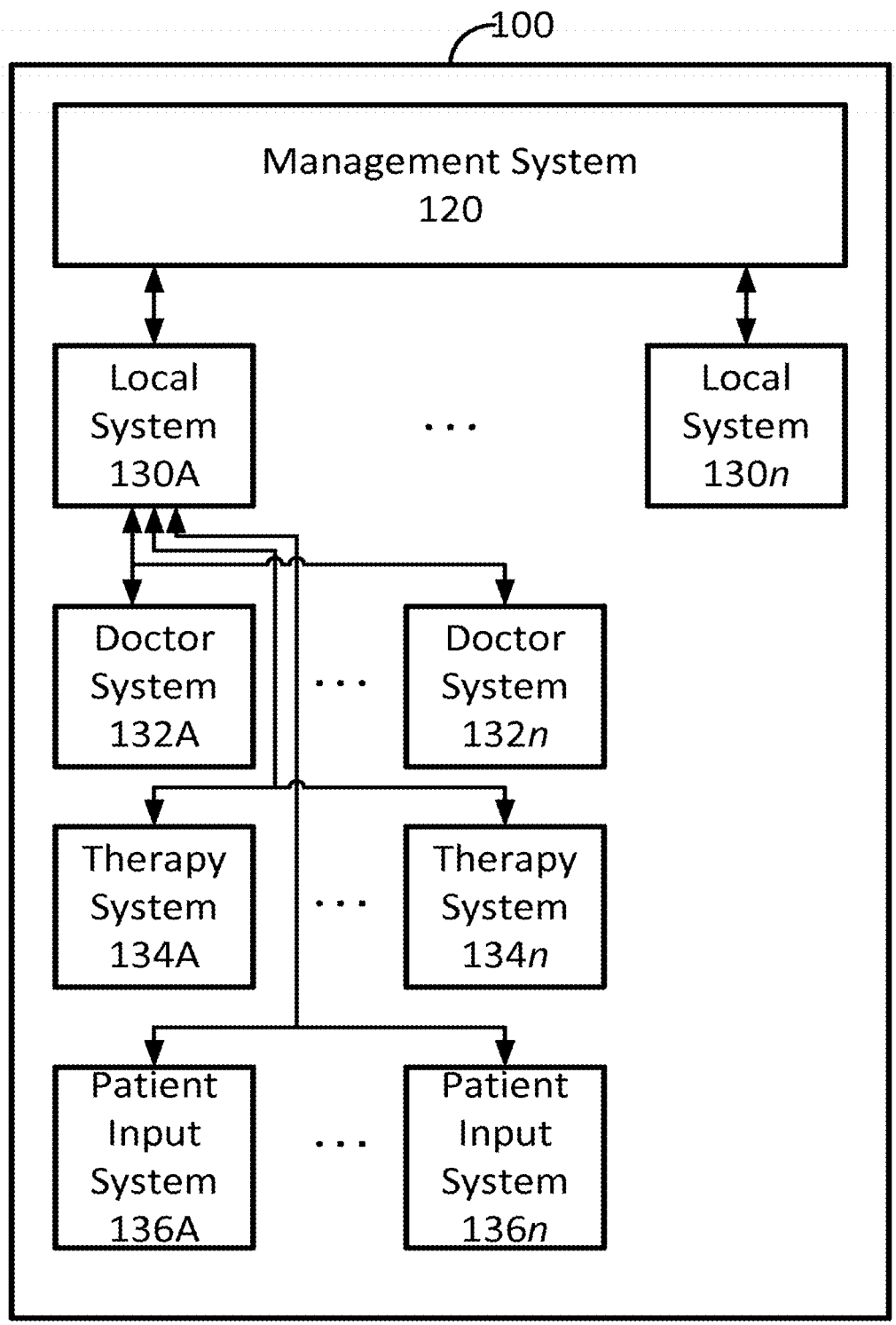
FIG. 6 is a block diagram of an exemplary system for use in treating one or more patient's sensory impairment.
Figure 7:
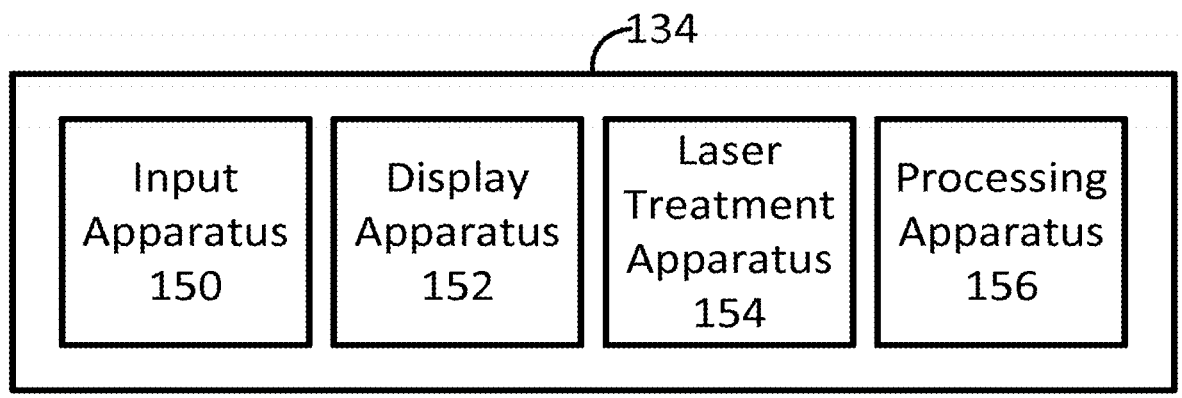
FIG. 7 is a block diagram of the therapy system of the exemplary system of FIG. 6.

Further, the therapy apparatus (e.g., therapy system 13 as described herein with respect to FIG. 2) used to deliver photonic energy to the patient may be controlled by the treatment definition (e.g., generated by the local system 132 as described herein with reference to FIG. 6). In other words, the local system 132 (as described herein with reference to FIG. 6) may control any one or more parameters of the therapy apparatus that delivers photonic energy (e.g., power, time, pulse frequency, frequency, wavelengths, etc.). For example, if the treatment definition calls for a power level of 6.5 W, then the therapy apparatus may only output 6.5 W. Still further, the therapy apparatus may also include a timer that counts down the time remaining for the time period for each particular treatment region, and upon expiration of the time period, may indicate to the therapist (e.g., through sound, light, etc.) to move the laser therapy to the next treatment region.

Figure 17A:
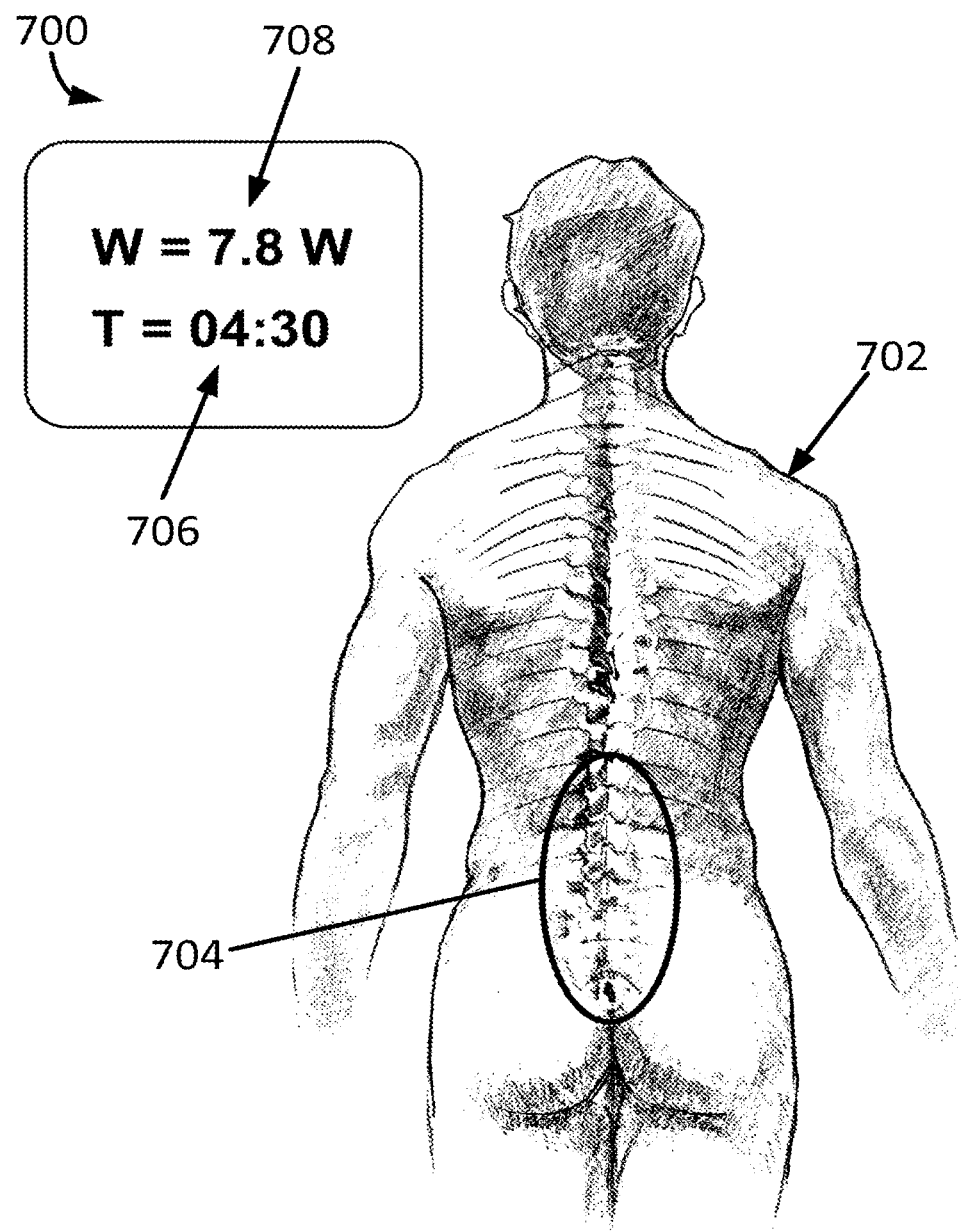
FIGS. 17A-17D are exemplary graphical user interfaces for use in a treatment, e.g., in a treatment such as the treatment of FIG. 5.

An exemplary graphical user interface 700 to be used by the therapy system 13 during treatment (e.g., delivery of photonic energy to the patient under control or controlled by a treatment definition) is depicted in FIGS. 17A-17D. As shown in FIG. 17A, the graphical user interface 700 depicts a portion of a human body 702, e.g., a portion that shows the treatment region for the present step and identification 704 of the treatment region on the portion of a human body 702. As show, the identification 704 includes an outline of the treatment region. In at least one embodiment, the identification 704 may include "highlighting" of the treatment region on the portion of a human body 702. As such, a therapist may view the interface 700 to determine where the photonic energy should be delivered to the patient.

Figure 17B:
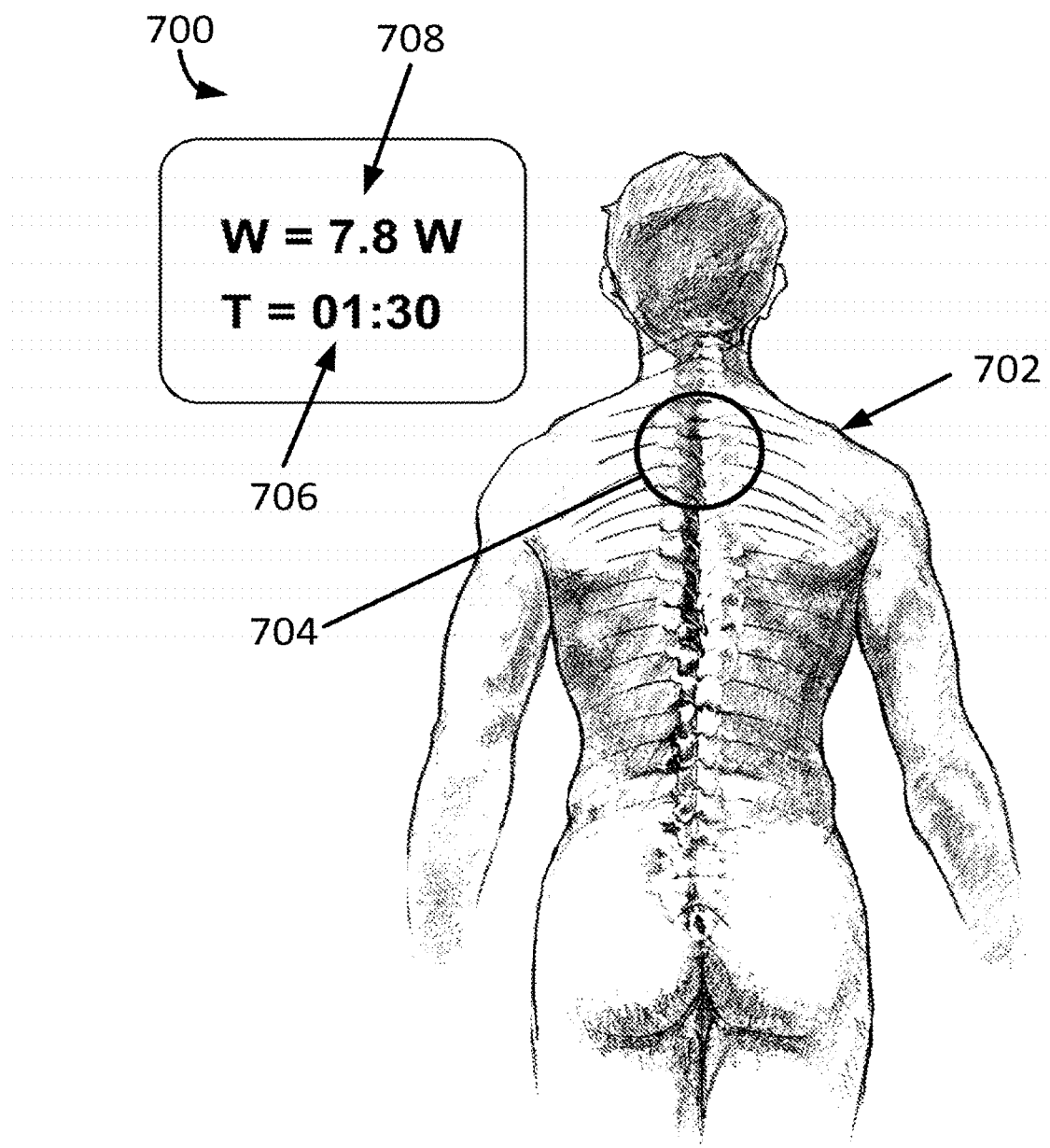

The interface 700 may further depict a time period of exposure 706 for the treatment region to be exposed to photonic energy using a therapeutic laser. The time period of exposure 706 may decrement, or decrease, in response to the therapist delivering photonic energy using the therapy apparatus. For example, the therapist may have to depress a button, or flip a switch, to deliver photonic energy using a therapeutic laser, and the time period of exposure 706 may decrease, or "count down," when the button is depressed, or the switch is flipped. The interface 700 may further indicate to the therapist when the time period for exposure 706 has finished such that the therapist may move to the next step, e.g., as shown in FIG. 17B. The interface 700 may further depict a power value 708 of the photonic energy to be delivered to the treatment region 704.

Figure 17C:
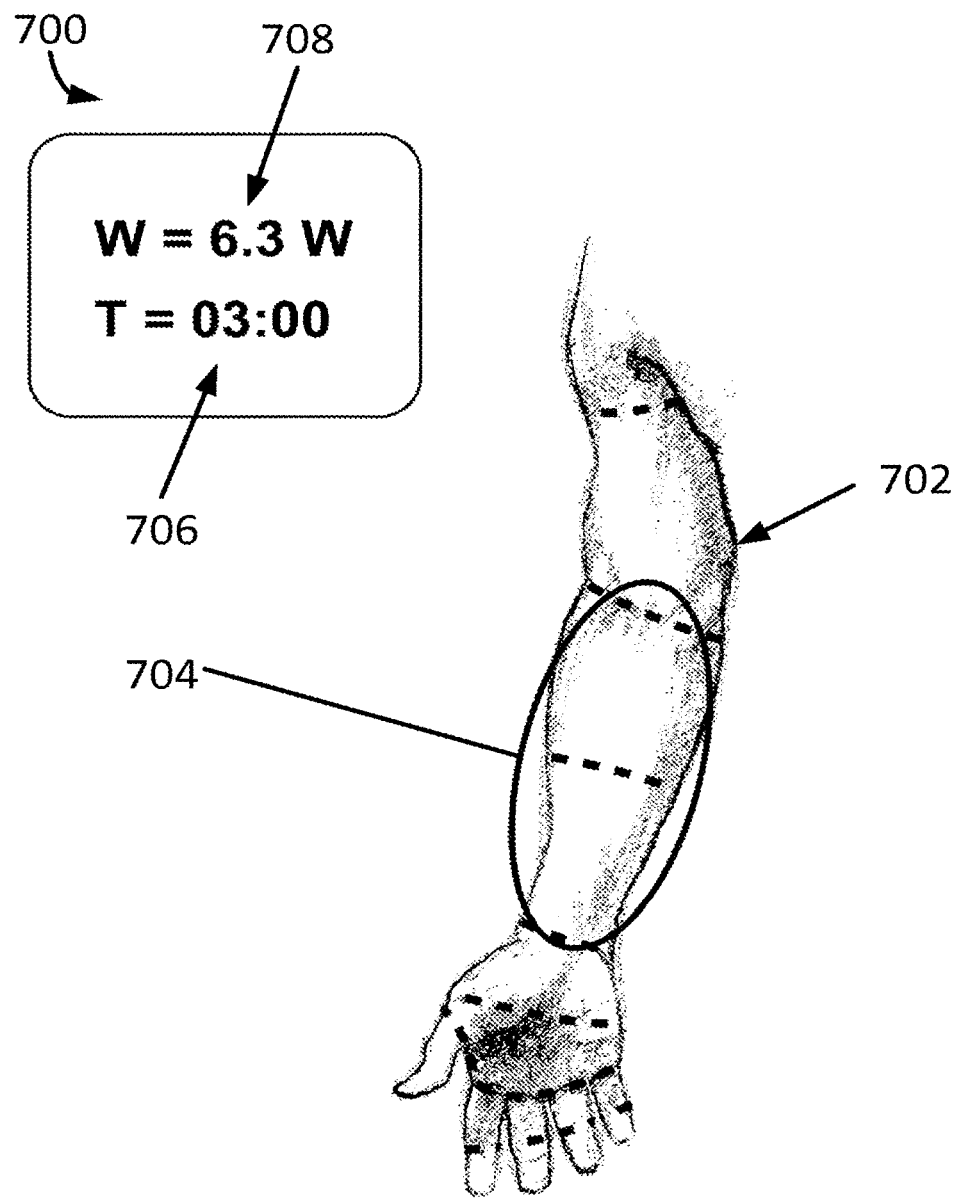
Figure 17D:
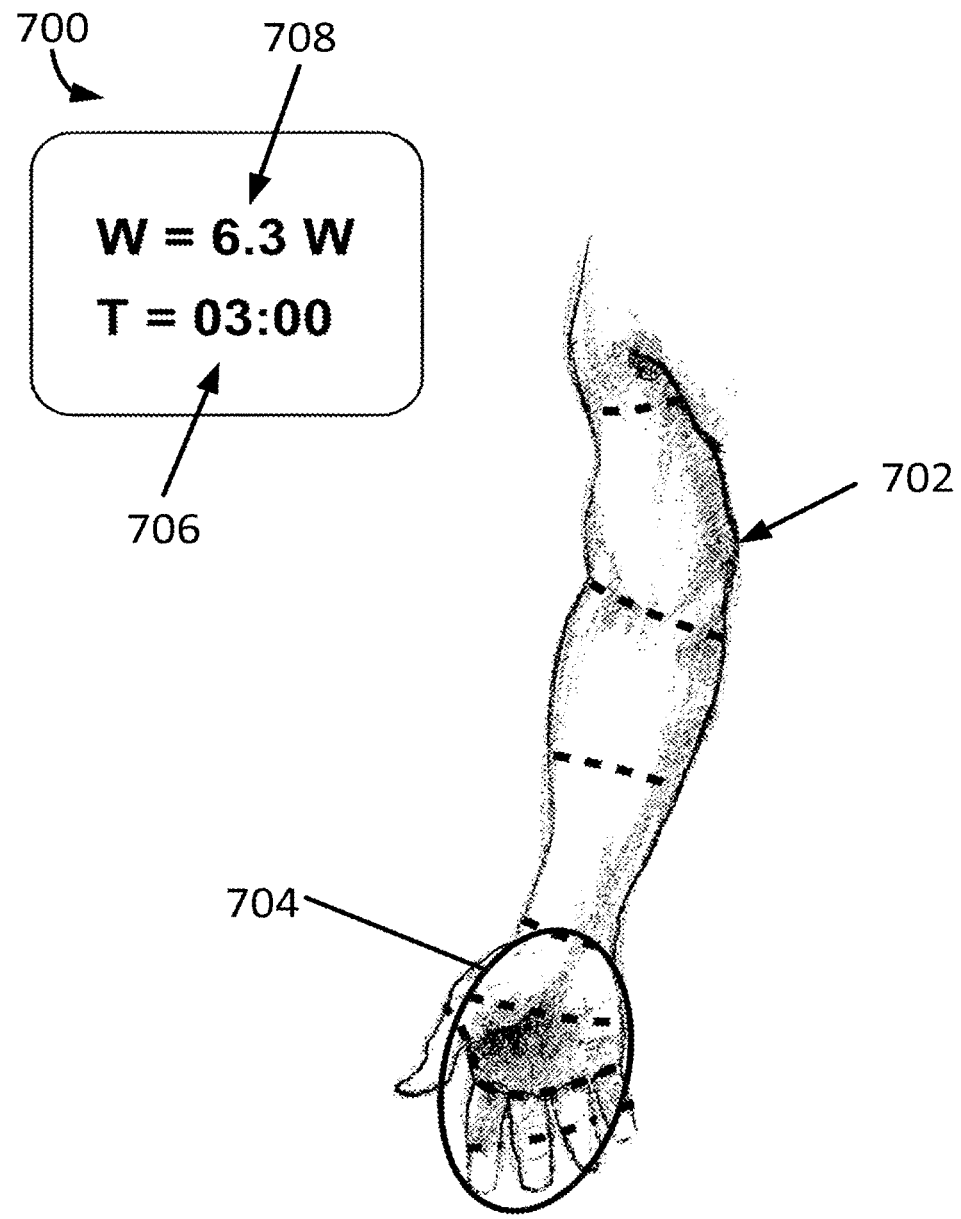

As provided by a treatment definition, the interface 700 may depict treatment processes that include delivery of photonic energy to selected tissue in proximity to a selected nerve root, e.g., as shown in FIGS. 17A-17B, and delivery of photonic energy to selected tissue of an affected extremity in proximity to a nerve extending from the selected nerve root, e.g., as shown in FIGS. 17C-17D. More specifically, as shown in FIGS. 17A-17B, the interface 700 directs therapy to be delivered to the selected tissue in proximity to a selected nerve root, e.g., spinal region L3-S2 and C6-T1, and as shown in FIGS. 17C-17D, the interface 700 directs therapy to be delivered to the selected tissue of the affected extremity in proximity to a nerve extending from the selected nerve root, e.g., the surface of the arm and the surface of the hand.

Although the exemplary interface 700 shown in FIGS. 17A-17D depicts a back and arm for delivery of therapy, the interface 700 may depict any portion of a human body, e.g., leg, hands, feet, etc. After the treatment has been completed, an interface may be displayed to the therapist showing each of the therapy steps that were completed.

The therapy apparatus as described herein with reference to FIG. 2 may include laser treatment apparatus. In at least one embodiment, the laser treatment apparatus may include a button that, when actuated, delivers photonic energy through, e.g., a wand. In the exemplary therapy apparatus that has a timer, the timer may only "count" or "run" when the button is actuated such that, e.g., the therapist delivers photonic energy for the full amount of time as instructed by the therapy apparatus, per treatment definition.

For one or more reasons, the method 40 may determine that the patient should be retested 56 and that the practitioner should collect objective measurement data from the patient 58. Such retesting may be one way that the treatment definition may substantially change, e.g., change a treatment phase, such as moving from treatment phase I to treatment phase II on a leg.

In at least one embodiment, if the newly-generated treatment definition has changed by a certain quantifiable amount from the treatment definition of the last treatment (e.g., subjective increase or decrease of symptoms), then it may be determined that the patient be retested 56. For example, if subjective patient data collected during the present treatment appointment indicates that at least one region of one or more of the patient's body portions has had a 30% or greater change in pain (or another sensation), then it may be determined that the patient be retested 56. Further, for example, if the subjective patent data indicates either an increase or decrease of 30% or a substantial decrease in symptomatic surface area, then it may be determined that the patient be retested 56.

Further, in at least one embodiment, the treatment plan may specifically schedule retests (e.g., one or more retests) to occur over the course of the treatment plan. For example, in a treatment plan having 15 treatments, a retest may be schedule for the $3^{rd}$, $8^{th}$, and $12^{th}$ treatment. Further, a retest may be scheduled during the final treatment. As such, if it is determined that the treatment plan has scheduled a retest on a particular treatment, then it may be determined that the patient be retested 56.

Further, as shown in FIG. 5, the new objective measurement data collected 58 after determining to retest 56 may be inputted into the cumulative patient data 46 such that it may be used in the generation of treatment information 50 during the next treatment appointment. In at least one embodiment (not shown), the retest may take place prior to the present treatment such that the treatment definition may be modified according to the newly-collected objective measurement data prior to the present treatment.

If, during the retesting, the practitioner determines from the objective measurement data that no body portions have any damage regions remaining, the treatment may be complete, and any additional treatment may be maintenance or follow-up treatments. For example, as shown in FIG. 3, after the treatments 26 have been completed, the method 22 continues to follow-up/maintenance treatments 28, which may include regularly scheduled treatments to maintain the health of the patient (e.g., to inhibit sensory impairment from reappearing).

Further, a patient may have symptoms even after objective measurement data indicates success (e.g., if areas of pinprick/vibration have been restored). Areas indicative of damage, or past damage, may be used as an indication of where the damage has gotten to, as well as an indication of which areas are responding. Also, any symptoms, or subjective patient data, may be collected and used to determine, or to generate, treatment information to be used to treat a patient. In at least one embodiment, the additional symptoms, or subjective patient data, may be entered using any of the graphical user interfaces (e.g., interface 500 shown in FIGS. 16A-16C) and/or systems described herein.

Follow-up/maintenance treatments 28 may be automatically scheduled 1 month to 6 months after the treatments 26 have been completed. Further, additional follow-up/maintenance treatments may be scheduled in the future based on a determined frequency of treatments that inhibits the reassurance of sensory impairment.

For example, maintenance appointments may be initially scheduled every two months. If the area of sensory loss/impairment is at the ankle or the mid-foot, then the maintenance appointment frequency (e.g., the time period between appointments) may be maintained. If the area of sensory loss/impairment is below the mid-foot and the patient is comfortable, then the time period between maintenance appointments may be decreased by about 2 to about 4 weeks. If the area of sensory loss/impairment is above the ankle, then then the time period between maintenance appointments may be increased by about 1 to about 2 weeks. Further, if a patient skips or misses a maintenance appointment, another maintenance appointment may be scheduled in about 1 to about 2 weeks.

In each follow-up/maintenance treatment 28, subjective patient data and objective measurement data may be collected and entered into a computer system for recordkeeping and the generation of a treatment definition for treatment, if needed.

Further, at any time with general method 22 of FIG. 3, one or more further evaluations 27 may be conducted to, e.g., establish a general aggregate appraisal of the patient's sensory neuropathy. The one or more evaluations may include the collection of subjective patient and/or objective measurement data and may utilize a modified Total Neuropathy Score, a Balance Screening Test, and/or one or more Quality of Life tests.

Each of the Modified Total Neuropathy Score (mTNS), the Balance Screening Tool (BST), and the Neuro-QOL can be administered at the start of treatment, the end of treatment, 3 months post treatment, and every 6 months after that. The scores may be added to the multi-variant measures to more accurately assess long term results of treatment and in improving the treatment modalities at initial treatment and as part of maintenance treatments. The following references include articles using these tools to rate patients with neuropathy symptoms: http://www.supportiveoncology.net/journal/articles/0408w09.pdf and http://www.ncbi.nlm.nih.gov/pubmed/20357656. The Modified Total Neuropathy Score measures sensory symptoms, motor symptoms, neurological exam motor and reflex scores.

A balance test can be used in the methods of the present disclosure. An exemplary balance test is described, for example, at http://ijahsp.nova.edu/articles/vol5num4/pdf/langley.pdf. http://www.ijtr.co.uk/cgi-bin/go.pl/library/article.cgi?uid=22472;article=IJTR_13_12_558_561. This test has been validated with the "gold standard" tool for balance in an elderly population with is the Berg Balance Test. The actual test and how to administer and score it are further described in the Examples Section.

The Neuro-QOL Test has several short screening tools as part of the intake process from which the practitioner can select. The tool is described further at http://www.mss.northwestern.edu/faculty/cella.html and http://www.neuroqol.org/Web %20Pages/Neuro-Qol%20Team.aspx.

Figure 18A:
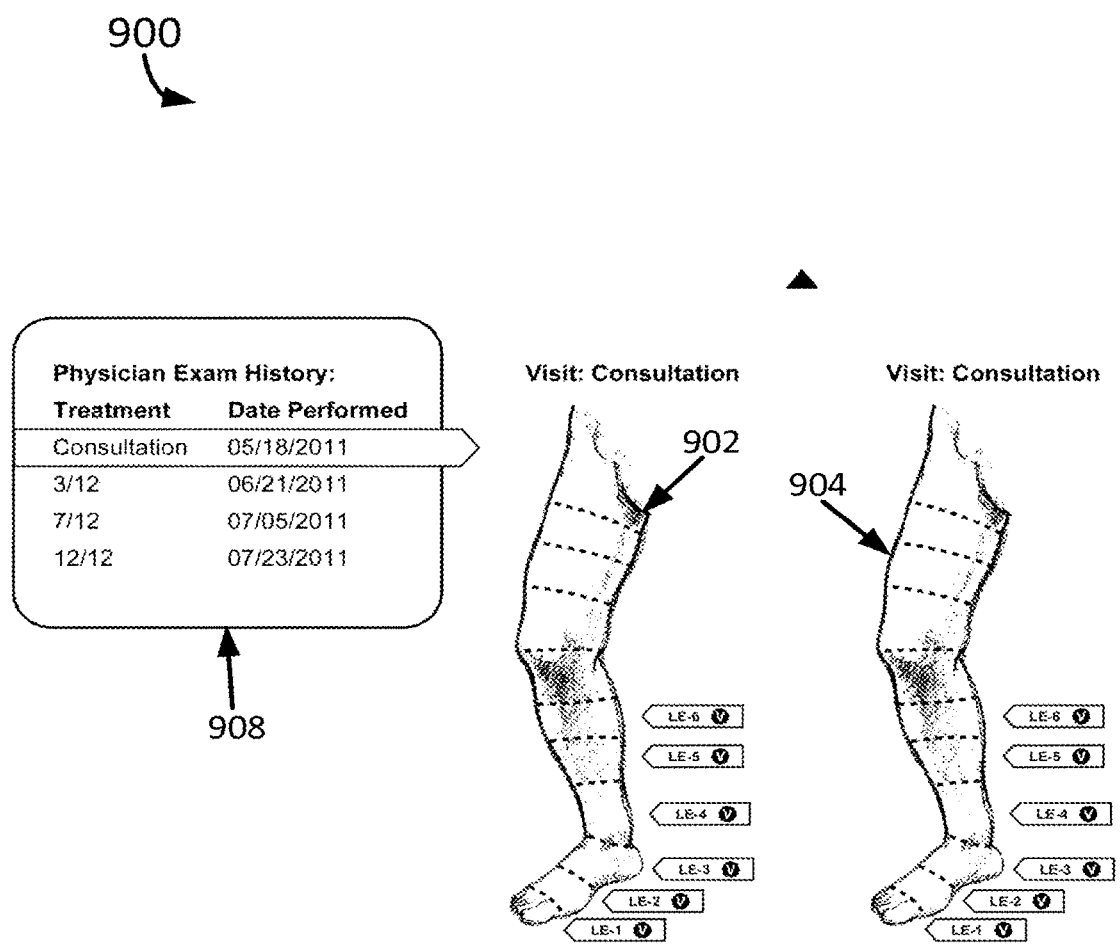
FIGS. 18A-18B are exemplary graphical user interfaces for use in displaying data such as, e.g., objective measurement data, etc.
Figure 18B:
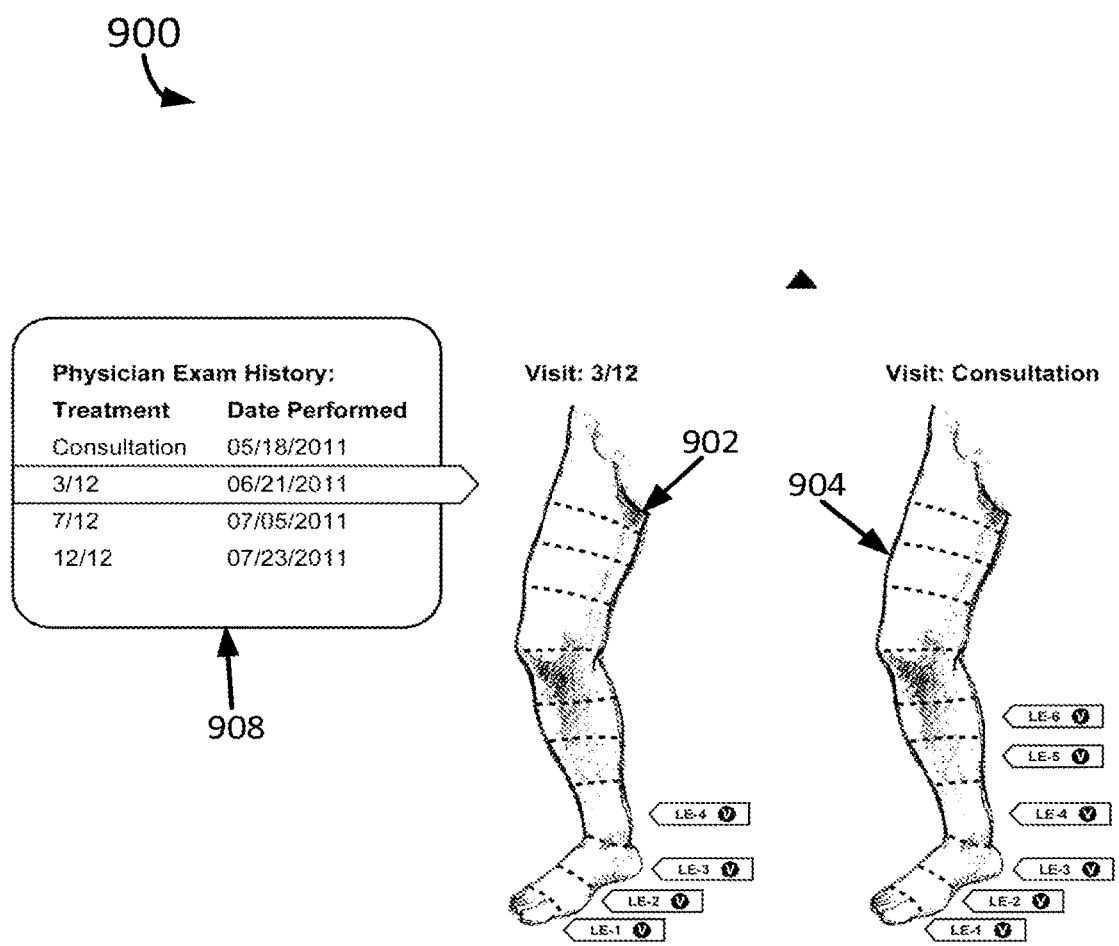

During patient consultations, it may be useful to graphically depict the progress of the treatment. As such, the exemplary methods and systems described herein may further include graphical user interfaces, as shown in FIGS. 18A-18B, for display of various historical data, e.g., regarding the subjective patient data, objective measurement data, treatment information (e.g., including treatment definitions, performed treatments, etc.), and/or any other information collected, or gathered, over the course of therapy. For example, any progress may be shown by displaying subjective patient data (or any other data such as objective measurement data) recorded during the initial consultation (or any other treatment) next to subjective patient data (or any other data such as objective measurement data) recording during a subsequent treatment.

As shown in FIGS. 18A-18B, a first body portion 902 and a second body portion 904 are depicted in exemplary interface 900. Different damage regions 906 may be identified on each body portion 902, 904 similar to the objective/subjective patient data input interfaces described herein (e.g., each damage region may have one or more icons representing the one or more sensation and the one or more values associated with each sensation). The one or more sensations and values indicated by icons on the second body portion 904 may be representative of the sensory impairment measured, or recorded, during an initial consultation (e.g., before receiving any therapy). The one or more sensations and values indicated by icons on the first body portion 902 may be representative of the sensory impairment measured, or recorded, during a consultation selectable using dialog 908.

For example, as shown in FIG. 18A, the sensations and values from objective measurement data indicated on the first body portion 902 are representative of the sensory impairment measured during the initial consultation, and as a result, mirror the second body portion 904. As shown in FIG. 18B, if a user selects a treatment using the dialog 908, the icons representing the sensations and values on first body portion 902 will change to that which were measured during the selected treatment (e.g., the 3/12 treatment). As can be seen by comparing the first body portion 902 and the second body portion 904, this exemplary patient has shown an improvement in sensory impairment from the initial consultation to the 3/12 treatment performed on Jun. 21, 2011.

In other words, interface 900 provides a side-by-side comparison of the progression of the treatment of a patient's sensory impairment, which may be useful in showing a patient the effectiveness of the treatment. The interface 900 may be further used with other body portions, such as a foot, an arm, and/or any other body portion contemplated.

As described herein, exemplary methods for use in treating a patient sensory impairment may utilize one or more computer systems. An exemplary enterprise system 100, including a plurality of computer systems, that may be used in the implementation of one or more exemplary methods described herein is depicted in FIG. 6.

The enterprise system 100 includes a management system 120 and one or more local systems 130A, . . . 130n. The management system 120 (e.g., which may be a central hub system for the local systems 130) and the local systems 130 are operatively coupled (e.g., through a networking connection over the Internet) such that they may exchange information with respect to the facilitation of providing systems and methods for the treatment of sensory impairment. Further, the management system 120 may install software updates to the local systems 130, e.g., to update treatment algorithms, etc. Still further, the management system 120 and the local systems 130 may exchange financial information, e.g., calculate licensing fees, process insurance information, etc.

The management system 120 may be capable of receiving all or portions of the subjective patient data, objective measurement data, treatment information, etc. recorded or entered into each of the local systems 130 to generate a dataset of all the patients being treated by the system 100. The management system 120 may utilize such data to generate and/or modify one or more treatment algorithms, e.g., tailored to treat specific symptoms, etc. The management system 120 may further be capable of transmitting the new and/or improved algorithms to each of the local systems 130.

In at least one embodiment, the management system 120 may be designed to group similar patients and track and assess their symptom improvement in acute care (e.g., over 3-6 weeks) and/or symptom improvement in lifelong follow-up care. Further, the management system 120 may iteratively test various parameters of the therapeutic laser being used by therapy systems to assess the parameters being used (e.g., evaluate each parameter's importance in the acute treatment of a patient symptoms and/or the long term effectiveness of the treatment). For example, the management system 120 may use different treatment algorithms/ protocols to generate various treatment settings to be used by various local systems. The effects of the various treatment settings may be compared to determine their effectiveness (e.g., one or more parameters or settings used with the therapeutic laser may be analyzed in view of the effectiveness as shown through collected subjective patient data and objective measurement data). In at least one embodiment, the management system 120 may identify certain groups of peripheral neuropathy patients that respond to a particular course of treatment.

Further, the management system 120 may coordinate and conduct double-blind and placebo testing on small or large groups of patients and on individual patients (e.g., to treat one leg with the laser and the other with placebo) by transmitting various treatment algorithms (e.g., for use in generating treatment information) to one or more locals systems 130. As described herein, the management system, which may effectively be a centralized control system, may have the ability to download all information with respect to every patient being treated by any of the one or more local systems 130. Such information may include all or portions of the subjective patient data, objective measurement data, treatment information (e.g., operating parameters of the laser, number of treatments, duration of treatments, and/or frequency of treatments, etc.), any treatment definition or protocol changes (e.g., made by a doctor, etc.). The ability to conduct double-blind and placebo testing may also reside in each local system 130, e.g., with the ability to edit and define each treatment protocol for each individual patient.

A wide range of objective and subjective measurements may be used to access and to track a patient's peripheral neuropathy symptom status. At a high level, the length of time a patient has had peripheral neuropathy, the ideology, which may be broken into categories such as metabolic, idiopathic, toxic, trauma, autoimmune, infection, hereditary, etc., and any drugs the patient has been taking may be tracked. This information may allow (e.g., the management system 120) to assess if there are certain types of peripheral neuropathy that can and should be treated differently and if some respond better than others.

Further, the subjective patient data recorded and tracked over time using the systems and methods described herein includes the patients perception of pain, tingling, numbness, tightness and burning (e.g., heat) on any extremity broken down in discrete damage regions (e.g., eleven different damage regions on legs, eight different damage regions on the arms). This subjective data is survey data and may be measured every treatment. In addition, the objective measurement data may include objective assessments of pinprick and vibration of the same damage regions of the affected extremities, which may be measured during objective measurement exams that may be completed at least 4 times during the course of acute care and during any follow-up care. Also, the methods and systems described herein may further collect data using three higher level exams from the beginning of acute care through the end of acute care, and then every 6 months for the lifetime of care. Such high level tests may be the Modified Total Neuropathy Score, BST Balance Test, and a series of Quality of Life Assessments for the various areas (e.g., stigma, sleep disturbance, upper extremity function, lower extremity function, satisfaction with social roles and activities, ability to participate in social roles and activities, fatigue, etc.).

Using the management system 120, such data may be analyzed to iteratively test various laser settings to see which improves acute care (e.g., symptom relief) for the various types of peripheral neuropathy, with the goal to develop the optimal acute laser treatment for each type of peripheral neuropathy. Further, the data may be analyzed to assess long term effectiveness for the above and assess how the various peripheral neuropathy drugs affect care acutely and in the long term.

Further, the methods and systems described herein for tracking and analyzing data including subjective patient data, objective measurement data, supplemental data (e.g., drug information, etc.) and/or treatment information may be used on diseases/conditions other than peripheral neuropathy In other words, the methods and systems described herein could be replicated for other diseases and/or other therapeutic tools where a multivariate iterative approach can be used to achieve optimal results.

In at least one embodiment, the management system 120 may provide different treatment algorithms to different local systems 130 such that each local system 130 may test a different treatment algorithm, thereby generating more unique data. The management system 120 may utilize such data to generate or modify one or more treatment algorithms, e.g., tailored to treat specific symptoms, etc.

Further, the management system 120 may be capable of enabling or disabling one or more local systems 130 (e.g., to disable therapy systems, etc.) for various reasons (e.g., not providing data, failure to pay license fee, etc.).

Each local system 130 may also be operatively coupled to one or more practitioner systems 132A, . . . 132n, one or more therapy systems 134A, . . . 134n, and one or more patient input systems 136A, . . . 136n, and operate independently from one another (e.g., one local system does not interact or share data with another local system). The local system 130 may be substantially similar to the computer system 15 described herein with respect to FIG. 2. For example, the local system 130 may be configured to receive input such as, e.g., subjective patient data, objective measurement data, etc., and further configured to generate an output such as treatment information including treatment plans and treatment definitions. Further, the local system 130 may be configured to operate as the central hub for the practitioner systems 132, therapy system 134, and the patient input systems 136 such that it may exchange or broker information between such systems as well as act as data repository.

Each therapy site may include at least one of the therapy systems 134. An exemplary therapy system 134 is further depicted in FIG. 7. The therapy system 134 includes input apparatus 150, display apparatus 152, laser treatment apparatus 154, skin cooling apparatus (e.g., the skin cooling systems produced by Zimmer MedizinSystems) (not shown), and computing apparatus 156, each of which may be operatively coupled to one another to interoperate. The input apparatus 150 may be any apparatus capable of entering subjective patient data and objective measurement data into the therapy system 134 such as, e.g., a keyboard, a touchscreen, a scanner, a disk drive, a universal serial port, etc. The display apparatus 152 may be any apparatus capable of displaying treatment definitions, graphical user interfaces for the entering of data, etc. such as, e.g., a liquid crystal display, touchscreen, etc. The laser treatment apparatus 154 may include any apparatus capable of delivering photonic energy at a power of at least 6.5 Watts such as, e.g., a K-LASER 1200 produced BY K-LASER USA of Franklin, Tenn., a LCT-1000® DEEP TISSUE THERAPY LASER produced by LITECURE, LLC of Newark, Del., and a AVICENNA AVI HPLL-12 laser produced by AVICENNA LASER TECHNOLOGY, INC. of West Palm Beach, Fla., etc. The processing apparatus 156 may be substantially similar to processing apparatus 16 described herein with respect to FIG. 2.

The therapy systems 134 may be operatively coupled (e.g., through a network connection locally or through the Internet) to the local system 130 such that subjective patient data and/or objective measurement data may be transmitted from the therapy systems 134 and received by the local system 130 and treatment information may be transmitted from the local system 130 and received by the therapy systems 134. Further, the local system 130 may also transmit information to the therapy systems 134 to control to the therapy systems 134, e.g., to block the therapy systems 134 from delivering photonic energy until practitioner approval of a treatment definition is received, etc.

The practitioner systems 132 may be configured to provide any practitioner-related functionality within the exemplary methods described herein. For example, the practitioner systems 132 may be configured to receive and modify treatment definitions, to enter or record objective measurement data, to allow approval of treatment definitions, and to transmit approval messages, treatment definitions (e.g., including modifications), and objective measurement data to the local system 130. In at least one embodiment, the practitioner system 132 may be a tablet computer, e.g., an APPLE IPAD.

The patient input systems 136 may be configured to provide any patient-input-related functionality within the exemplary methods described herein. For example, the patient input systems 136 may be configured to enter or record subjective patient data and to transmit such subjective measurement data to the local system 130A. In at least one embodiment, the patient-input system 136 may be a tablet computer, e.g., an APPLE IPAD.

In other words, the exemplary methods and systems disclosed herein may provide a unified framework of diagnostic parameters that allow the practitioner to objectively quantify differential diagnosis (e.g., by computerized differential diagnosis) in the evaluation and treatment of sensory impairment, e.g., that associated with peripheral neuropathy. That is, while not being bound to any particular scientific theory, the present disclosure provides an internally consistent framework upon which the practitioner can ascertain and develop scientific measurements that can be used in treatment methods.

For example, in one embodiment, the diagnostic tools disclosed herein provides the practitioner with an internally consistent method for systematically collecting data (e.g., objective measurement data and/or subjective patient data) about a medical condition, reducing that data to one or more sets of variables, developing and establishing correlations among and between these variables, and using such correlations to select or establish one or more treatment parameters of a treatment definition. The practitioner then may use this treatment definition to deliver treatment to the patient in a methodical progressive fashion.

Once a patient has been the subject of one or more treatments, the practitioner may then ascertain the condition of the patient once again and collect more data about the patient's condition, including, but not limited to, collecting another set of data in the same manner as done prior to the treatment. Thus, the practitioner iterates the data collection, makes a correlation among or within the data, establishes another treatment definition using the exemplary methods and systems to be used within a single treatment, and provides this selected treatment to the patient. The data that can be collected can include, for example, sensations (e.g., pain, tingling, numbness, burning, heat), quality of the sensation (e.g., shooting pain, dull or padded feelings of numbness), level of the sensation (e.g., pain on a scale of 0-10), and whether the sensation is increased or lessened since the last visit. In addition to these and other variables, discussed herein, one variable that can be iterated is the time between each treatment.

Thus, it can be seen by the following non-limiting examples, that the practitioner can use an internally consistent set of scientific observations and measurements to determine treatment information (e.g., to be used in treatment), and determine the efficacy and efficiency of the one or more treatments so as to, e.g., improve the algorithm to generate such treatment information. Thus, differential medical diagnoses can be made using the techniques described herein.

In this context, the term "treatment efficacy" is used to capture the extent of which a particular treatment has been able to modify the underlying condition for which treatment has been established. "Treatment efficiency" is used to capture the effect of each treatment and determine how many individual treatment cycles are to be performed and/or whether the cost/benefit balance for the patient makes subsequent treatment cycles worthwhile to a patient. Worthwhile treatments are subjective and include consideration of the extent to which a patient's symptoms and/or condition have been improved.

Representative parameters and parametric data that can be used by the practitioner in establishing a treatment definition for treatment of peripheral neuropathy (of any origin or type) using, e.g., therapeutic class IV lasers.

For example, in the treatment of peripheral neuropathy affecting the leg or legs, the practitioner may measure the pattern of perceived pain along the lumbar and legs. These measurements can include whether or not a Bibinski reflex is present or absent in one or both legs and whether or not the reflex is normal (n) or abnormal (ab), for example. Once measured, the practitioner can assign a value to this variable (e.g., a variable that could be labeled "BR" for Babinski reflex, right side and "BL" for Babinski reflex, left side). This value could be labeled positive (plus) if the reflex is present and negative (minus) if the reflex is absent. If the reflex is normal, the value that can be assigned is "0". If the reflex is abnormal or atypical, the value that can be assigned is "1". Thus, reduced to mathematical terms, the above data may be represented as follows: BR={+0, −0, +1, −1}; BL={+0, −0, +1, −1}. This representation is exemplary only and is not intended to be limiting.

Another exemplary value that may be used to assist in diagnosis and treatment development is the Wartenberg Pinwheel test that is used for sensory evaluation along the dermatomal axis. In this test, a metal pinwheel may be rolled over the skin to permit establishment of location of whether or not a patient perceives the location of the pinwheel and if the sensation is perceived as greater at any particular region. For example, a diagnostic instrument known as a Wartenberg Pinwheel is rolled over a patient's skin along a nerve's, or multiple nerves', dermatomes. The distance from a particular nerve root is measured. To, capture this data, a variable such as PWP-R (Pinwheel test, sensory perception, right axis) will measure the distance from a right side nerve root to the onset of perception of the pinwheel rolling along the skin. Thus, for example, reduced to mathematical terms, if a patient perceives the pinwheel at a location along the dermatome at a distance of 60 centimeters (cm) from the nerve root, the data would be represented as PWP-R=60 centimeters. Additionally, to permit comparison between sets of data collected from different patients, the term PWP-R may be expressed as a ratio using the parameter variable PWRP-R (pinwheel, relative data, perception, right side) as PWRP-R=60 cm/100 cm, where 60 cm is the position of the location of perception relative to a nerve root and 100 is the distance from the nerve root to the end of the big toe. Thus, the relative value of PWRP-R=0.6. This determination of the mathematical representation of PWRP-R as one relative value further provides an example of inter-data analysis. This representation is exemplary only and is not intended to be limiting.

The Wartenberg Pinwheel test can also be used to detect locations of hypersensitive perception. In this test, a metal pinwheel may be rolled over the skin to permit establishment of location of whether or not a patient perceives a sensation that is greater at any particular location a nerve's, or multiple nerves', dermatomes. As noted above, a diagnostic instrument known as a Wartenberg Pinwheel is rolled over a patient's skin along a nerve's, or multiple nerves', dermatomes. The distance from a particular nerve root is measured. To, capture this data, a variable such as PWHS-L, (Pinwheel test, hypersensitive perception, left axis) will measure the distance from a right side nerve root to the onset of perception of the pinwheel rolling along the skin. Thus, for example, reduced to mathematical terms, if a patient perceives the pinwheel at a location along the dermatome at a distance of 60 centimeters (cm) from the nerve root, the data would be represented as PWHS-L=60 centimeters. Alternatively, to permit comparison between sets of data collected from different patients, the term PWHS-L may be expressed as a ratio using the parameter variable PWRHS-L (pinwheel, relative data, perception, right side) as follows PWRHS-L=60 cm/100 cm, where 60 cm is the position of the location of perception relative to a nerve root and 100 is the distance from the nerve root to the end of the big toe. Thus, the relative value of PWRHS-L=0.6. The determination of the mathematical representation of PWRHS-L as one relative value further provides an example of inter-data analysis. Again, this representation is exemplary only and is not intended to be limiting.

It is noted that any test of neural function may be used. Further, tests may be performed anywhere in or on the body as long as they are reproducible and the practitioner is able to convert their observations to some value of some variable. Applying this concept to the Pinwheel Test above, the practitioner could define another variable as "N-PWP" (non-dermatomal), where perception of a pinwheel placed at any location of the body other than along a particular dermatomal nerve axis of interest. Thus, when testing peripheral nerve function along the arm, the practitioner could first test patient perception along the axis of the radial nerve and capture the response using any consistent metric. This metric could then be assigned to the variable N-PWP. In order to distinguish data obtained from bilaterally symmetric anatomy, the addition of a descriptor to a variable is appropriate. Thus, in capturing a perception response to a pinwheel placed in non-dermatomal areas of the right arm, a suitable variable includes N-PWP-R. Similarly, where the data captured relates to assessing non-dermatomal areas of hypersensitivity with the Pinwheel Test, a variable such as N-PWHS-R could be used.

Other measures of neurological function, for example, known to the practitioner include: Vibrating Tuning Fork Test; Tinel's Test; Pinprick Test; Visual color observation; Temperature; balance; gait. Thus, for example, following patient examination, a multivariate data set can be captured, which could be represented as follows:

Patient X: BR=+1, BL=+0, N-PWP-R=0.7, N-PWP-L=0.5, N-TFR=0.8, N-TFL=0.5, G=U, SCF=pale, wherein: BR is right sided Babinski's reflex; BL is left sided Babinski's reflex; N-PWP-R is non-relative right side Pinwheel perception test; N-PWP-L is non-relative left side Pinwheel perception test; N-TFR is non-relative right side Tuning Fork test; N-TFL is non-relative left side Tuning for Test; G is a clinically defined gait type; SCF-R is defined scale for capturing the color of the right foot.

For subjective patient data, data values may be assigned to a data value set such as that illustrated above for the Babinski Test. Thus, when measuring temperature, data values may be either metric (for example, degrees centigrade) or subjective (for example, W-warm, N-neutral, C-cold). For tests that have a limited value range such as reflexes that present or absent, values such as "+" (positive) and "−" (negative) may be used.

Although descriptive variable annotation assignment has an advantage of providing mnemonic cues, any variable naming scheme could be employed, as long as all practitioners use the same scheme and collect data in similar ways. Such consistency provides the advantage that data can be compared. For example, data obtained from different patients (by the same or different practitioners) can be collected over time. A consistently defined data collection scheme coupled with consistent apparatus of measurement and assignment of values to variables also provides the ability to perform mathematical (e.g., statistical) analyses.

Further, the use of an internally consistent scheme for data capture provides the ability to correlate treatment modalities with treatment outcomes.

A wide variety of sets of data can be visualized using any mathematical tools. For example, "primary data" represents the data as it is initially captured such as the distance along a dermatomal axis that a patient perceives a stimulus. "Secondary data" is the result of processing primary data using any means such as mathematical means to perform correlations within and between sets of data or graphs resulting from plotting data by any means available the practitioner. When using tools that assist the practitioner in using primary data to assign and evaluate treatment plans, the practitioner may graph results, use tables, assign variable to sets of data, or use secondary data such as correlation coefficients. Data can be collected by any means known to the practitioner, including memory, paper, and/or electronic means, using, for example, diagrams of the body sectioned as shown herein, e.g., in FIGS. 8-10.

The multitude of potential measurements can include an indefinite number of parameters including those well known in the medical community, as well as those to be developed by a practitioner. Regardless of the measurement, using the examples and guidance contained herein, the practitioner can reduce data to parameters and parametrics.

To aid the practitioner in detection, appreciation, and utilization of data, the information contained in the data can be analyzed by using any mathematical and/or statistical visualization tool. For example, please see the following for exemplary analysis methods and/or systems that may be used with the exemplary methods and/or systems disclosed herein: http://citeseerx.ist.psu.edu/viewdoc/download?doi=10.1.1.103.528&rep=rep1&type=pdf.

Further, the following provides Fourier and Calculi for doing line projections; very amenable to computer based visualization of paired datasets: http://www.ifs.tuwien.ac.at/~mlanzenberger/teaching/ps/ws04/stuff/auth/00146402.pdf.

Practical applications: The Andrews curves set/plot and the Fractal Foam permit direct visualizations of data optima; especially where nodes and peaks are expected. This latter might be applicable to selection of target anatomy and treatment parameters.

Still further, the following reviews different methods for visualizing complex data sets: http://home.comcast.net/~patrick.hoffman/viz/MIV-datamining. More particularly, parameters and parametrics from one patient's data collection can be used in comparisons and mathematical analyses across/among numerous patients, including the response of different patients to similar or dissimilar treatments, as well as the efficacy and efficiency of such treatments. Thus, the instant methods include the use of inter patient analyses to establish and standardize new treatment parameters as well to optimize treatment outcome efficiency and efficacy. A continual diagnosis, treatment optimization, and treatment efficacy/efficiency feedback loop may be established to continually optimize patient treatment methods.

EXAMPLES

Objects and advantages of this disclosure are further illustrated by the following examples, but the particular materials and amounts thereof recited in these examples, as well as other conditions and details, should not be construed to unduly limit this disclosure.

Exemplary Stretching Exercises

To carry out toe stretch up (1): cross right leg over left knee; grasp toes and pull upward; hold for 1 minute; repeat using other foot.

To carry out toe stretch down (2): cross left leg over right knee; place right thumb on ball of left foot, and push up towards the top of the foot; use the rest of the fingers to wrap the toes around the thumb; hold for 1 minute; repeat using other foot.

Stretch (3) foot mobilization is carried out as follows: grasp the metatarsal phalangeal joint area above the big toe on left foot between thumb and forefinger of left hand; grasp adjoining toe bone between thumb and forefinger of right hand (note that the fingers are not on the toe, but above the toe area as shown in foot bone illustrations to right of exercise drawings); move toe bones up and down in alternate directions a total of 10 times; shift hand position down foot, and move toe bones up and down in alternate directions; shift hand position down, repeating up and down hand movements; shift hand position down to final position, with right hand on pinky bone and left hand on adjoining toe bone; repeat up and down hand movements; work back up foot, toward big toe; repeat, going up and down left foot again; repeat entire exercise using other foot.

Straight ankle stretch (4) is carried out as follows: cross right leg over left knee; place left hand over right foot; gently pull your foot toward yourself until you feel a stretch; hold for 1 minute; repeat for other ankle.

To carry out ankle stretch up (5): cross right leg over left knee; place left hand over right foot; gently pull your foot towards you as per stretch 4 as well as upward towards the ceiling until you feel a stretch; hold for 1 minute; repeat for other ankle.

To carry out ankle stretch down (6): cross right leg over left knee; place left hand over right foot; gently pull your foot toward you (as per stretch (4)) as well as toward the floor until you feel a stretch; hold for 1 minute; repeat for other ankle.

To carry out stretches (4), (5), and (6) with an alternative ankle position, sit with your leg bent in front of you; place one hand on your lower leg for stability and grasp your foot near your toes with the other hand.

To carry out shin stretch (7): sit with your knees bent and place one foot flat on the floor under a couch or cabinet; tuck your other foot under elevated leg in a comfortable position; using the edge of the couch or cabinet as leverage, slowly slide backwards on your bottom until you feel a gentle stretch in the front of your leg and foot; hold stretch position for 1 minute; repeat using other leg. Alternatively, a low rolling chair or stool can be used if the patient has difficulty getting up from the ground.

Patient 1 Case Study

Chief Complaint: Patient is a 79 year old male; complaints of bilateral numbness/paresthesia, pain, shooting pains, hypersensitivity, and pins and needles bilaterally distal to the knees.

Cause of Neuropathy: Unknown.

Progression of symptoms and present symptoms: Patient stated that he became aware of the symptoms approximately a little over a year ago. Patient reported the symptoms started in the toes and progressed proximally and severity of symptoms increased over time. Upon intake, patient was symptomatic bilaterally toes to knees. Patient rated the pain in his feet/legs as 9/10 and numbness/paresthesia as 8/10 and burning as a 9/10 bilaterally. Patient rated his numbness and pain both as "moderate." Patient reported that his symptoms seemed to increase in severity at night and prevented him from getting more than 6 hours sleep. The severity of symptoms increased with physical activities including weight bearing. Patient noted that his balance and coordination seemed to have worsened over the past year and have been, "iffy lately."

Treatment History: Patient has seen a neurologist and stated that he has had an EMG done.

Imaging/Diagnostic studies: EMG positive for peripheral neuropathy

Medications: Thyroxin

Work: Patient is retired

Exercise and Activities: Patient's exercise and activities were limited due to his lower extremity symptoms.

Past Medical and Surgical History: Patient reports hypothyroid Dx which is being maintained with medication.

Physical Exam: A physical exam was performed and distal pulses were palpable bilaterally in the lower extremities. Patient had bilateral positive Tinel's Test for nerve compression at the tarsal tunnels bilaterally. Patient was tested with a 256 Hz tuning fork and had a loss of vibration sensation bilaterally distal to the waist.

Patient was tested with a Wartenberg pinwheel and had a hyperesthesia to pinprick sensation distal to the knee on the left, and hyperesthesia distal to the tibial tuberosity on the right.

Bilateral loss of joint motion was noted at the navicular, cuboid, and the 1-5 metatarsal heads.

Diagnosis: Bilateral lower extremity peripheral neuropathy; Bilateral ankle joint dysfunction.

Treatment Plan: Traction manipulation of foot/ankle joints were used to restore motion and decrease irritation to surrounding tissues. Laser therapy using a class IV laser at 970 nm wavelength was used to decrease pain and enhance treatment process and aid in restoration of function. All treatments were 6 minutes total in the lumbar nerve roots (3 minutes per side) and 12 minutes per lower extremity.

| Visit | Day | Power Root | Time (min) | Power Extremity | Time L/R (min) | Phase | Cooling | Re-Exam |
|---|---|---|---|---|---|---|---|---|
| 1st | 0 | 6.5 W | 6 | 5.5 W | 12/12 | 1 | post | |
| 2nd | 5 | 7.5 W | 6 | 6.5 W | 12/12 | 1 | post | |
| 3rd | 7 | 7.5 W | 6 | 6.75 W | 12/12 | 1 | post | yes |
| 4th | 12 | 7.5 W | 6 | 7 W | 12/12 | 4 | post | |
| 5th | 14 | 7.5 w | 6 | 7.5 W | 12/12 | 4 | post | |
| 6th | 19 | 7.5 W | 6 | 7.5 W | 12/12 | 4 | post | |
| 7th | 21 | 7.5 W | 6 | 7.5 W | 12/12 | 5 | post | |
| 8th | 26 | 7.5 W | 6 | 7.5 W | 12/12 | 5 | post | yes |
| 9th | 28 | 7.5 W | 6 | 7.5 W | 12/12 | 6 | post | |
| 10th | 33 | 7.5 W | 6 | 7.5 W | 12/12 | 6 | post | |
| 11th | 35 | 7.5 W | 6 | 7.5 W | 12/12 | 6 | post | |
| 12th | 40 | 7.5 W | 6 | 7.5 W | 12/12 | 6 | post | yes |
| 13th | 42 | 7.5 W | 6 | 7.5 W | 16/8 | 7 | post | |
| 14th | 47 | 7.5 W | 6 | 7.5 W | 16/8 | 7 | post | |
| 15th | 52 | 7.5 W | 6 | 7.5 W | 16/8 | 7 | post | yes |

Re-Examination on Visit 3:

Tinel's Test was positive for compression bilaterally at the tarsal tunnels. Vibration sense of the lower extremities was tested with a 256 Hz tuning fork. Patient had a loss of vibration sensation distal to the proximal ¼ leg on the right and absent distal to proximal ⅓ leg on the left.

Patient was tested with a Wartenberg pinwheel and had a bilateral hyperesthesia distal to distal ⅓ legs.

Loss of motion bilateral cuboid and 1-5 metatarsal heads noted.

Patient rated the pain in his feet 5/10, numbness 4/10 and burning now present just in the toes as 3/10. Patient seemed to be making satisfactory progress as far as his neuropathic symptoms are concerned. Patient overall notes in general, a significant overall decrease in his symptoms.

Re-Examination on Visit 8:

Tinel's Test was positive bilaterally at the tarsal tunnels. Vibration sense of the lower extremities was tested with a 256 Hz tuning fork. Patient had vibration sensation now absent only distal to ½ foot on the left, and absent only distal to the MTP joints on the right.

Patient was tested with a Wartenberg pinwheel and all pinprick sensation was present. Patient reported having hyperesthesia distal ½ feet bilaterally.

Loss of motion bilateral cuboid and 1-5 metatarsal heads noted.

Patient rated the pain in his feet 5/10, numbness 5/10 and burning at 3/10 bilaterally.

Re-Examination Visit 12:

Tinel's Test was positive bilaterally at the tarsal tunnels. Vibration sense of the lower extremities was tested with a 256 Hz tuning fork. Patient had vibration sensation now absent bilaterally plantar forefeet.

Patient was tested with a Wartenberg pinwheel and all pinprick sensation was present with no hyperesthesia on the right. Patient reported a hyperesthesia to pinprick sensation distal to the MTP joints on the left.

Patient rated the pain in his feet 4/10, numbness at 2/10 and burning 1/10 bilaterally. Symptoms now only present in the distal ¼ feet.

Re-Examination Visit 15:

Tinel's Test was positive bilaterally at the tarsal tunnels. Vibration sense of the lower extremities was tested with a 256 Hz tuning fork. Patient reported vibration sensation hypoesthetic distal balls of the feet bilaterally.

Patient was tested with a Wartenberg pinwheel and all pinprick sensation was present with hyperesthesia bilaterally.

Patient rated the pain in his feet 2/10, numbness at 2/10 and burning 2/10 bilaterally.

Symptoms now only present in the distal, plantar ¼ feet.

Figure 20:
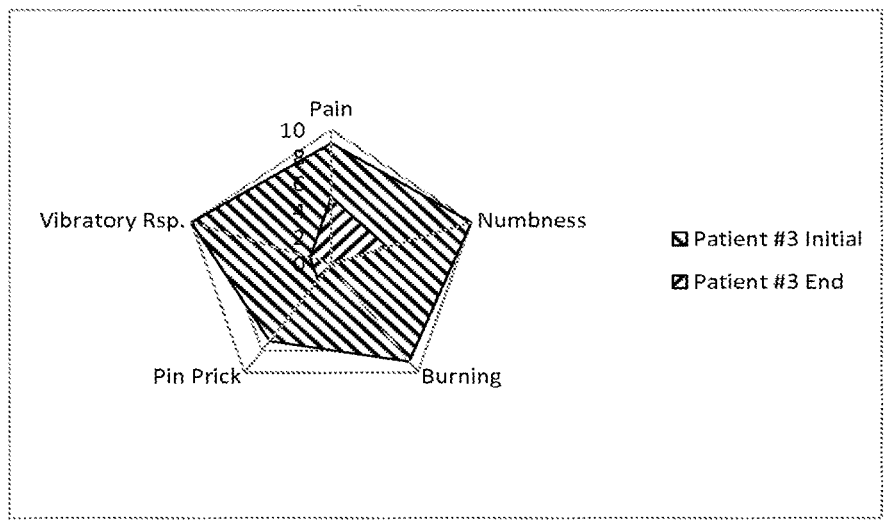
FIGS. 20-22 are graphical representations of the results shown in FIG. 19.

Results for Patient 1 are shown in the table of FIG. 19, and a graphical representation of such results is shown in FIG. 20.

Patient 2 Case Study

Chief Complaint: Patient is a 65 year old female; complained of bilateral numbness/paresthesia, shooting pains, pins and needles and sensitivity distal to the distal ⅓ legs bilaterally. Patient also complained of bilateral distal hand/finger paresthesia as well.

Cause of Neuropathy: Diabetes

Progression of symptoms and present symptoms: Patient stated she became aware of the symptoms approximately 2 years ago. Patient report the symptoms started in the toes and severity and surface areas of symptoms seems to be increasing over time. Patient is currently symptomatic bilaterally distal to the distal ⅓ legs bilaterally. Patient reported her balance has gotten worse over time, and had to consciously be more careful as she walked. She notes paresthesia in the fingers bilaterally. Patient rated her numbness/paresthesia as 6/10, pain at 9/10 and burning at 4/10 bilaterally.

Treatment History: Patient had seen a neurologist and had a Needle EMG which was positive for peripheral nerve dysfunction. Patient had been prescribed Gabapentin which she reports helps her to sleep.

Imaging/Diagnostic studies: Patient reported having a NCV study which was positive for peripheral nerve dysfunction.

Medications: Patient taking Gabapentin for her lower extremity complaints

Allergies: Patient denies.

Exercise and Activities: Patient's exercise and activities were limited due to her lower extremity symptoms.

Past Medical and Surgical History: Pt. diagnosed with Type 2 Diabetes approx. 2 years ago.

Physical Exam: A physical exam was performed and distal pulses were palpable bilaterally in the lower extremities. Patient had bilateral negative Tinel's Test for nerve compression at the tarsal tunnels bilaterally. Patient was tested with a 256 Hz tuning fork and had a loss of vibration sense distal to the knee on the right and absent distal to the proximal ⅕ leg on the left.

Patient was tested with a Wartenberg pinwheel and has a loss of pinprick sensation distal to the proximal ¼ leg on the right with hyperesthesia from the knee to the proximal leg on the right. Patient had a loss of pinprick sensation distal to the proximal ¼ thigh on the left Patient's feet/metatarsal areas were not overly sensitive to compression (+Jump); reflexes were 2/4 at the knees bilaterally, and 0/4 bilaterally at the Achilles with no beats of clonus.

Babinski sign for was negative bilaterally. Bilateral loss of joint motion was noted at the lunate, navicular, cuboid, and the 1-5 metatarsal heads. L4-S1 motor function appeared grossly intact bilaterally.

Diagnosis: Bilateral lower extremity peripheral neuropathy; Bilateral ankle joint dysfunction.

Treatment Plan: Traction manipulation of foot/ankle joints to restore motion and decrease irritation to surrounding tissues. Laser therapy using a class IV laser at 970 nm wavelength was used to decrease pain and enhance treatment process and aid in restoration of function. All treatments were 6 minutes total in the lumbar nerve roots (3 minutes per side) and 12 minutes per lower extremity.

| Visit | Day | Power Root | Time (min) | Power Extremity | Time L/R (min) | Phase | Cooling | Re-Exam |
|---|---|---|---|---|---|---|---|---|
| 1st | 0 | 6.5 W | 6 | 5.5 W | 12/12 | 1 | during & post | |
| 2nd | 5 | 6 W | 6 | 5 W | 12/12 | 1 | during & post | |
| 3rd | 7 | 6 W | 6 | 5 W | 12/12 | 2 | Post | yes |
| 4th | 12 | 6.25 W | 6 | 5.25 W | 12/12 | 4 | post | |
| 5th | 14 | 3 w | 6 | 2 W | 12/12 | 4 | post | |
| 6th | 19 | 3.25 W | 6 | 2.25 W | 12/12 | 4 | post | |
| 7th | 21 | 3.75 W | 6 | 2.75 W | 12/12 | 4 | post | |
| 8th | 26 | 3.75 W | 6 | 2.75 W | 12/12 | 4 | post | yes |
| 9th | 28 | 3.75 W | 6 | 2.75 W | 12/12 | 6 | during & post | |
| 10th | 33 | 4 W | 6 | 3 W | 12/12 | 6 | during & post | |
| 11th | 35 | 4 W | 6 | 3 W | 12/12 | 6 | during & post | |
| 12th | 40 | 4.25 W | 6 | 3.25 W | 12/12 | 6 | during & post | yes |
| 13th | 42 | 4.25 W | 6 | 3.25 W | 12/12 | 6 | during & post | |
| 14th | 47 | 4.25 W | 6 | 3.25 W | 12/12 | 6 | post | |
| 15th | 49 | 4.25 W | 6 | 3.25 W | 12/12 | 6 | post | yes |
| 16th | 62 | 4.25 W | 6 | 3.25 W | 12/12 | 6 | none | yes |
| 17th | 132 | 4.25 W | 6 | 3.25 W | 12/12 | 7 | none | yes |

Re-Examination on Visit 3:

Tinel's Test was negative for compression bilaterally at the tarsal tunnels. Vibration sense of the lower extremities was tested with a 256 Hz tuning fork. Vibration sense was now present to distal ⅓ leg on right and now present to distal ¼ leg on left.

Patient was tested with a Wartenberg pinwheel and has a loss of pinprick sensation distal to ½ foot with hyperesthesia to pinprick ankle to ½ foot on the right. Patient reported loss of pinprick sensation distal to the ankle with a hyperesthesia from distal ¼ leg to ankle on the left.

Patient self-rated symptoms were pain in the lower extremities at 4/10, numbness at 4/10 and burning at 4/10 with a smaller surface area of symptoms, but still noticeable in the distal lower extremities.

Bilateral loss of joint motion was noted at the 1-5th metatarsal heads

Patient reports improvement in perception of vibration sense as well as some reduction in her symptoms. At this point the initial goal of determining if she would respond has been met.

Re-Examination on Visit 8:

Vibration sense of the lower extremities was tested with a 256 Hz tuning fork. Vibration sense now present to ½ feet bilaterally.

Patient's distal extremities were tested with a Wartenberg pinwheel, patient reported loss of pinprick sensation bilaterally distal to ½ feet. Patient noted a hyperesthesia from ½ foot to the ankle on the left.

Bilateral loss of joint motion was noted at the navicular, cuboids, and the 1-5th metatarsal heads Patient self-rated symptoms were pain in the lower extremities at 4/10, numbness at 4/10 and burning at 4/10

Patient reported she has been having some minor bilateral cramping in the feet today. Recommended continued stretching at home.

Patient overall noted in general a significant overall decrease in her symptoms.

Re-Examination on Visit 12:

Vibration sense of the lower extremities was tested with a 256 Hz tuning fork. Vibration sense now bilaterally absent only distal to the MTP joints. Patient's distal extremities were tested with a Wartenberg pinwheel, patient a loss of pinprick sensation only distal to the MTP joints bilaterally with no reported hyperesthesia.

Bilateral loss of joint motion was noted at the 1-5th metatarsal heads

Patient self-rated symptoms were pain in the lower extremities at 2/10, numbness at 2/10 and burning at 2/10 with symptoms most noticeable now in the distal plantar forefeet. Patient overall noted in general a significant overall decrease in her symptoms.

Re-Examination on Visit 15:

Vibration sense of the lower extremities was tested with a 256 Hz tuning fork. Vibration sense now present on the right and absent only on the ball of the foot on the left. Patient's distal extremities were tested with a Wartenberg pinwheel. Patient noted pinprick sensation now present and without hyperesthesia on the right. Patient noted a loss of pinprick sensation in the dorsal toes with hyperesthesia ½ foot to MTP joints on the left.

Bilateral loss of joint motion was noted at the 1-5th metatarsal heads

Patient self-rated symptoms were pain in the lower extremities at 2/10, numbness at 2/10 and burning at 2/10 with symptoms most noticeable now in the distal plantar forefeet. Patient overall noted in general a significant overall decrease in her symptoms.

Re-Examination on Visit 16:

Vibration sense of the lower extremities was tested with a 256 Hz tuning fork. Vibration sense now present bilaterally.

Patient's distal extremities were tested with a Wartenberg pinwheel. Patient noted pinprick sensation present on the right. Patient noted a small area of hyperesthesia on the left in the distal 1st toe Bilateral loss of joint motion was noted at the 1-5th metatarsal heads Patient self-rated symptoms were pain in the lower extremities at 1/10, numbness at 1/10 and burning at 1/10 with symptoms most noticeable now in the distal plantar forefeet. Patient notes that her only noticeable symptom is a stiff sensation in the distal forefeet.

Figure 21:
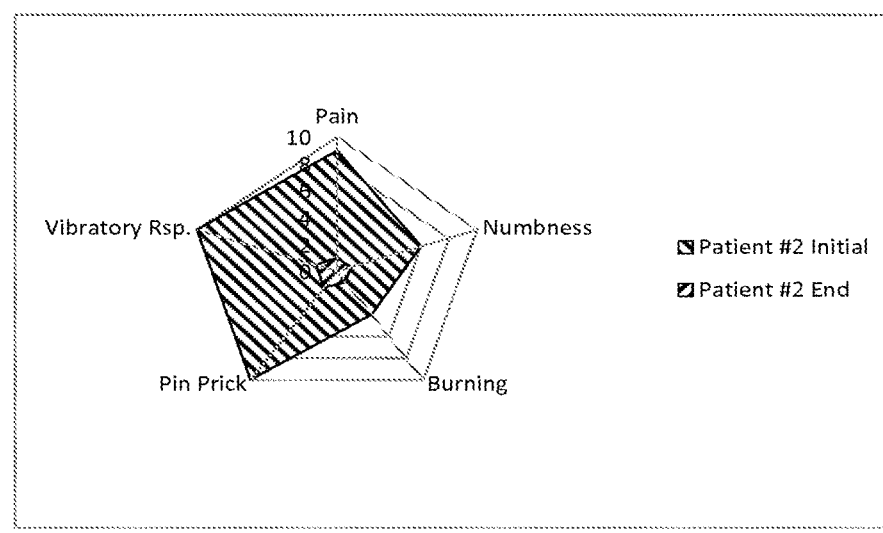

Results for Patient 2 are shown in the table of FIG. 19, and a graphical representation of such results is shown in FIG. 21.

Patient 3 Case Study

Chief Complaint: Patient is a 62 year old male; complaints of bilateral numbness/paresthesia, pain, shooting pains, hot burning, tingling/pins and needles. Patient notes some intermittent balance issues. Patient's symptoms were distal to hips bilaterally Cause of Neuropathy: Unknown.

Progression of symptoms and present symptoms: Patient stated he became aware of the symptoms approximately 5 years ago. Patient reported the symptoms started in the toes and progressed proximally and severity of symptoms has increased over time. Patient notes that balance has decreased over the years and he must be more careful when walking. Patient was symptomatic bilaterally distal to the hips. Patient rated the pain his feet/legs as 9/10, numbness/paresthesia as 10/10 and burning as 9/10 bilaterally. Patient reported that his symptoms do not seem to increase in severity at night although they can increase with weight bearing activities.

Treatment History: Patient had seen a Neurologist and had an EMG of his lower extremities.

Imaging/Diagnostic studies: EMG positive for peripheral neuropathy

Medications: Patient was taking Gabapentin 600 mg, Doxazosin 8 mg and zolpidem 10 mg as well as a multi vitamin Exercise and Activities: Patient's exercise and activities were limited due to his lower extremity symptoms.

Past Medical and Surgical History: Headaches, high blood pressure, depression, back pain, tinnitus, fatigue indigestion, arthritis, irregular sleep and gout.

Physical Exam: Distal pulses were palpable bilaterally in the lower extremities. Patient had negative Tinel's Test for nerve compression at the tarsal tunnels bilaterally. Patient was tested with a 256 Hz tuning fork and had a loss of vibration sensation distal to the knees bilaterally.

Patient was tested with a Wartenberg pinwheel and had a loss of pinprick sensation distal to the proximal ¼ legs bilaterally with a hyperesthesia to pinprick sensation from the knees to the proximal ¼ legs.

Diagnosis: Bilateral lower extremity peripheral neuropathy; Bilateral ankle joint dysfunction.

Treatment Plan: Traction manipulation of foot/ankle joints to restore motion and decrease irritation to surrounding tissues. Laser therapy using a class IV laser at 970 nm wavelength was used to decrease pain and enhance treatment process and aid in restoration of function. All treatments were 6 minutes total in the lumbar nerve roots (3 minutes per side).

| Visit | Day | Power Root | Time (min) C/L | Power Lower Extremity | Time L/R (min) | Power Upper Extremity | Time L/R (min) | Phase U/L | Cooling | Re-Exam |
|---|---|---|---|---|---|---|---|---|---|---|
| 1st | 0 | 6.5 W | 0/6 | 5.5 W | 12/12 | na | na | na/4 | during & post | |
| 2nd | 2 | 7.5 W | 0/6 | 6.5 W | 12/12 | na | na | na/4 | post | |
| 3rd | 7 | 7.5 W | 2/6 | 6.75 W | 8/8 | 6.5 W | 3/3 | 3/5 | post | yes |
| 4th | 9 | 7.5 W | 2/6 | 6.75 W | 8/8 | 6.75 W | 3/3 | 3/5 | post | |
| 5th | 15 | 7.5 W | 2/6 | 6.75 W | 8/8 | 6.75 W | 3/3 | 4/5 | post | |
| 6th | 45 | 7.5 W | 2/6 | 6.75 W | 8/8 | 6.75 W | 3/3 | 4/5 | none | |
| 7th | 51 | 7.5 W | 2/6 | 6.5 W | 8/8 | 6.5 W | 3/3 | 4/5 | none | yes |
| 8th | 53 | 7 W | 2/6 | 6 W | 8/8 | 6 W | 3/3 | 4/5 | none | yes |
| 9th | 58 | 7.5 W | 2/6 | 6.5 W | 8/8 | 6.5 W | 3/3 | 4/5 | none | |
| 10th | 60 | 7.5 W | 2/6 | 6.75 W | 8/8 | 6.75 W | 3/3 | 4/6 | post | |
| 11th | 72 | 7.5 W | 2/6 | 7.5 W | 8/8 | 7.5 W | 3/3 | 4/6 | post | |
| 12th | 74 | 6 W | 2/6 | 5 W | 8/8 | 5 W | 3/3 | 4/6 | post | |
| 13th | 79 | 6 W | 2/6 | 5 W | 8/8 | 5 W | 3/3 | 4/6 | post | |
| 14th | 81 | 6.25 W | 2/6 | 5.25 W | 8/8 | 5.25 W | 3/3 | 4/7 | none | |
| 15th | 86 | 6.75 W | 0/6 | 5.75 W | 12/12 | na | 0/0 | 4/7 | none | yes |

Re-Examination on Visit 3:

Tinel's Test was negative for compression bilaterally at the tarsal tunnels and fibular heads. Vibration sense of the lower extremities was tested with a 256 Hz tuning fork. Vibration sense was absent distal to distal ⅓ legs bilaterally.

Patient was tested with a Wartenberg pinwheel and had a loss of pinprick sensation distal to ½ leg on the right. Patient reported a loss of pinprick sensation distal to distal ⅓ leg on the left, with hyperesthesia ½ leg to distal ⅓ leg on the left.

Loss of motion bilateral navicular, cuboid and 1-5 metatarsal heads noted.

Patient rated the pain in his feet currently as 9/10, numbness as 9/10 and burning in the feet as 9/10 bilaterally.

Patient notes that while the symptoms are still the most severe in the toes, there is a more normal sensitivity to touch in the legs.

Re-Examination on Visit 8:

A re-examination was performed on the positive findings found on previous examination. Tinel's Test was negative for compression bilaterally at the tarsal tunnels and fibular heads. Vibration sense was absent distal to the ankles on both right and left feet.

Patient was tested with a Wartenberg pinwheel and had a loss of pinprick sensation distal to ½ feet bilaterally.

Loss of motion bilateral navicular, cuboid and 1-5 metatarsal heads noted.

Patient now rates the pain in his feet 9/10, numbness in his feet 8/10 and his burning at 1/10 bilaterally. Patient notes that he has very little pain in his feet other than the heel area. The pain and burning sensations are much diminished since onset of treatment. Pain is now bilaterally in the plantar heel area and could be plantar fasciitis.

Re-Examination on Visit 12:

Tinel's Test was negative for compression bilaterally at the tarsal tunnels and fibular heads. Vibration sense was now absent only in the plantar forefeet bilaterally.

Patient was tested with a Wartenberg pinwheel and had a loss of pinprick sensation at the distal ½ 1st toes bilaterally Loss of motion bilateral navicular, cuboid and 1-5 metatarsal heads noted.

Patient rated the pain in his feet 7⅜/10, numbness 5/10 bilaterally and burning 0/10 bilaterally. Patient's main pain still in the plantar heel area, relieved with rest and exacerbated with weight bearing. Recommend he is fitted with orthotics by his Podiatrist. Patient notes that he has much more normal sensitivity to touch, and that his sensation of numbness is a "puffy" sensation in the dorsal forefoot.

Re-Examination on Visit 15:

Tinel's Test was negative for compression bilaterally at the tarsal tunnels and fibular heads. Vibration sense was now hypoesthetic in the plantar forefoot on the right. Vibration sensation now present in the left foot.

Patient was tested with a Wartenberg pinwheel and reported presence of pinprick sensation bilaterally with no hyperesthesia.

Loss of motion bilateral navicular, cuboid and 1-5 metatarsal heads noted.

Patient rated the pain in his feet 6/10, numbness 7/10 bilaterally and burning 0/10 bilaterally. Patient reports that his pain is in the plantar heel area, relieved with rest and exacerbated with weight bearing. His neuropathy pain/burning seems to have resolved with treatment. He states that he has had plantar fasciitis in the past. Patient reports that his "numbness" is now only an "odd" sensation in the balls of his feet.

Figure 22:
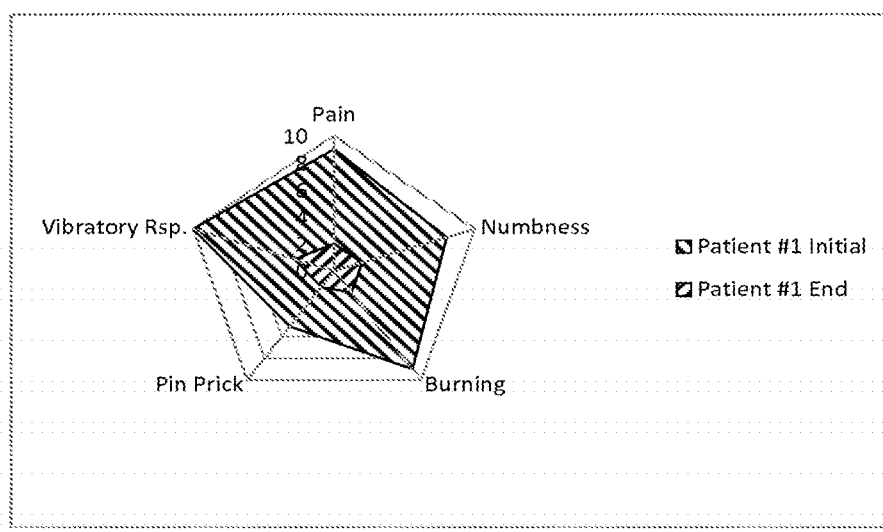

Results for Patient 3 are shown in the table of FIG. 19, and a graphical representation of such results is shown in FIG. 22.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A treatment generation system to provide treatment information to a plurality of local systems to treat sensory impairment in one or more body portions of patients comprising:

a network connection operably coupled to a plurality of local systems; and processing apparatus operably coupled to the plurality of local systems via the network connection and configured to:

provide an all-patient dataset from a plurality of sets of data indicative of damage at different damage regions of at least one body portion of the one or more body portions for a plurality of different patients over a plurality of treatments received from the plurality of local systems, generate treatment definitions for treating at least one of sensory impairment and vascular impairment in the at least one body portion using photonic energy from a therapeutic laser based on the data indicative of damage received from local systems and the all-patient dataset, wherein each treatment definition comprises a plurality of treatment regions of the patient to be exposed to photonic energy to treat the at least one body portion and a time period of exposure to photonic energy for each of the plurality of treatment regions, and transmit the generated treatment definitions to the plurality of local systems.

2. The system of claim 1, wherein the treatment generation system is further configured to:

determine the efficacy of the generated treatment definitions based on the all-patient dataset; and update the treatment definition generation algorithm used to generate the treatment definition based on the determined efficacies of the generated treatment definitions.

3. The system of claim 1, wherein generating treatment definitions based on the data indicative of damage received from local systems and the all-patient dataset comprises:

establishing correlations among the data indicative of damage received from local systems and the data indicative of damage already present in the all patient data set; and using such correlations to tailor the treatment definition.

4. The system of claim 1, wherein the treatment generation system is operably coupled to the plurality of local systems using the network connection via the internet.

5. The system of claim 1, wherein the therapeutic laser apparatus comprises a Class IV therapeutic laser.

6. The system of claim 1, wherein the data indicative of damage comprises subjective data collected from the patient indicative of damage at different damage regions of the at least one body portion.

7. The system of claim 1, wherein the data indicative of damage comprises objective measurement data indicative of damage at different damage regions of the at least one body portion, wherein the objective measurement data is collected using objective testing on the at least one body portion.

8. The system of claim 1, wherein the one or more body portions comprise one or more extremities of the patient, wherein the tissue of the at least one body portion comprises tissue of at least one extremity of the one or more extremities of the patient, wherein the data indicative of damage comprises data indicative of damage at different damage regions of the at least one extremity of the one or more extremities, wherein the different damage regions of the at least one extremity are consecutively located along the at least one extremity from the patient's torso to a distal end of the at least one extremity.

9. The system of claim 1, wherein the plurality of treatment regions comprises:
tissue in proximity to one or more nerve roots, and
tissue of the at least one body portion, wherein the tissue of the at least one body portion is located in a different location of the patient than the tissue in proximity to the one or more nerve roots.

10. The system of claim 1, wherein the at least one treatment definition further comprises a treatment power of the photonic energy for the at least one body portion.

11. A treatment generation system to provide treatment information to a plurality of local systems to treat sensory impairment in one or more body portions of patients comprising:
a network connection operably coupled to a plurality of local systems; and
processing apparatus operably coupled to the plurality of local systems via the network connection and configured to:
provide an all-patient dataset from a plurality of sets of data indicative of damage at different damage regions of at least one body portion of the one or more body portions for a plurality of different patients over a plurality of treatments received from the plurality of local systems,
generate treatment definitions for treating at least one of sensory impairment and vascular impairment in the at least one body portion using photonic energy from a therapeutic laser based on the data indicative of damage received from local systems and the all-patient dataset,
determine the efficacy of the generated treatment definitions based on the all-patient dataset, and
update the treatment definition generation algorithm used to generate the treatment definition based on the determined efficacies of the generated treatment definitions.

12. The system of claim 11, wherein generating treatment definitions based on the data indicative of damage received from local systems and the all-patient dataset comprises:
establishing correlations among the data indicative of damage received from local systems and the data indicative of damage already present in the all patient data set; and
using such correlations to tailor the treatment definition.

13. The system of claim 11, wherein the treatment generation system is operably coupled to the plurality of local systems using the network connection via the internet.

14. The system of claim 11, wherein the therapeutic laser apparatus comprises a Class IV therapeutic laser.

15. The system of claim 11, wherein the data indicative of damage comprises subjective data collected from the patient indicative of damage at different damage regions of the at least one body portion.

16. The system of claim 11, wherein the data indicative of damage comprises objective measurement data indicative of damage at different damage regions of the at least one body portion, wherein the objective measurement data is collected using objective testing on the at least one body portion.

17. A treatment system for use in treating sensory impairment in one or more body portions of patients comprising:
a local system usable to treat at least one of sensory impairment and vascular impairment using photonic energy from a therapeutic laser, the local system comprising a processor configured to allow a user to input data indicative of damage at different damage regions of and consecutively located along at least one body portion of the one or more body portions and to transmit the data indicative of damage; and
a treatment generation system operably coupled to and remotely located from the local system, the treatment generation system comprising a processor configured to:
receive the data indicative of damage at different damage regions of the at least one body portion from the local system,
generate a treatment definition for treating at least one of sensory impairment and vascular impairment in the at least one body portion using photonic energy from the therapeutic laser based on the data indicative of damage, wherein the at least one treatment definition comprises a plurality of treatment regions of the patient to be exposed to photonic energy to treat the at least one body portion and a time period of exposure to photonic energy for each of the plurality of treatment regions, and
transmit the treatment definition to the local system.

18. The system of claim 17, wherein the treatment generation system is further configured to:
generate an all-patient dataset from a plurality of sets of data indicative of damage at different damage regions of at least one body portion of the one or more body portions for a plurality of different patient over a plurality of treatments, and
wherein each treatment definition is further generated based on the all-patient dataset.

19. The system of claim 17, wherein each of the one or more local systems comprises: a therapeutic laser apparatus to deliver photonic energy to the plurality of treatment regions according to the received treatment definition to treat at least one of sensory impairment and vascular impairment in the at least one body portion.

20. The system of claim 17, wherein the treatment generation system is operably coupled to the local system via the internet.

* * * * *